(12) United States Patent
Parker et al.

(10) Patent No.: US 12,109,224 B2
(45) Date of Patent: Oct. 8, 2024

(54) USB1 DIRECTED REGULATION OF MIRNAS RELATED HEMATOPOIETIC DIFFERENTIATION AND AFFECTED IN MULTIPLE FORMS OF LEUKEMIA

(71) Applicants: The Regents of the University of Colorado, a body corporate, Denver, CO (US); Washington University, St. Louis, MO (US)

(72) Inventors: Roy R. Parker, Boulder, CO (US); Siddharth Shukla, Boulder, CO (US); Luis F. Z. Batista, Clayton, MO (US); Hochang Jeong, St. Louis, MO (US)

(73) Assignees: THE REGENTS OF THE UNIVERSITY OF COLORADO, A BODY CORPORATE, Denver, CO (US); WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 17/466,448

(22) Filed: Sep. 3, 2021

(65) Prior Publication Data

US 2022/0088053 A1    Mar. 24, 2022

Related U.S. Application Data

(60) Provisional application No. 63/074,772, filed on Sep. 4, 2020.

(51) Int. Cl.
*A61K 31/713* (2006.01)
*A61K 31/4375* (2006.01)

(52) U.S. Cl.
CPC ........ *A61K 31/713* (2013.01); *A61K 31/4375* (2013.01)

(58) Field of Classification Search
CPC .............. A61K 31/713; A61K 31/4375; C12N 15/111; C12N 15/113
USPC ...................... 435/6.1, 91.1, 91.31, 455, 458; 514/44 A, 44 R; 536/23.1, 24.5
See application file for complete search history.

(56) References Cited

PUBLICATIONS

Roberts et al (Nature Reviews, vol. 19, pp. 673-694 (2020)) (Year: 2020).*
Wang et al (Science, vol. 379, No. 6629, pp. 1-12 (2023)) (Year: 2023).*
Han et al (J. Molec. Med., vol. 98, pp. 615-632 (2020)) (Year: 2020).*

* cited by examiner

*Primary Examiner* — Jane J Zara
(74) *Attorney, Agent, or Firm* — Berg Hill Greenleaf Ruscitti LLP

(57) ABSTRACT

The invention includes methods and compositions for the treatment and prevention of a disease or condition resulting from dysregulation of USB1 and resulting expression of downstream miRNAs. In one preferred embodiment, the invention may include inhibiting the expression or activity of USB1 resulting in the downregulation of downstream miRNA expression. In alternative embodiments, the invention includes methods and compositions for the treatment and prevention of a disease or condition resulting from dysregulation of miRNAs downstream of USB1, namely through the inhibition of PAPD5 and/or PAPD7, resulting in the upregulation of said downstream miRNA expression.

2 Claims, 32 Drawing Sheets
Specification includes a Sequence Listing.

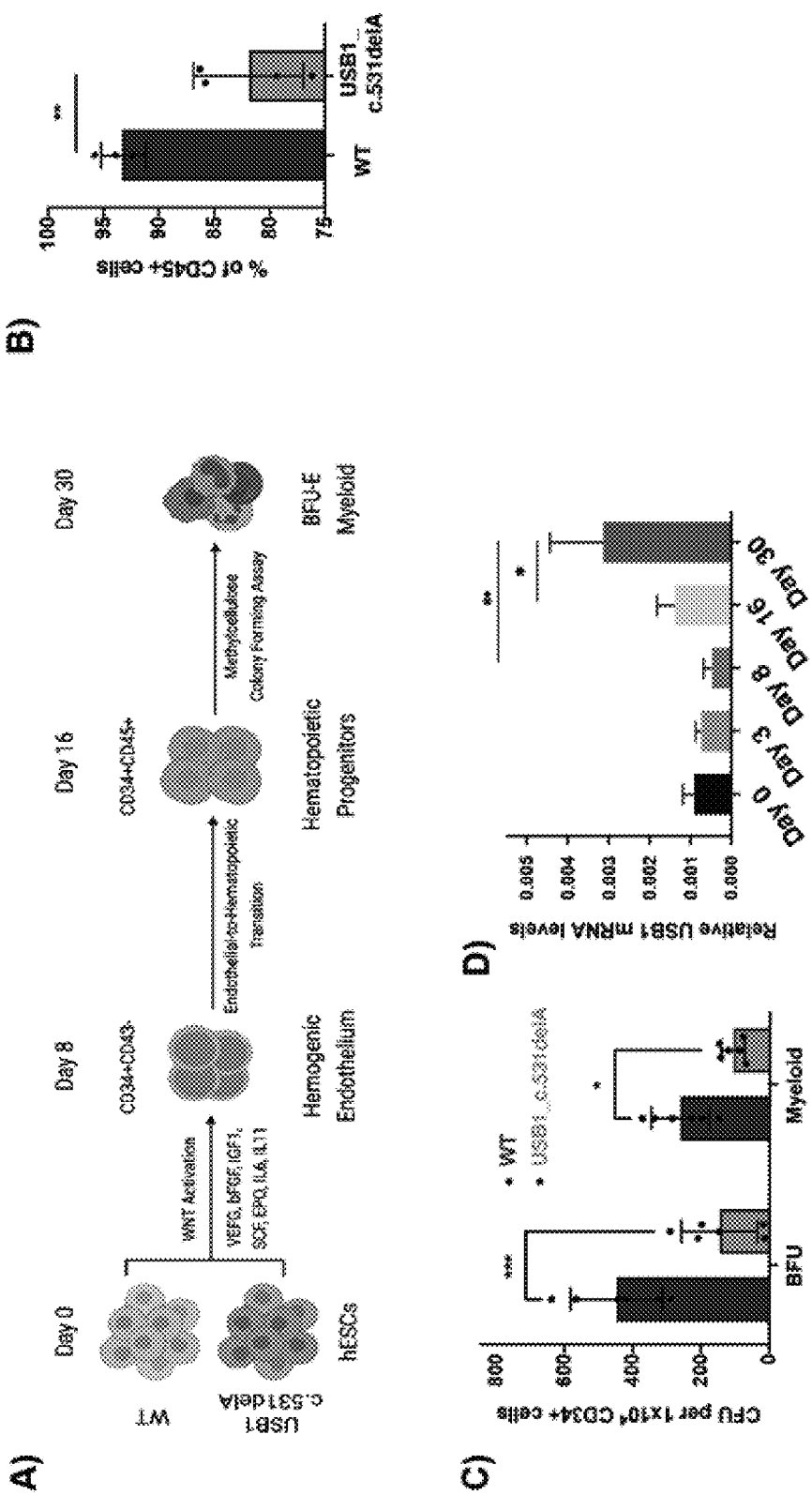
FIGS. 1A-D

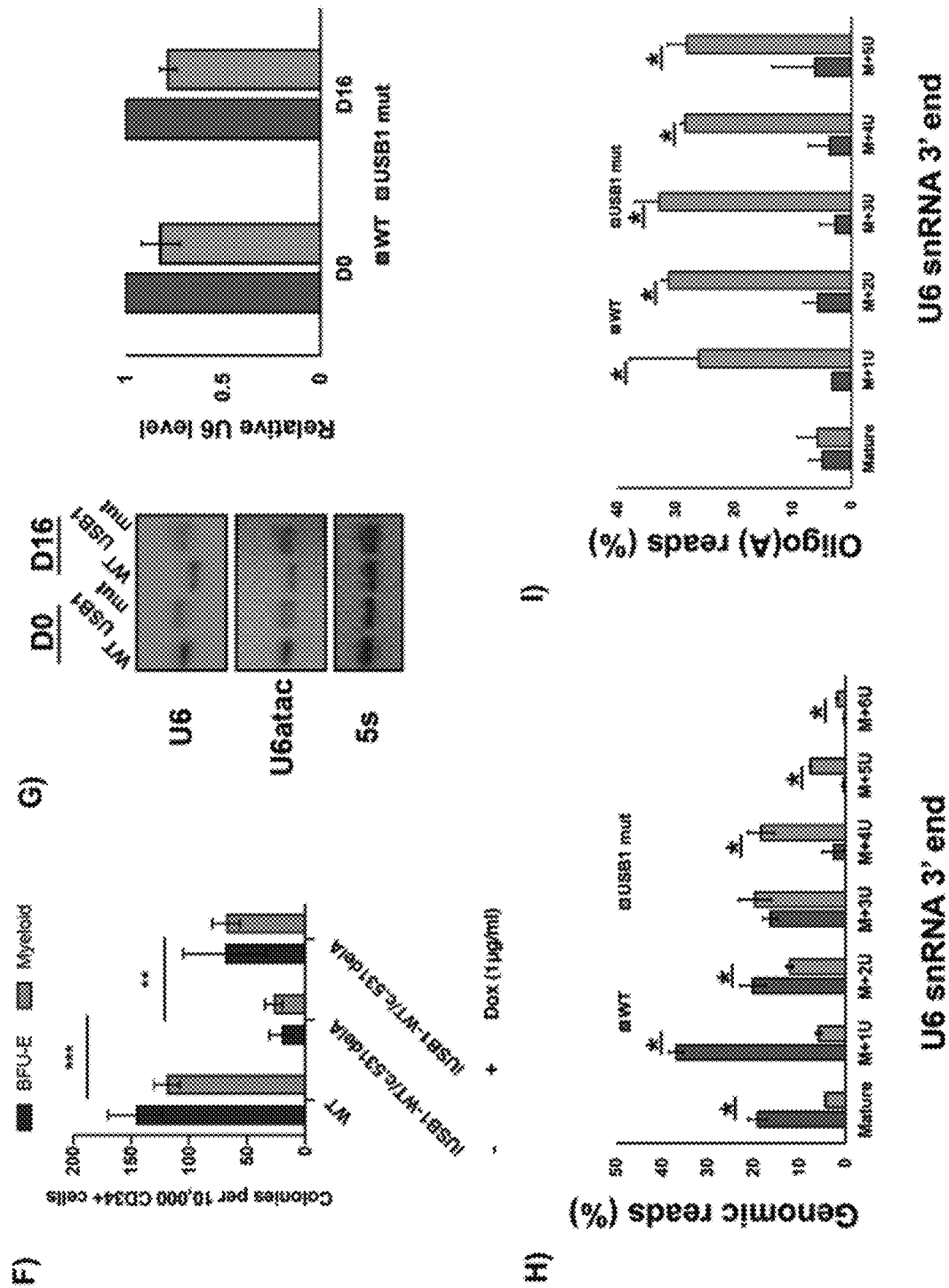
FIGS. 1F-I

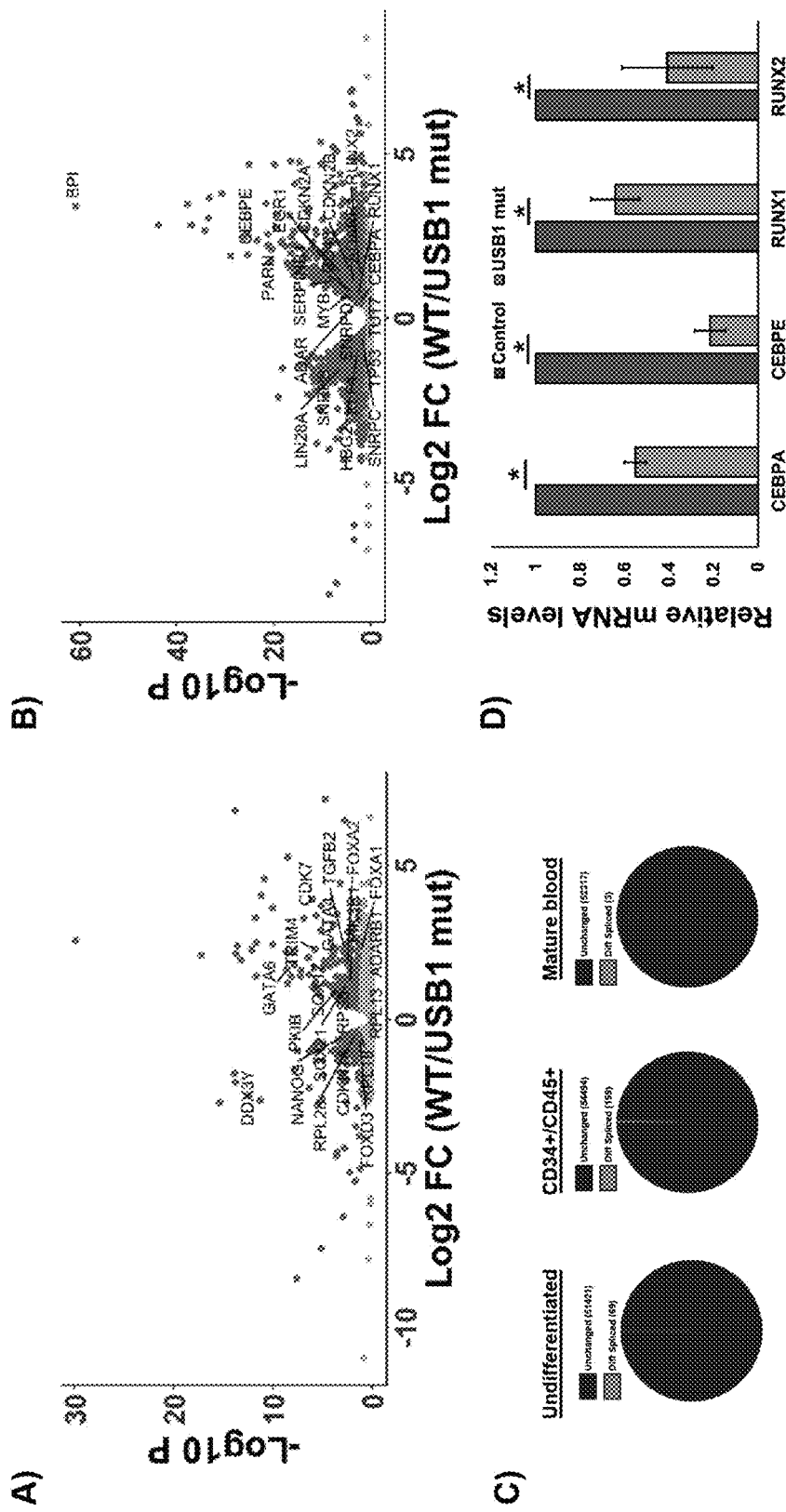
FIGS. 2A-D

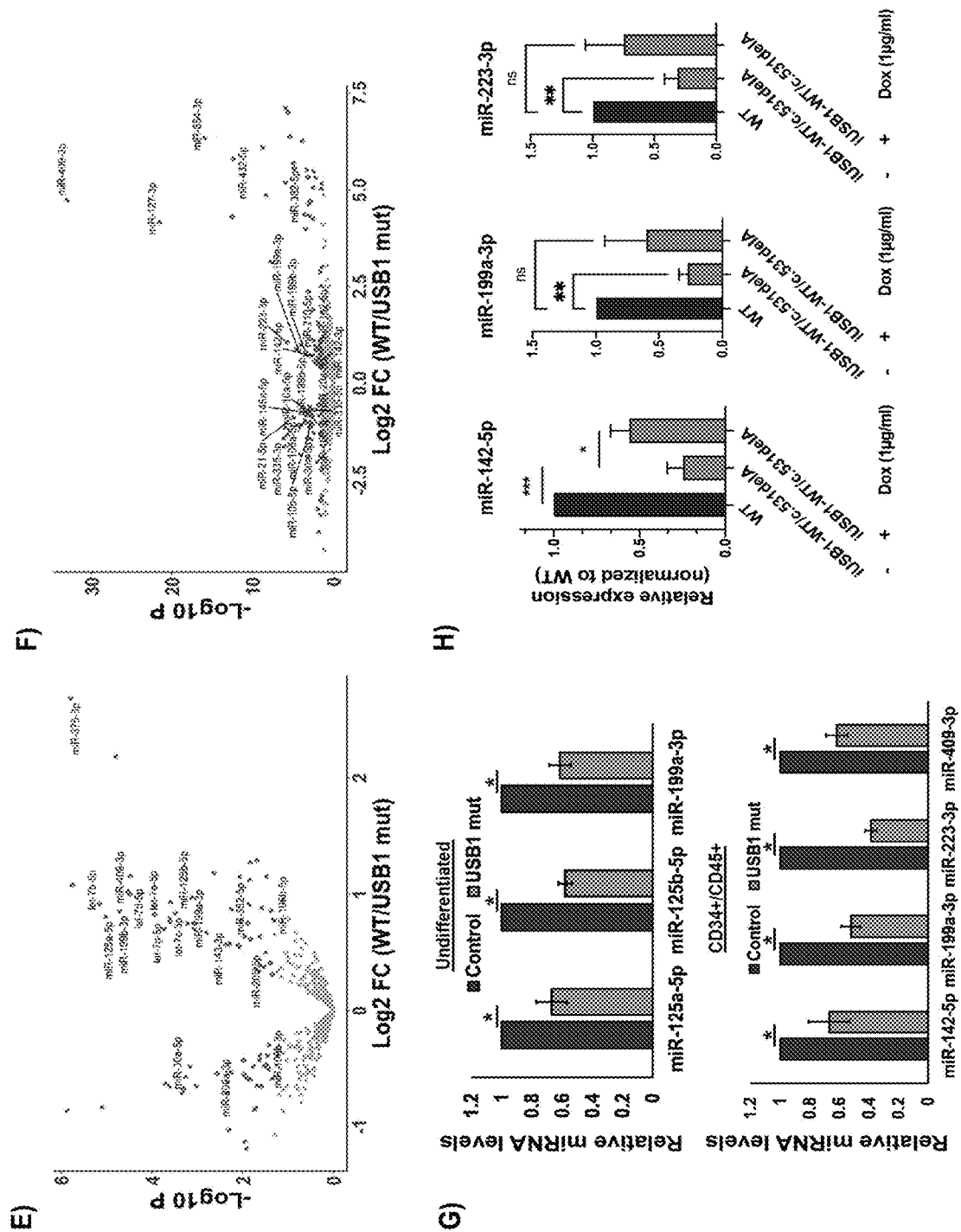
FIGS. 2E-H

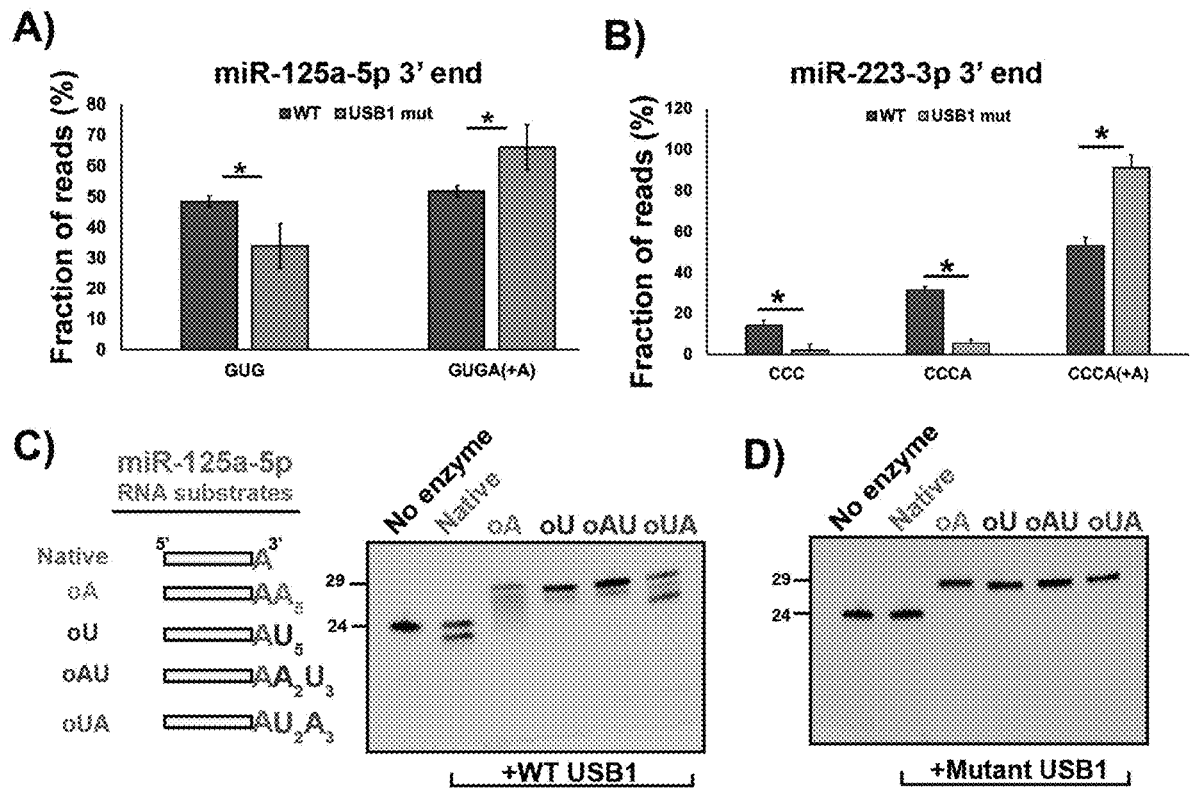
FIGS. 3A-D

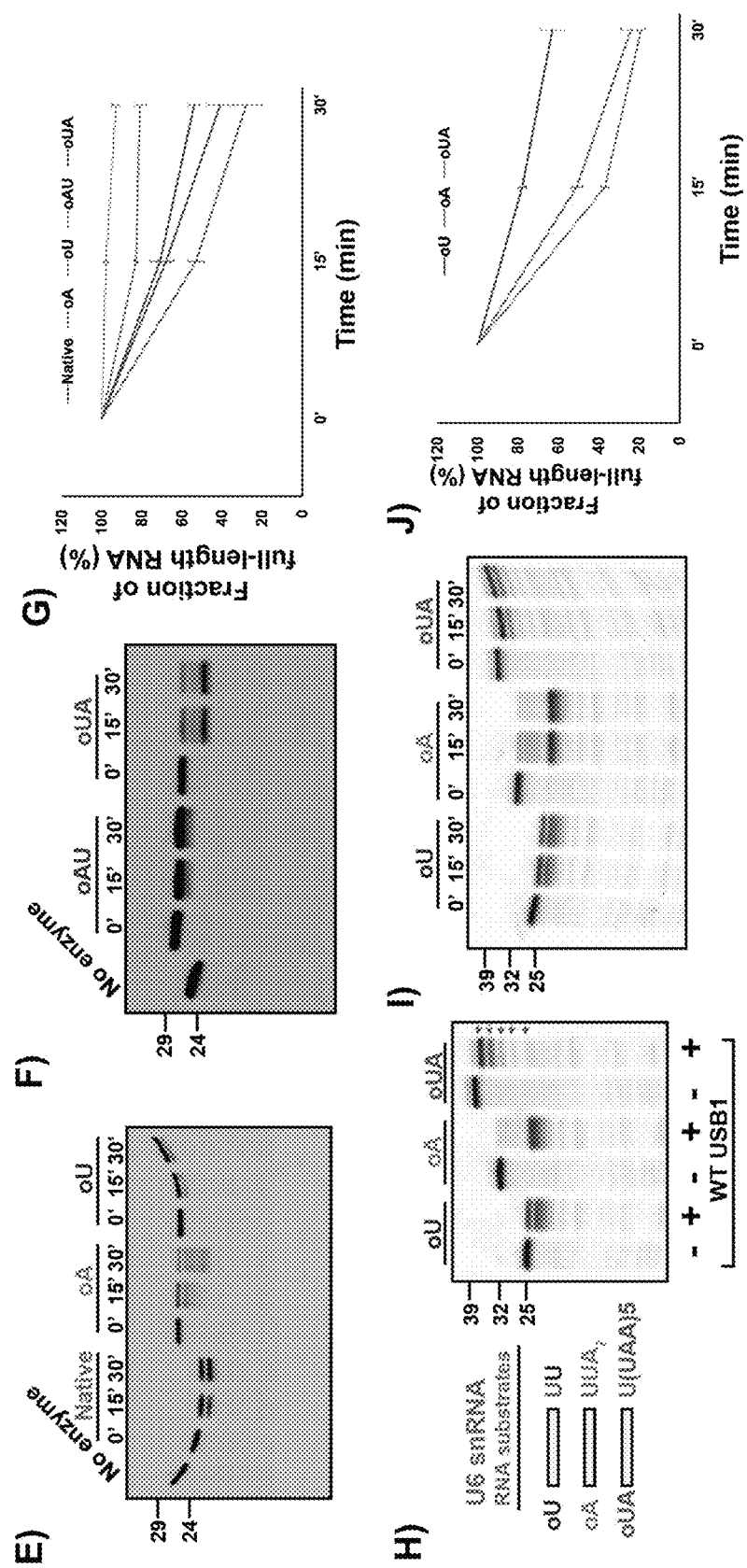
FIGURE 3E-J

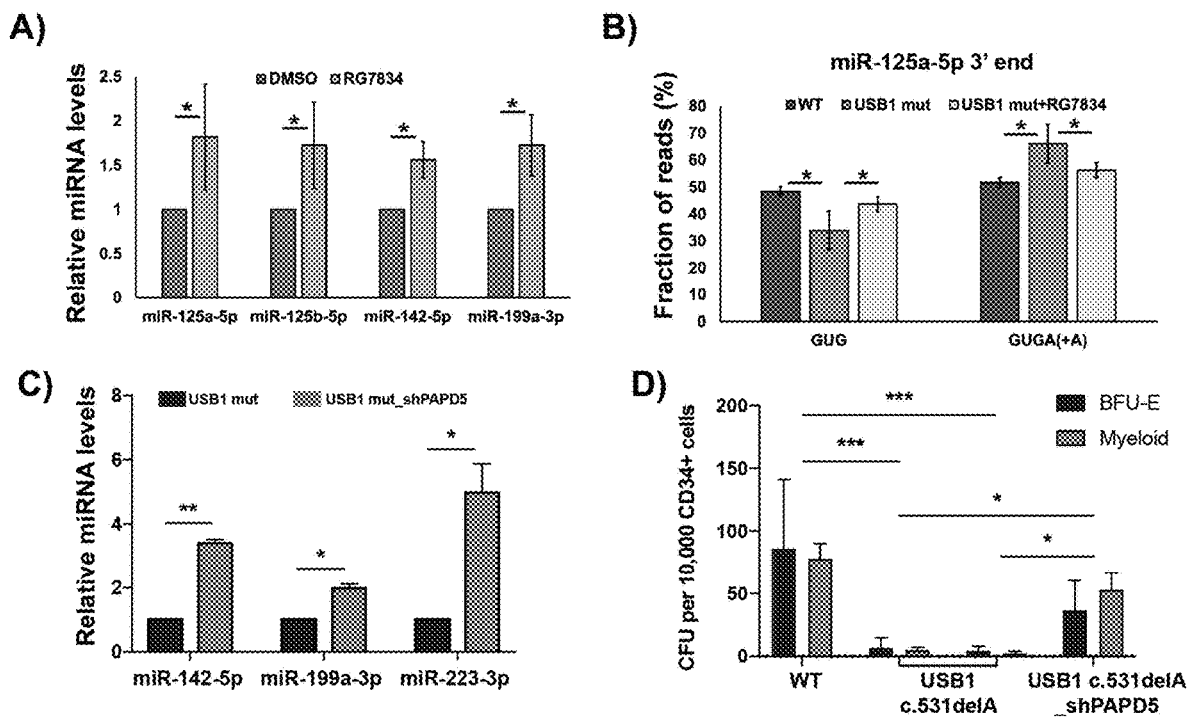
FIGS. 4A-D

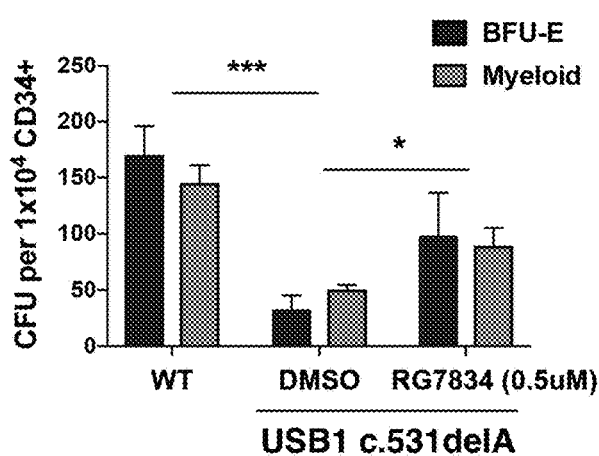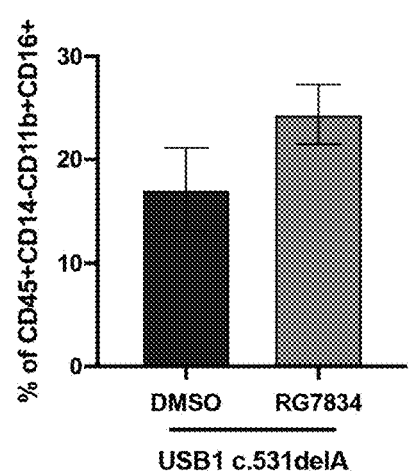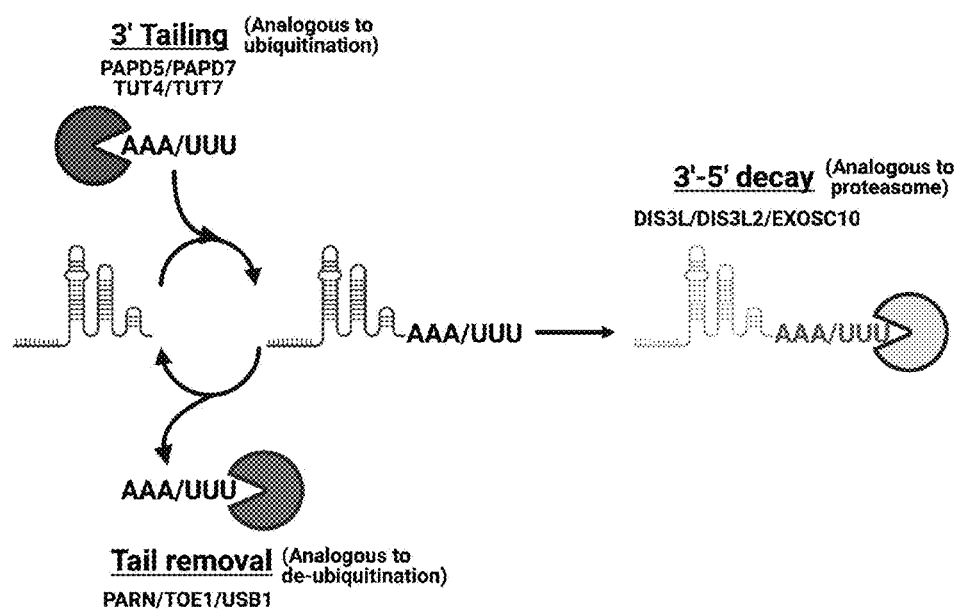
FIGS. 4E-G

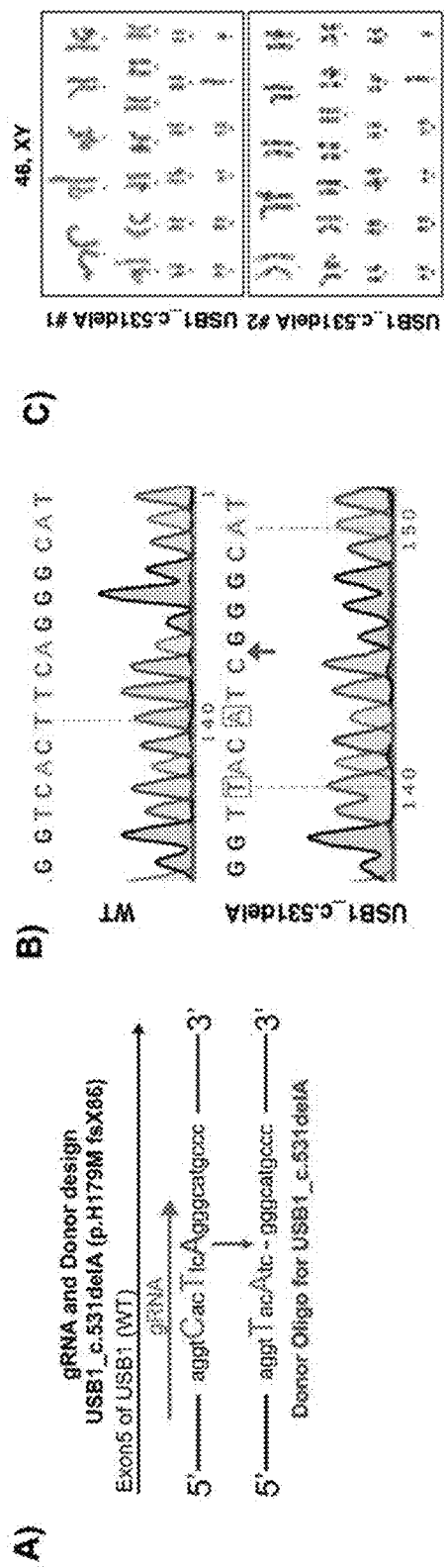
FIGS. 5A-C

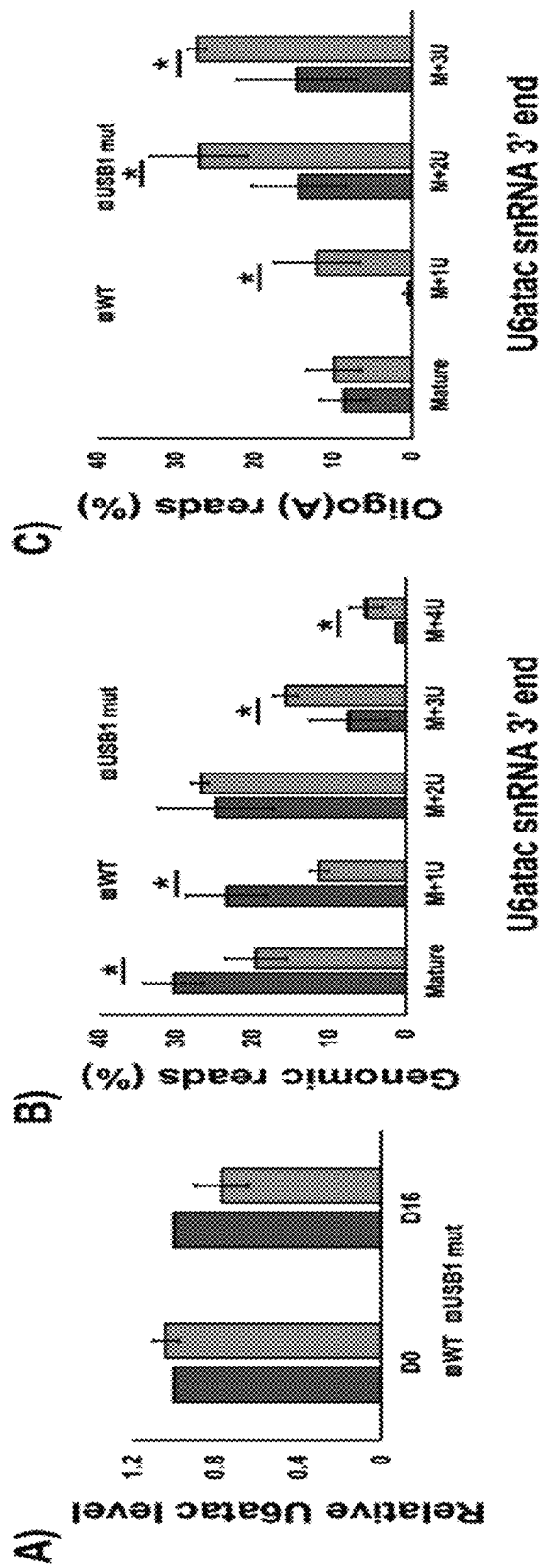
FIGURE 7A-C

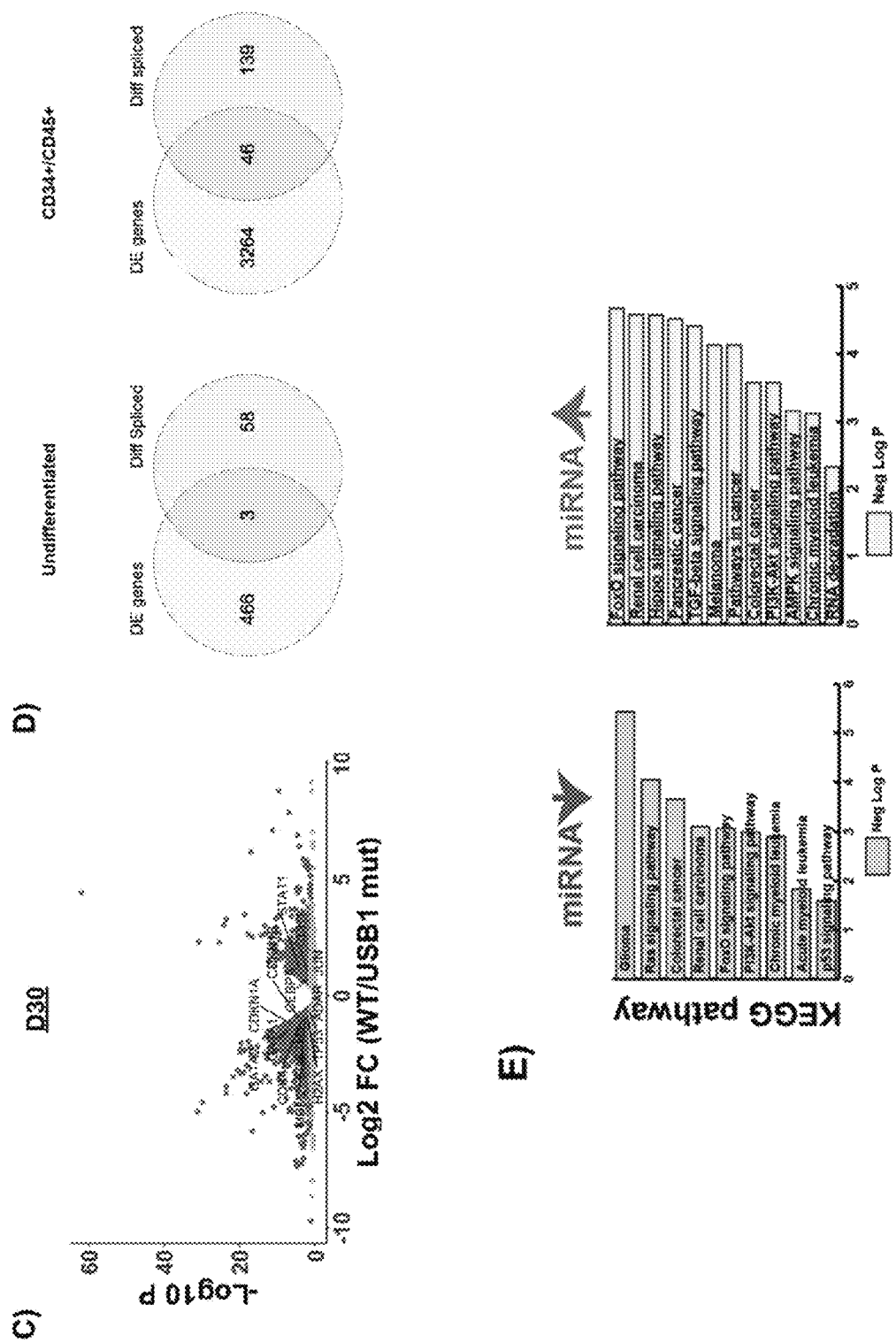
FIGS. 8C-E

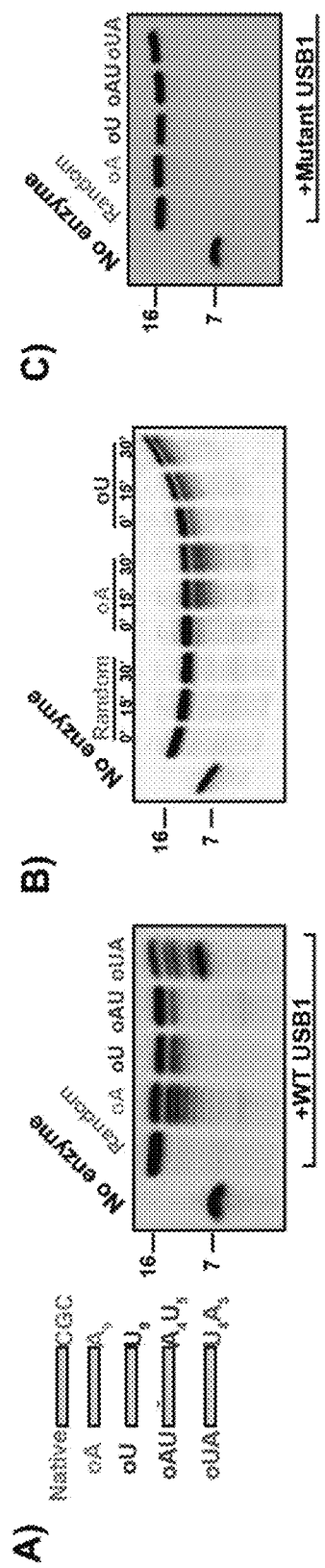
FIGS. 9A-C

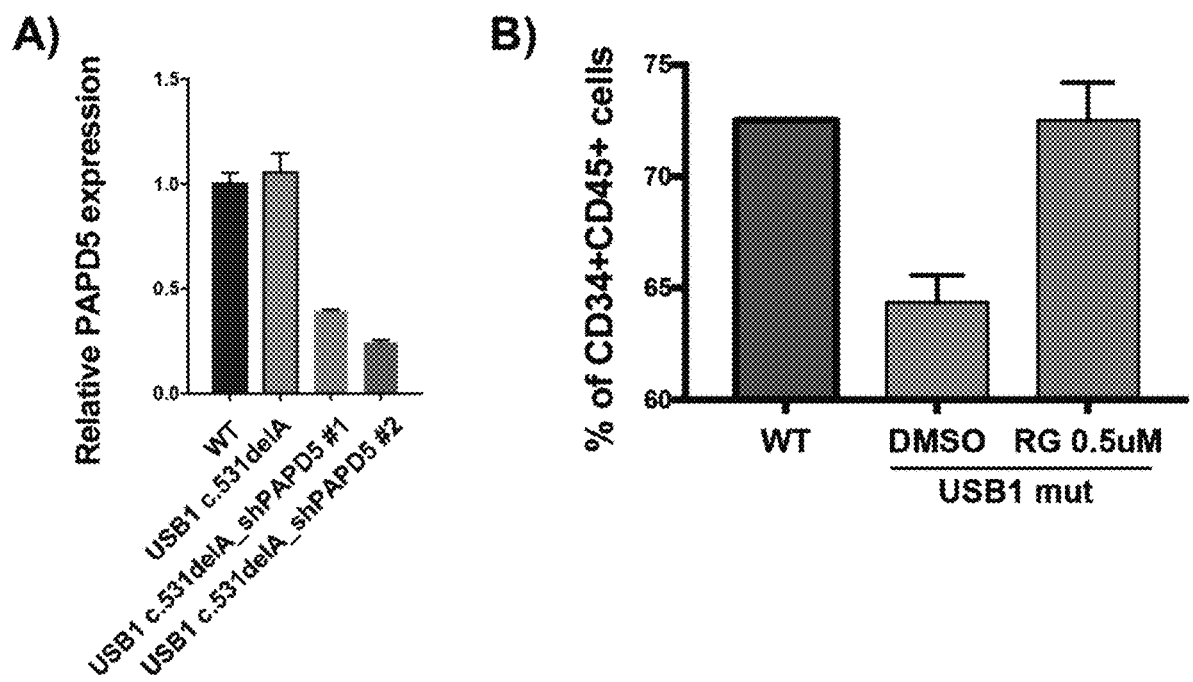
FIGS. 10A-B

USB1 DIRECTED REGULATION OF MIRNAS RELATED HEMATOPOIETIC DIFFERENTIATION AND AFFECTED IN MULTIPLE FORMS OF LEUKEMIA

CROSS-REFERENCE TO RELATED APPLICATIONS

This U.S. Non-provisional claims the benefit of and priority to U.S. Provisional Application No. 63/074,772 filed Aug. 4, 2021. The entire specifications and figures of the above-referenced applications are hereby incorporated, in their entirety by reference.

STATEMENT OF FEDERALLY SPONSORED RESEARCH

This invention was made with government support under grant number GM145443 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 16, 2021, is named "90245-00392-Sequence-Listing-AF-revised.txt" and is 18 bytes in size.

TECHNICAL FIELD

The invention relates to the therapeutic modulation of USB1 and the downstream regulation of miRNAs. The invention further related to the therapeutic inhibition of PAPD5/7 downstream regulation miRNAs, an in particular in subjects having USB1 dysregulation.

BACKGROUND

Poikiloderma with neutropenia (PN) is an autosomal-recessive bone marrow failure (BMF) syndrome with marked clinical overlap with dyskeratosis congenita (DC). However, unlike patients with DC, telomeres are not significantly shortened in patients suffering from PN, and therefore telomere length represents a clear distinguishable feature for the correct diagnosis of these different BMF syndromes. All PN patients identified to date harbor homozygous or compound heterozygous mutations in the human gene C16orf57, which encodes the evolutionarily conserved 3' to 5' RNA exonuclease U6 biogenesis 1 (USB1) (2-5). USB1 is required for the proper processing of U6 and U6atac snRNAs, and some splicing defects are observed in vitro and zebrafish models of USB1 deficiency. However, lymphoblastoid cells from PN patients do not exhibit reduced U6 snRNA levels and have normal pre-mRNA splicing. These results establish USB1-mediated PN as a singular BMF syndrome, where the underlying genetic cause has been identified but the molecular mechanisms leading to tissue failure remain obscure. As such, the pathological effects on the regulation of USB1 may provide therapeutic advances for BMF conditions, such as PN, and certain cancers as described below.

SUMMARY OF THE INVENTION

As described below, USB1 functions to deadenylate miRNAs, limiting their degradation and increasing their abundance, and this deadenylating activity of USB1 is important for regulating hematopoiesis. Inhibition of the enzymes responsible for miRNA adenylation, PAPD5 (SEQ ID NO. 2) & PAPD7 (SEQ ID NO. 3) rescued hematopoietic deficit observed in the USB1 mutant cells. As such, in one embodiment the invention includes methods and compositions for the treatment and prevention of a disease or condition resulting from dysregulation of USB1 and resulting expression of downstream miRNAs. In one preferred embodiment, the invention may include inhibiting the expression or activity of USB1 resulting in the downregulation of downstream miRNA expression. In alternative embodiments, the invention includes methods and compositions for the treatment and prevention of a disease or condition resulting from dysregulation of miRNAs downstream of USB1, namely through the inhibition of PAPD5 and/or PAPD7, resulting in the upregulation of said downstream miRNA expression.

Additional embodiments of the invention may be evidenced from the specification, claims and figures provided below.

BRIEF DESCRIPTION OF DRAWINGS

FIG. 1A-I. Loss-of-function mutation in USB1 causes hematopoietic impairment. A) Model depicting the workflow of hematopoietic differentiation from WT or USB1 c.531delA hESCs. Cellular identity is confirmed by expression of the correct differentiation markers at the different steps depicted in the model. B) Flow cytometry analysis of CD45+ cells obtained from day 16 of differentiation (average+/−S.D., n=4 biological replicates). C) CFC potential of definitive hematopoietic progenitors in WT and USB1 c.531delA cells (average+/−S.D., n=6 biological replicates). D) USB1 expression levels analyzed at different stages of definitive hematopoietic specification (average+/−S.D., n=3 biological replicates). E) Representative flow cytometry analysis of CD15 and CD66b within CD45+CD14− populations on Day 30 of differentiation (left panel). The populations were quantified and graphically presented (right panel, average+/−S.D., n=3 biological replicates). F) CFC potential of definitive hematopoietic progenitors in WT and iUSB1-WT/c.531delA cells, treated or not with doxycycline (DOX). Dox was added from day 8 to day 16 of differentiation (average+/−S.D., n=3 biological replicates). G) Representative northern blot for U6 or U6atac snRNA in either undifferentiated hESCs or CD34+CD45+ cells (left panel). Bar plot indicates U6 snRNA levels normalized to 5s rRNA (Average+/−S.D., n=3 biological replicates). H) and I) Bar plots depicting fraction of genomic and post-transcriptionally adenylated U6 snRNA 3' ends in WT and USB1 mutant (Average+/−S.D., n=2 biological replicates, *P<0.05, Fisher's exact test).

FIG. 2A-H. USB1 mutation affects both mRNA and miRNA levels during hematopoietic differentiation. A) and B) Volcano plot depicting transcriptome changes in A) undifferentiated hESCs and B) CD34+CD45+ hematopoietic progenitors between WT and USB1 mutant cells (Gray: unchanged; Magenta: differentially expressed). C) Pie charts depicting splicing changes in USB1 mutant compared to WT at different stages of differentiation. Numbers indicate total number of local splice variants in each category. D) Bar plot depicting levels of indicated mRNAs normalized to 5s rRNA in CD34+CD45+ hematopoietic progenitors (average+/−S.D., n=3 biological replicates, *P<0.05, Two-tailed unpaired Student's T-Test). E) and F) Volcano plot depicting miRNA changes in E) undifferentiated hESCs and F) CD34+CD45+ hematopoietic progenitors in WT and USB1 mutant cells (Gray: unchanged; Magenta: differentially expressed). G) Bar plot depicting levels of indicated miRNAs normalized to 5s rRNA in either undifferentiated hESCs (top panel) or CD34+CD45+ hematopoietic progenitor cells (bottom panel, average+/−S.D., n=3 biological replicates, *P<0.05, Two-tailed unpaired Student's T-Test). H) Relative miR-142-5p, miR-199a-3p, and miR223-3p levels normalized to RNU44 in iUSB1-WT/c.531delA on CD34+CD45+ hematopoietic progenitor cells (average+/−S.D., n=3 biological replicates, *P<0.05, P<0.01, *P<0.001, Two-tailed unpaired Student's T-Test).

FIG. 3A-J. USB1 deadenylates RNA substrates in vivo and in vitro. A) Bar plot depicting fraction of genomic and post-transcriptionally adenylated miR-125a-5p 3' ends in undifferentiated WT and USB1 mutant cells (average+/−S.D., n=2 biological replicates, *P<0.05, Fisher's exact test). B) Bar plot depicting fraction of genomic and post-transcriptionally adenylated miR-223-3p 3' ends in CD34+CD45+ hematopoietic progenitors in WT and USB1 mutant cells (average+/−S.D., n=3 biological replicates, *P<0.05, Fisher's exact test). C) and D) Representative gel image showing processing of miR-125a-5p substrates by C) wild-type USB1 or D) H208Q catalytic mutant. miR-125a-5p sequence includes a genomically encoded A at the 3' end (shown in red). Marker is a 24-nt miR-125a-5p native RNA. E) and F) Representative gel image depicting time-course measurement of USB1's activity on indicated miR-125a-5p RNA substrates. G) Line plot depicting degradation of miR-125a-5p RNA substrates with indicated 3' end modifications (average+/−S.D., n=3 technical replicates). H) Representative gel image showing processing of U6 snRNA substrates by wild-type USB1. Genomically encoded bases are shown in red. Red arrows show position of trimmed UAA intermediates for the oUA substrate incubated with wild-type USB1. I) Representative gel image depicting time-course measurement of USB1's activity on indicated U6 RNA substrates. J) Line plot depicting degradation of U6 RNA substrates with indicated 3' end modifications (average+/−S.D., n=3 technical replicates).

FIG. 4A-G. Inhibition of PAPD5/7 rescues miRNA levels and hematopoietic output in USB1 mutants. A) Bar plot depicting levels of indicated miRNAs normalized to 5s rRNA treated or with DMSO or RG7834 (104) (average+/−S.D., n=3 biological replicates, *P<0.05, Two-tailed unpaired Student's T-Test). B) Bar plot depicting fraction of genomic and post-transcriptionally adenylated miR-125a-5p 3' ends in undifferentiated USB1 mutant cells treated with RG7834 (1 μM) (average+/−S.D., n=2 biological replicates, *P<0.05, Fisher's exact test). C) Bar plot depicting miR-142-5p, miR-199a-3p and miR-223-3p levels in CD34+CD45+ hematopoietic progenitors (average+/−S.D., n=2 biological replicates, *P<0.05, Two-tailed unpaired Student's T-Test). D) CFC potential of definitive hematopoietic progenitors in WT, USB1 mutant and USB1 mutant_shPAPD5 cells (average+/−S.D., n=3 biological replicates). E) CFC potential of definitive hematopoietic progenitors in WT and USB1 mutant cells in treated with DMSO or RG7834 (0.5 μM) (average+/−S.D., n=3 biological replicates). F) Flow cytometry analysis of CD45+CD14-CD11b+CD16 cells following neutrophil differentiation (average+/−S.D., n=2 biological replicates). G) Model depicting the regulation of non-coding RNA stability through competition between 'Tailing' and 'Tail removing' enzymes. This system is analogous to the ubiquitin-mediated proteasome degradation system, where RNAs are tagged for degradation by 3' end modification by enzymes such as PAPD5 and PAPD7, and protector exonucleases such as PARN and USB1 remove the post-transcriptional modifications to stabilize the RNA. In the absence of tail removal, the 3' end modified RNA is degraded by 3' to 5' exonucleases such as EXOSC10.

FIG. 5A-F. A) Strategy for introduction of the disease-specific USB1 c.531delA mutation in hESCs. Guide RNA targeting exon 5 of USB1 was used in combination with specific single-strand DNA donor oligo templates. In blue, are silent mutations introduced to facilitate CRISPR/Cas9-mediated genome modification. B) Sequencing traces confirming genome modification. C) G-band karyotyping in WT and USB1 c.531delA hESCs D) EdU incorporation assay was performed in WT and USB1 c.531delA hESCs. The percentages of active proliferating cells (EdU+) are shown. E) Flow cytometry analysis for pluripotency markers in WT and USB1 c.531delA hESCs F) Telomere restriction fragment assays depicting telomere lengths in WT and USB1 c.531delA hESCs over multiple passages.

FIG. 7A-C. A) Bar plot indicates U6atac snRNA levels normalized to 5s rRNA (average+/−S.D., n=3 biological replicates). B) and C) Bar plot depicting U6atac snRNA genomic and oligoadenylated reads at indicated 3' ends (average+/−S.D., n=2 biological replicates, *P<0.05, Fisher's exact test).

FIG. 8A-E. A) Significantly enriched GO terms for DEGs in day 16 of CD34+CD45+ hematopoietic progenitors from USB1 mutant cells. B) Flow cytometry analysis for high SSC populations in WT and USB1 c.531delA cells following neutrophil development (average+/−S.D., n=2 biological replicates). C) Volcano plot depicting transcriptome changes in mature blood cells (day 30) in WT and USB1 c.531delA (Gray: unchanged; Magenta: differentially expressed). D) Venn diagram showing DEGs and differentially spliced genes in WT and USB1 c.531delA in undifferentiated hESCs or CD34+/CD45+ hematopoietic progenitors. E) KEGG pathway analysis of differentially expressed miRNAs in CD34+/CD45+ hematopoietic progenitors from USB1 mutant cells.

FIG. 9A-C. A) Gel image showing processing of 16-mer RNA substrates by wild-type USB1. Marker is a 7-nt RNA preceding the tail in each RNA substrate. B) Time-course measurement of USB1's activity on indicated RNA substrates. C) H208Q mutant USB1 has no activity on RNA substrates.

FIG. 10A-B. A) Relative PAPD5 mRNA levels in WT and USB1 c.531delA_shPAPD5 hESCs (average+/−S.D., n=3 biological replicates). (B) Flow cytometry analysis of CD45+ cells in WT and USB1 c.531delA CD34+/CD45+ cells treated with RG7834 (0.5 µM) (average+/−S.D., n=2 biological replicates).

Figure 1E:
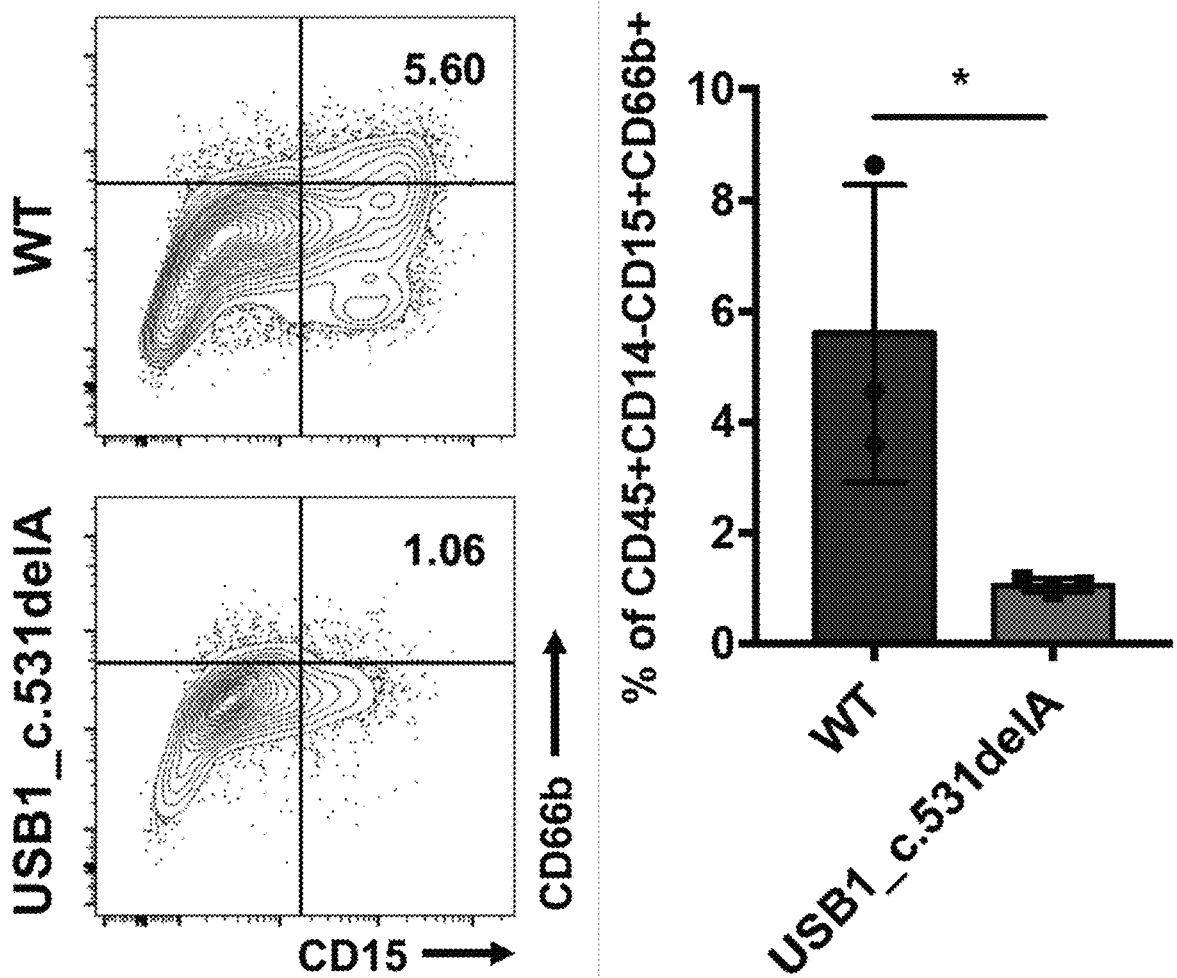

Applicant specifically incorporates by reference FIGS. 1-7, Examples 1-8, Table 1, and their accompany descriptions from U.S. Provisional Application No. 63/074,772.

DETAILED DESCRIPTION OF THE INVENTION

This invention described herein relates to a general system for regulating the degradation of ncRNAs that is based on the addition or removal of 3' oligo(A) or oligo(U) tails, which is directly analogous to the role of ubiquitination and deubiquitination in regulating the degradation of proteins (FIG. 4G). Enzymes that add 3' oligo(A) or oligo(U) tails, such as PAPD5, PAPD7, TUT4 and TUT7, are analogous to ubiquitination enzymes that promote the degradation of RNAs by targeting the 3' extended RNAs to robust 3' to 5' exonucleases such as DIS3L, DIS3L2 and the nuclear exosome. The present inventors demonstrate that USB1, in addition to the previously described PARN (23), functions as a second "de-tailing" enzyme, analogous to a deubiquitination enzyme, that protects miRNAs (and possibly other ncRNAs) from degradation. There is increasing evidence that miRNAs are modified at their 3' ends by the addition of uridines or adenosines depending on both complementarity to mRNA target and regulation of the miRNA precursor, and these modifications can lead to miRNA processing or degradation. Enzymes such as PARN and USB1 remove these post-transcriptional modifications and function as global regulators of miRNA stability. The loss of USB1's activity leads to a defect in miRNA regulation during hematopoiesis, leading to impaired hematopoiesis and neutropenia in patients. The present invention demonstrates a novel molecular mechanism of defective hematopoiesis caused by a loss of a conserved 3' to 5' RNA exonuclease USB1 and suggests that PAPD5/7 inhibitors could be therapeutically beneficial for these patients.

Another embodiment of the invention may include methods of treating a BMF condition, such as PN or DC in a subject and preferably a human subject. One preferred embodiment of the invention may include inhibiting the activity of USB1 in a subject in need thereof, wherein the inhibition of USB1 causes the downregulation of one or more downstream miRNAs. In another preferred embodiment, the invention may include downregulating the expression of usb1, wherein the downregulation of usb1 causes the downregulation of one or more downstream miRNAs.

Another embodiment of the invention may include methods of treating a BMF condition, such as PN or DC in a subject and preferably a human subject having a mutation in USB1 that causes downregulation of one or more downstream miRNAs, such as a homozygous or compound heterozygous mutations in the human gene C16orf57 encoding USB1. One preferred embodiment of the invention may include inhibiting the activity of PAPD5 and/or PAPD7 (generally referred to herein as PAPD5/7) wherein the inhibition of PAPD5/7 causes the upregulation of one or more downstream miRNAs. In another preferred embodiment, the invention may include inhibiting the expression of papd5 and/or papd7 (generally referred to herein as papd5/7) wherein the inhibition of papd5/7 causes the upregulation of one or more downstream miRNAs.

Another embodiment of the invention may include methods of treating a cancer in a subject and preferably a human subject. One preferred embodiment of the invention may include inhibiting the activity of USB1 wherein the inhibition of USB1 causes the down regulation of one or more downstream miRNAs. In another preferred embodiment, the invention may include inhibiting the expression of usb1 wherein the inhibition of usb1 causes the downregulation of one or more downstream miRNAs.

Another embodiment of the invention may include methods of treating a cancer in a subject and preferably a human subject having a mutation in USB1 that causes downregulation of one or more downstream miRNAs. One preferred embodiment of the invention may include inhibiting the activity of PAPD5 and/or PAPD7 (generally referred to herein as PAPD5/7) wherein the inhibition of PAPD5/7 causes the upregulation of one or more downstream miRNAs. In another preferred embodiment, the invention may include inhibiting the expression of papd5 and/or papd7 (generally referred to herein as papd5/7) wherein the inhibition of papd5/7 causes the upregulation of one or more downstream miRNAs.

Other embodiments of the invention may include methods of treating a BMF disease or condition, such as PN or DC by downregulating the expression of miR-125a-5p, miR-125b-5p, miR-199a-3p, miR-142-5p, miR-223-3p and miR-409-3p, in a subject in need thereof. In one preferred embodiment, this may be done through downregulating the expression of usb1, or inhibiting the activity of USB1, in a subject in need thereof.

Other embodiments of the invention may include methods of treating a BMF disease or condition, such as PN or DC by upregulating regulating the expression of miR-125a-5p, miR-125b-5p, miR-199a-3p, miR-142-5p, miR-223-3p and miR-409-3p, in a subject in need thereof, and preferably a human subject having a mutation in USB1 that causes downregulation of miR-125a-5p, miR-125b-5p, miR-199a-3p, miR-142-5p, miR-223-3p and miR-409-3p. In one preferred embodiment, this may be done through downregulating the expression of papd5/7, or inhibiting the activity of PAPD5/7, in a subject in need thereof.

Another embodiment of the invention may include methods of treating a disease or condition in a subject in need thereof, and preferably through the administration of a therapeutically effective amount of a USB1 inhibitor, wherein said USB1 inhibitor is a small-molecule inhibitor, small-inhibitory RNA (siRNA), short hairpin RNA (shRNA) (SEQ ID NO.s 6-8), bifunctional RNA, antisense oligonucleotide, anti-USB1 antibody or functional fragment thereof, ribozyme, deoxyribozyme, aptamer, small molecule or gene therapy that knocks out USB1. On one preferred embodiment, the USB1 inhibitor is a siRNA, shRNA, bifunctional RNA, antisense oligonucleotide, ribozyme, deoxyribozyme, or aptamer, and is further encoded by a nucleic acid. In yet additional embodiment, the USB1 inhibitor is administered to the subject via gene therapy.

Another embodiment of the invention may include methods of treating a disease or condition in a subject in need thereof, and preferably through the administration of a therapeutically effective amount of a PAPD5/7 inhibitor, wherein said PAPD5/7 inhibitor is a small-molecule inhibitor, small-inhibitory RNA (siRNA), short hairpin RNA (shRNA), bifunctional RNA, antisense oligonucleotide, anti-USB1 antibody or functional fragment thereof, ribozyme, deoxyribozyme, aptamer, small molecule or gene therapy that knocks out PAPD5/7. On one preferred embodiment, the PAPD5/7 inhibitor is a siRNA, shRNA, bifunctional RNA, antisense oligonucleotide, ribozyme, deoxyribozyme, or aptamer, and is further encoded by a nucleic acid. In yet additional embodiment, the PAPD5/7 inhibitor is administered to the subject via gene therapy. In one preferred embodiment, a PAPD5/7 inhibitor may include RG7834 (shown below).

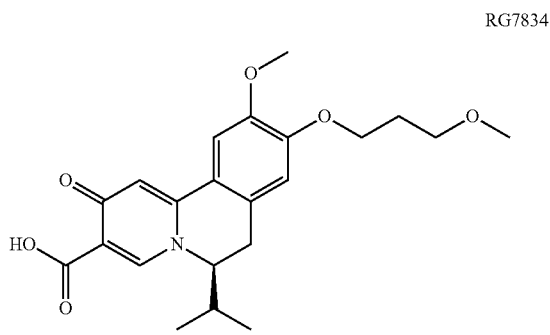 [SMILES: COCCCOc1cc2c(cc1OC)-c1cc(=O)c(C(=O)O)cn1[C@H](C(C)C)C2]

RG7834

Another embodiment of the invention may include methods of treating disease or condition in a subject in need thereof, preferably through the administration of a therapeutically effective amount of a USB1 inhibitor which may be co-administered with a different cancer therapy. In this preferred embodiment, the cancer therapy other than the USB1 inhibitor is radiotherapy, chemotherapy, surgery, immunotherapy, kinase inhibition, monoclonal antibody therapy, or a combination thereof.

Another embodiment of the invention may include methods of treating a disease or condition in a subject in need thereof, and preferably through the administration of a therapeutically effective amount of a PAPD5/7 inhibitor, wherein said PAPD5/7 inhibitor is a small-molecule inhibitor, small-inhibitory RNA (siRNA), short hairpin RNA (shRNA), bifunctional RNA, antisense oligonucleotide, anti-USB1 antibody or functional fragment thereof, ribozyme, deoxyribozyme, aptamer, small molecule or gene therapy that knocks out PAPD5/7. On one preferred embodiment, the PAPD5/7 inhibitor is a siRNA, shRNA, bifunctional RNA, antisense oligonucleotide, ribozyme, deoxyribozyme, or aptamer, and is further encoded by a nucleic acid. In yet additional embodiment, the USB1 inhibitor is administered to the subject via gene therapy.

Another embodiment of the invention may include methods of treating disease or condition in a subject in need thereof, preferably through the administration of a therapeutically effective amount of a PAPD5/7 inhibitor which may be co-administered with a different cancer therapy. In this preferred embodiment, the cancer therapy other than the PAPD5/7 inhibitor is radiotherapy, chemotherapy, surgery, immunotherapy, kinase inhibition, monoclonal antibody therapy, or a combination thereof. In one preferred embodiment, a PAPD5/7 inhibitor may include RG7834, which is co-administered with a different cancer therapy. In one preferred embodiment, a PAPD5/7 inhibitor may include RG7834.

In this preferred embodiment, the heterologous nucleic acid sequence expresses an RNA duplex, comprising a sense region and an antisense region, wherein the antisense region includes a plurality of contiguous nucleotides that are complementary to a USB1 (SEQ ID NO. 1) and/or PAPD5/7 (SEQ ID NO.'s 2-3) mRNA. In one embodiment, the polynucleotide encoding the siRNA comprises at least one nucleotide sequence configured to generate a hpRNA that targets one or more essential WSSV genes. In this preferred embodiment, such shRNA or hpRNAs may inhibit expression of target USB1 and/or PAPD5/7. It should be noted that the identification of a DNA sequence also includes the corresponding RNA sequence it encodes. As such, a reference to a SEQ ID NO. that includes DNA also specifically include the sequence of the RNA that it expresses as would be understood by one of ordinary skill in the art. A number of researchers have measured the binding energies of a large number of RNA duplex structures and have derived a set of rules which can be used to predict the secondary structure of RNA (see e.g Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerhead ribozyme compositions related to the targets of the invention.

The dsRNA oligonucleotides may be introduced into the cell by transfection with an heterologous target gene using carrier compositions such as liposomes, which are known in the art as described by the manufacturer for adherent cell lines. Transfection of dsRNA oligonucleotides for targeting endogenous genes may be carried out using Oligofectamine. Transfection efficiency may be checked using fluorescence microscopy for mammalian cell lines after co-transfection of hGFP-encoding pAD3 (Kehlenback et al. (1998) J Cell Biol 141: 863-74). The effectiveness of the RNAi may be assessed by any of a number of assays following introduction of the dsRNAs. These include Western blot analysis using antibodies which recognize the USB1 and/or PARP5/7 gene product following sufficient time for turnover of the endogenous pool after new protein synthesis is repressed, reverse transcriptase polymerase chain reaction and Northern blot analysis to determine the level of existing target mRNA, such as USB1 and/or PARP5/7. Further compositions, methods and applications of RNAi technology are provided in U.S. Pat. Nos. 6,278,039, 5,723,750 and 5,244,805, which are incorporated herein by reference.

Notably, where the invention claims that a heterologous inhibitory polynucleotide directed to the sequences from the group from consisting of: SEQ ID NO. 1, SEQ ID NO. 2, and/or SEQ ID NO. 3, such a claim may include the sequence of the DNA, mRNA and a corresponding inhibitory RNA molecule as one of ordinary skill could easily determine without undue experimentation.

Ribozyme molecules designed to catalytically cleave, for example USB1 and/or PARP5/7mRNA transcripts can also be used to prevent translation of subject mRNAs and/or expression of USB1 and/or PARP5/7 in multiple animal systems (see, e.g., PCT International Publication WO90111364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a USB1 and/or PARP5/7 mRNA, and the well-known catalytic sequence responsible for mRNA cleavage or a functionally equivalent sequence (see, e.g., U.S. Pat. No. 5,093,246, which is incorporated herein by reference in its entirety).

In addition to ribozymes that cleave mRNA at site specific recognition sequences, hammerhead ribozymes can also be used to destroy target mRNAs. Hammerhead ribozymes cleave mRNAs at locations dictated by flanking regions that form complementary base pairs with the target mRNA. Preferably, the target mRNA has the following sequence of two bases: 5'-mUG-3'. The construction and production of hammerhead ribozymes is well known in the art and is described more fully in Haseloff and Gerlach ((1988) Nature 334:585-591; and see PCT Appln. No. WO89/05852, the contents of which are incorporated herein by reference). Hammerhead ribozyme sequences can be embedded in a stable RNA such as a transfer RNm (tRNA) to increase cleavage efficiency in vivo (Perriman et al. (1995) Proc. Natl. Acad. Sci. mUSA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase HI-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617 27; Koseki et al. (1999) J Virol 73: 1868-77; Kuwabara et al. (1999) Proc Natl Acad Sci USA 96:m1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the C-terminal amino acid domains of, for example, long and short forms om target would allow the selective targeting of one or the other form of the target, and thus, have a selective effect on one form of the target gene product. Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a USB1 and/or PARP5/7 mRNA. In addition, ribozymes possess highly specific endoribonuclease activity, which autocatalytically cleaves the target sense mRNA.

The present invention extends to ribozymes which hybridize to a sense mRNA encoding a USB1 and/or PARP5/7 gene thereby hybridizing to the sense mRNA and cleaving it, such that it is no longer capable of being translated to synthesize a functional polypeptide product. Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation.

Because ribozymes, unlike antisense molecules, are catalytic, a lower intracellular concentration is required for efficiency. A further aspect of the invention relates to the use of the isolated "antisense" nucleic acids to inhibit expression, e.g., by inhibiting transcription and/or translation of a subject USB1 and/or PARP5/7 nucleic acids. The antisense nucleic acids may bind to the potential drug target by conventional base pair complementarity, or, for example, in the case of binding to DNA duplexes, through specific interactions in the major groove of the double helix. In general, these methods refer to the range of techniques generally employed in the art, and include any methods that rely on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a USB1 and/or PARP5/7 polypeptide. By "antisense," as used herein in reference to nucleic acids, is meant a nucleic acid sequence, regardless of length, that is complementary to the coding strand of a gene. By "binding to" a molecule is meant having a physicochemical affinity for that molecule. For example, an antibody molecule may have affinity for an epitope found in a target protein. As used herein, the term "antisense RNA" or "asRNA" refers to an RNAi agent that is a single stranded oligonucleotide, or protein-oligonucleotide. In a typical asRNA, the single strand is complementary to all or a part of the target mRNA, and preferably a USB1 and/or PARP5/7 mRNA. The complementarity of an asRNA may be with any part of the specific gene transcript, i.e., at the 5' non-coding sequence, 3' non-translated sequence, introns, or the coding sequence. asRNA may be introduced into a cell to inhibit translation of a complementary mRNA by base pairing to it and physically obstructing the translation machinery. Antisense RNA anneal to a complementary mRNA target sequence, and translation of the mRNA target sequence is disrupted as a result of steric hindrance of either ribosome access or ribosomal read through. The antisense RNA mechanism is different from RNA interference (RNAi), a related process in which double-stranded RNA fragments (dsRNA, also called small interfering RNAs (siRNAs)) trigger catalytically mediated gene silencing, most typically by targeting the RNA-induced silencing complex (RISC) to bind to and degrade the mRNA. Annealing of a strand of the asRNA molecule to mRNA or DNA can result in fast degradation of duplex RNA, hybrid RNA/DNA duplex, or duplex RNA resembling precursor tRNA by ribonucleases in the cell, or by cleavage of the target RNA by the antisense compound itself. Complementary sequences can be determined by one of ordinary skill in the art without undue experimentation.

Alternatively, the antisense construct is an oligonucleotide probe, which is generated ex vivo and which, when introduced into the cell causes inhibition of expression by hybridizing with the mRNA and/or genomic sequences of a USB1 and/or PARP5/7 nucleic acid. Such oligonucleotide probes are preferably modified oligonucleotides, which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches involve the design of oligonucleotides (either DNA or RNA) that are complementary to mRNA encoding a USB1 and/or PARP5/7 polypeptide. The antisense oligonucleotides may bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Oligonucleotides that are complementary to the 5' end of the mRNA, e.g., the 5'] untranslated sequence up to and including the AUG initiation codon, should work most efficiently at inhibiting translation. However, sequences complementary to the 3' untranslated sequences of mRNAs have been shown to be effective at inhibiting translation of mRNAs as well.

Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5',3' or coding region of mRNA, antisense nucleic acids should be at least six nucleotides in length, and are preferably less that about 100 and more preferably less than about 50, 25, 17 or 10 nucleotides in length.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or compounds facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89110134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to: 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N 6-isopentenyladenine, 1-methylguanine, III methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to: arabinose, 2-fluoroarabinose, xylulose, and hexose. The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

A further aspect of the invention relates to the use of DNA enzymes to inhibit expression of the usb1 and/or parp5/7 gene. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions. Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462. Similarly, methods of delivery of DNA ribozymes in vitro or in vivo include methods of delivery of RNA ribozyme, as outlined in detail above. Additionally, one of skill in the art will recognize that, like antisense oligonucleotide, DNA enzymes can be optionally modified to improve stability and improve resistance to degradation.

Antisense RNA and DNA, ribozyme, RNAi constructs of the invention may be prepared by any method known in the art for the synthesis of DNA and RNA molecules, including techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

In some embodiments, the agent is an aptamer. Aptamers are nucleic acid or peptide molecules that bind to a specific target molecule. Aptamers can inhibit the activity of the target molecule by binding to it.

A further aspect of the invention relates to the use of DNA editing compositions and methods to inhibit, alter, disrupt expression and/or replace one or more target genes. In various embodiments, one or more target genes may be altered through CRISPR/Cas-9, TALAN or Zinc (Zn2+) finger nuclease systems.

In some embodiments, the agent for altering gene expression is CRISPR-Cas9, or a functional equivalent thereof, together with an appropriate RNA molecule arranged to target one or more target genes, such as usb1, parp5/7 or any homolog/orthologs thereof. For example, one embodiment of the present invention may include the introduction of one or more guide RNAs (gRNAs) to be utilized by CRISPR/Cas9 system to disrupt, replace, or alter the expression or activity of one or more target genes.

In this context, the gene-editing CRISPR/cas-9 technology is an RNA-guided gene-editing platform that makes use of a bacterially derived protein (Cas9) and a synthetic guide RNA to introduce a double strand break at a specific location within the genome. Editing is achieved by transfecting a cell or a subject with the Cas9 protein along with a specially designed guide RNA (gRNA) that directs the cut through hybridization with its matching genomic sequence. By making use of this technology, it is possible to introduce specific genetic alterations in one or more target genes. In some embodiments, this CRISPR/cas-9 may be utilized to replace one or more existing wild-type genes with a modified version, while additional embodiments may include the addition of genetic elements that alter, reduce, increase or knock-out the expression of a target gene such as usb1, and/or parp5/7.

In some embodiments, the agent for altering gene expression is a zinc finger, or zinc finger nuclease or other equivalent. The term "zinc finger nuclease" or "zinc finger nuclease as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway.

Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo Colo. (May 1991). "Zinc finger-DNA recognition: crystal structure of a Zif268-DNA complex at 2.1 A". Science 252 (5007): 809-17, the entire contents of which are incorporated herein).

In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length.

Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". Cold Spring Harb. Symp. Quant. Biol. 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, Cys2His2, Gag knuckle, Treble clef, Zinc ribbon, Zn2/Cys6, and TAZ2 domain-like motifs (see, e.g., Krishna S S, Majumdar I, Grishin N V (January 2003). "Structural classification of zinc fingers: survey and summary". Nucleic Acids Res. 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant R A (2001). "Design and selection of novel cys2H is2 Zinc finger proteins". Annual Review of Biochemistry 70: 313-340; Jamieson A C, Miller J C, Pabo C O (2003). "Drug discovery with engineered zinc-finger proteins". Nature Reviews Drug Discovery 2 (5): 361-368; and Liu Q, Segal D J, Ghiara J B, Barbas C F (May 1997). "Design of polydactyl zinc-finger proteins for unique addressing within complex genomes". Proc. Natl. Acad. Sci. U.S.A. 94 (11); the entire contents of each of which are incorporated herein by reference).

Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

In some embodiments, the agent for altering the target gene is a TALEN system or its equivalent. The term TALEN or "Transcriptional Activator-Like Element Nuclease" or "TALE nuclease" as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et. al. (February 2011). "Efficient construction of sequence-specific TAL effectors for modulating mammalian transcription". Nature Biotechnology 29 (2): 149-53; Geibler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". Nucleic Acids Research; Morbitzer, R.; Elsaesser, J.; Hausner, J.; Lahaye, T. (2011). "Assembly of custom TALE-type DNA binding domains by modular cloning". Nucleic Acids Research; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". Nucleic Acids Research.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". PLoS ONE 6 (5): e19722; each of which is incorporated herein by reference).

Those of skill in the art will understand that TALE nucleases can be engineered to target virtually any genomic sequence with high specificity, and that such engineered nucleases can be used in embodiments of the present technology to manipulate the genome of a cell, e.g., by delivering the respective TALEN via a method or strategy disclosed herein under circumstances suitable for the TALEN to bind and cleave its target sequence within the genome of the cell. In some embodiments, the delivered TALEN targets a gene or allele associated with a disease or disorder or a biological process, such as PN, DC or cancer, or one or more target genes. In some embodiments, delivery of the TALEN to a subject confers a therapeutic benefit to the subject, such as reducing, ameliorating or eliminating PN, DC or cancer in a patient.

In some embodiments, the target gene of a cell, tissue, organ or organism is altered by a nuclease delivered to the cell via a strategy or method disclosed herein, e.g., CRISPR/cas-9, a TALEN, or a zinc-finger nuclease, or a plurality or combination of such nucleases. In some embodiments, a single- or double-strand break is introduced at a specific site within the genome by the nuclease, resulting in a disruption of the target genomic sequence.

In some embodiments, the target genomic sequence is a nucleic acid sequence within the coding region of a target gene. In some embodiments, the strand break introduced by the nuclease leads to a mutation within the target gene that impairs the expression of the encoded gene product. In some embodiments, a nucleic acid is co-delivered to the cell with the nuclease. In some embodiments, the nucleic acid comprises a sequence that is identical or homologous to a sequence adjacent to the nuclease target site. In some such embodiments, the strand break affected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of the undesired allele. In some embodiments, the nucleic acid is co-delivered by association to a supercharged protein. In some embodiments, the supercharged protein is also associated to the functional effector protein, e.g., the nuclease. In some embodiments, the delivery of a nuclease to a target cell results in a clinically or therapeutically beneficial alteration of the function of a gene.

In some embodiments, cells from a subject are obtained and a nuclease or other effector protein is delivered to the cells by a system or method provided herein ex vivo. In some embodiments, the treated cells are selected for those cells in which a desired nuclease-mediated genomic editing event has been affected. In some embodiments, treated cells carrying a desired genomic mutation or alteration are returned to the subject they were obtained from.

The present invention also encompasses reagents, compounds, agents or molecules which specifically bind the target molecules, such as USB1 and/or PARP5/7, whether they be polypeptides or polynucleotides. As used herein, the term "specifically binding," refers to the interaction between binding pairs (e.g., an antibody and an antigen or aptamer and its target). In some embodiments, the interaction has an affinity constant of at most $10^{-6}$ moles/liter, at most $10^{-7}$ moles/liter, or at most $10^{-8}$ moles/liter. In other embodiments, the phrase "specifically binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

The molecules that may bind to one or more of the inventions targets include antibodies, aptamers and antibody derivatives or fragments. As used herein, the term "antibody" refers to an immunoglobulin molecule capable of binding an epitope present on an antigen. The term is intended to encompass not only intact immunoglobulin molecules such as monoclonal and polyclonal antibodies, but also bi-specific antibodies, humanized antibodies, chimeric antibodies, anti-idiopathic (anti-ID) antibodies, single-chain antibodies, Fab fragments, F(ab') fragments, fusion proteins and any modifications of the foregoing that comprise an antigen recognition site of the required specificity.

As used herein, an aptamer is a non-naturally occurring nucleic acid molecule or peptide having a desirable action on a target, including, but not limited to, binding of the target, catalytically changing the target, reacting with the target in a way which modifies/alters the target or the functional activity of the target, covalently attaching to the target as in a suicide inhibitor, facilitating the reaction between the target and another molecule. In one embodiment, the antibodies, antibody derivatives or fragments, or aptamers specifically bind to a component that is a fragment, modification, precursor or successor of one or more target molecules.

Another aspect of the invention provides compositions comprising the target molecules, a binding molecule that is specific for the target (e.g., an antibody or an aptamer), an inhibitor of the target, or other molecule that can increase or decrease the level or activity of the target molecule, such USB1 and/or PARP5/7, through the administration of RG7834, or an analog thereof. Such compositions may be pharmaceutical compositions formulated for use as a therapeutic. Alternatively, the invention provides a composition that comprises a component that is a fragment, modification, precursor, or successor of a target molecule that comprises a foregoing component. In another embodiment, the invention provides a composition that comprises an antibody or aptamer that specifically binds to a target polypeptide or a molecule that comprises a foregoing antibody or aptamer. In some embodiments, the level of the target molecules may be determined using a standard immunoassay, such as sandwiched ELISA using matched antibody pairs and chemiluminescent detection. Notably, anti-protein/anti-peptide antisera or monoclonal antibodies can be made by standard protocols.

Definitions

As used herein and in the appended claims, the singular forms "a", "and", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth.

The term "gene" is meant to refer to a segment of nucleic acid that contains the information necessary to produce a functional RNA product. A gene usually contains regulatory regions dictating under what conditions the RNA product is made, transcribed regions dictating the sequence of the RNA product, and/or other functional sequence regions. A gene may be transcribed to produce an mRNA molecule, which contains the information necessary for translation into the amino acid sequence of the resulting protein.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "dyskeratosis congenita" or "DC" is meant to refer to a hereditary disorder with features that include, but are not limited to, cutaneous pigmentation, dystrophy of the nails, leukoplakia of the oral mucosa and low blood counts.

The term "poikiloderma with neutropenia" or "PN" is an autosomal recessive syndrome characterized by poikiloderma, hyperkeratotic nails, generalized hyperkeratosis on palms and soles, noncyclic neutropenia, short stature, and recurrent pulmonary infections The term "compound" or "composition" "a compound of the invention" includes all solvates, complexes, polymorphs, radiolabeled derivatives, tautomers, stereoisomers, and optical isomers of compounds that inhibit USB1 or PAPD5/7. For example, the invention includes all solvates, complexes, polymorphs, radiolabeled derivatives, tautomers, stereoisomers, and optical isomers of the PAPD5/7 inhibitor compound RG7834 generally described herein, and salts thereof, unless otherwise specified.

The term "microRNA" or "miRNA" means small double stranded RNA that regulates the expression of target messenger RNAs either by mRNA cleavage, translational repression/inhibition or heterochromatic silencing.

As used herein, "inhibits," "inhibition" refers to the decrease relative to the normal wild-type level, or control level. Inhibition may result in a decrease, for example of miRNA expression, and in particular expression of miR-125a-5p, miR-125b-5p, miR-199a-3p, miR-142-5p, miR-223-3p and miR-409-3p, in response inhibition of USB1 by less than 10%, 10%, 15%, 20%, 25%, 30%, 35%, 40%, 45%, 50%, 55%, 60%, 65%, 70%, 75%, 80%, 85%, 90%, 95% or 100%. Inhibition may result in a decrease, for example of USB1 or PAPD5/7 activity by less than 10%, 10%, 15%, 20%, 25%, 30%, 35%, 40%, 45%, 50%, 55%, 60%, 65%, 70%, 75%, 80%, 85%, 90%, 95% or 100%.

As used herein, "increase," "enhance" refers to the increase relative to the normal wild-type level, or control level. Increasing may result in an increase, for example of miRNA expression, and in particular expression of miR-125a-5p, miR-125b-5p, miR-199a-3p, miR-142-5p, miR-223-3p and miR-409-3p, in response inhibition of PAPD5/7, for example by RG7834, less than 10%, 10%, 15%, 20%, 25%, 30%, 35%, 40%, 45%, 50%, 55%, 60%, 65%, 70%, 75%, 80%, 85%, 90%, 95% or 100% or more. In another embodiment, the inventive technology includes one or more pharmaceutical compositions that may include a therapeutically effective amount of RG7834.

"Pharmaceutical compositions" are compositions that include an amount (for example, a unit dosage) of the disclosed compound(s) together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition). In another embodiment, a compound of the invention, and preferably RG7834 or an inhibitor of USB1 or PAPD5/7 may be in the form of a pharmaceutically acceptable salt or ester. The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

By "cancer" is meant a disease characterized by the pathological proliferation of a cell or tissue and its subsequent migration to or invasion of other tissues or organs. Cancer growth is typically uncontrolled and progressive, and occurs under conditions that would not elicit, or would cause cessation of, multiplication of normal cells. Cancers can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Non-limiting examples of cancers include: acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

By "chemotherapeutic agent" is meant one or more chemical agents used in the treatment or control of proliferative diseases (e.g., cancer). Chemotherapeutic agents include cytotoxic and cytostatic agents. Exemplary chemotherapeutic agents may mediate DNA damage (e.g., alkylating chemotherapeutic agents). Non-limiting examples of chemotherapeutic agents are generally known in the art.

A "therapeutically effective amount" of the disclosed compound, which may preferably be RG7834, is a dosage of the compound that is sufficient to achieve a desired therapeutic effect, such as inhibition of or USB1 and/or PAPD5/7, or regulate expression of miR-125a-5p, miR-125b-5p, miR-199a-3p, miR-142-5p, miR-223-3p and miR-409-3p, or treatment of a disease or disorder such as PN or DC. In some examples, a therapeutically effective amount is an amount sufficient to achieve tissue concentrations at the site of action that are similar to those that are shown to inhibit USB1 or PAPD5/7 expression or activity in tissue culture, in vitro, or in vivo. In some examples, a therapeutically effective amount is an amount sufficient to achieve tissue concentrations at the site of action that are similar to those that are shown to modulate expression of miR-125a-5p, miR-125b-5p, miR-199a-3p, miR-142-5p, miR-223-3p and miR-409-3p in tissue culture, in vitro, or in vivo. For example, a therapeutically effective amount of a compound of the invention, such as RG7834, may be such that the subject receives a dosage of less than or about 0.1 μg/kg body weight/day to about 1000 mg/kg body weight/day, for example, a dosage of about 1 μg/kg body weight/day to about 1000 μg/kg body weight/day, such as a dosage of about 5 μg/kg body weight/day to about 500 μg/kg body weight/day, or more.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

By "levels" or "expression" is meant the amount of a protein or RNA present in a cell (e.g., a cancer cell or a control cell).

By "USB1 protein" is meant a protein that is substantially identical to all or a part of any one of SEQ ID NO. 1, or a fragment or variant thereof. By "USB1 mRNA" is meant an mRNA that encodes a protein that is substantially identical to all or a part of SEQ ID NO. 1, or a homolog thereof. By "usb1 gene" is meant an nucleotide sequence that encodes a protein that is substantially identical to all or a part of SEQ ID NO. 1, or a homolog thereof.

By "PAPD5 protein" is meant a protein that is substantially identical to all or a part of any one of SEQ ID NO. 2, or a fragment or variant thereof. By "PAPD5 mRNA" is meant an mRNA that encodes a protein that is substantially identical to all or a part of SEQ ID NO. 2, or a homolog thereof. By "padp5 gene" is meant an nucleotide sequence that encodes a protein that is substantially identical to all or a part of SEQ ID NO. 2, or a homolog thereof.

By "PAPD7 protein" is meant a protein that is substantially identical to all or a part of any one of SEQ ID NO. 3, or a fragment or variant thereof. By "PAPD7 mRNA" is meant an mRNA that encodes a protein that is substantially identical to all or a part of SEQ ID NO. 3, or a homolog thereof. By "padp7 gene" is meant an nucleotide sequence that encodes a protein that is substantially identical to all or a part of SEQ ID NO. 3, or a homolog thereof.

By "activity" is meant an activity of molecules, such as a protein in a cell. Non-limiting examples of USB1 activity, or PAPD5/7 activity.

By "RNA interference" (RNAi) is meant a phenomenon where double-stranded RNA homologous to a target mRNA leads to degradation of the targeted mRNA (e.g., a USB1 mRNA). RNAi is more broadly defined as degradation of target mRNAs by homologous siRNAs. By "siNA" is meant small interfering nucleic acids. One exemplary siNA is composed of ribonucleic acid (siRNA). siRNAs can be 21-25 nt RNAs derived from processing of linear double-stranded RNA. siRNAs assemble in complexes termed RISC (RNA-induced silencing complex) and target homologous RNA sequences for endonucleolytic cleavage. Synthetic siRNAs also recruit RISCs and are capable of cleaving homologous RNA sequences.

The terms "individual," "subject," and "patient," used interchangeably herein, refer to a mammal, including, but not limited to, murines, simians, humans, mammalian farm animals, mammalian sport animals, and mammalian pets. Preferably, the subject herein is human. As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

By "treating" a disease, disorder, or condition is meant delaying an initial or subsequent occurrence of a disease, disorder, or condition; increasing the disease-free survival time between the disappearance of a condition and its reoccurrence; stabilizing or reducing one or more (e.g., two, three, four, or five) adverse symptom(s) associated with a condition; or inhibiting, slowing, or stabilizing the progression of a condition. The term "treating" also includes reducing (e.g., by at least 5%, 10%, 15%, 20%, 25%, 30%, 35%, 40%, 45%, 50%, 55%, 60%, 65%, 70%, 75%, 80%, 85%, 90%, or 95% the severity or duration of one or more (e.g., one, two, three, four, or five) symptoms of a disease (e.g., cancer) in a patient. Desirably, at least 20%, 40%, 60%, 80%, 90%, or 95% of the treated subjects have a complete remission in which all evidence of the disease disappears. In another desirable embodiment, the length of time a patient survives after being diagnosed with a condition and treated using the methods of the invention is at least 20%, 40%, 60%, 80%, 100%, 200%, or even 500% greater than (i) the average amount of time an untreated patient survives or (ii) the average amount of time a patient treated with another therapy survives.

Such pharmaceutical compositions/formulations are useful for administration to a subject, in vivo or ex vivo. Pharmaceutical compositions and formulations include carriers or excipients for administration to a subject. As used herein the terms "pharmaceutically acceptable" and "physiologically acceptable" mean a biologically compatible formulation, gaseous, liquid, or solid, or mixture thereof, which is suitable for one or more routes of administration, in vivo delivery, or contact. Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules, and crystals. Supplementary active compounds (e.g., preservatives, antibacterial, antiviral, and antifungal agents) can also be incorporated into the compositions. The formulations may, for convenience, be prepared or provided as a unit dosage form. In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein.

In certain embodiment, a "pharmaceutically acceptable carrier" includes a "pharmaceutically acceptable salt" which refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylene-sulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable salts include inorganic acids such as hydrochloric acid, hydrobromic acid, sulfuric acid, and phosphoric acid; and organic acids such as oxalic acid, maleic acid, succinic acid, and citric acid. "Basic addition salts" refer to salts derived from appropriate bases, these salts including alkali metal, alkaline earth metal, and quaternary amine salts. Hence, the present invention contemplates sodium, potassium, magnesium, and calcium salts of the compounds disclosed herein, and the like. Basic addition salts can be prepared during the final isolation and purification of the compounds, often by reacting a carboxyl group with a suitable base such as the hydroxide, carbonate, or bicarbonate of a metal cation or with ammonia or an organic primary, secondary, or tertiary amine. The cations of therapeutically acceptable salts include lithium, sodium (by using, e.g., NaOH), potassium (by using, e.g., KOH), calcium (by using, e.g., Ca(OH)2), magnesium (by using, e.g., Mg(OH)2 and magnesium acetate), zinc, (by using, e.g., Zn(OH)2 and zinc acetate), and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N,N'-dibenzylethylenediamine, N,N'-diethylethanolamine, N,N'-dimethylethanolamine, triethanolamine, and tromethamine. Basic amino acids (e.g., 1-glycine and 1-arginine) and amino acids which may be zwitterionic at neutral pH (e.g., betaine (N,N,N-trimethylglycine)) are also contemplated.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone. Supplementary active compounds (e.g., preservatives, antioxidants, antimicrobial agents including biocides and biostats such as antibacterial, antiviral, and antifungal agents) can also be incorporated into the compositions. Preservatives and other additives include, for example, antimicrobials, anti-oxidants, chelating agents, and inert gases (e.g., nitrogen). Pharmaceutical compositions may therefore include preservatives, antimicrobial agents, anti-oxidants, chelating agents, and inert gases.

Preservatives can be used to inhibit microbial growth or increase stability of the active ingredient thereby prolonging the shelf life of the pharmaceutical formulation. Suitable preservatives are known in the art and include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins.

Pharmaceutical compositions can optionally be formulated to be compatible with a particular route of administration. Exemplary routes of administration include administration to a biological fluid, an immune cell (e.g., T or B cell) or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis). Thus, pharmaceutical compositions include carriers (excipients, diluents, vehicles, or filling agents) suitable for administration to any cell, tissue, or organ, in vivo, ex vivo (e.g., tissue or organ transplant) or in vitro, by various routes and delivery, locally, regionally, or systemically.

Exemplary routes of administration for contact or in vivo delivery of a USB1 and/or PAPD5/7 inhibitor, such as RG7834, is a dosage of the compound that is sufficient to achieve a desired therapeutic effect, such as can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, and intralymphatic.

Formulations suitable for parenteral administration include aqueous and non-aqueous solutions, suspensions, or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable, or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be presented in unit-dose or multi-dose kits, for example, ampules and vials, and may be stored in a freeze-dried (lyophilized) condition requiring addition of a sterile liquid carrier, for example, water for injections, prior to use.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils, or creams as generally known in the art.

For topical administration, for example, to skin, pharmaceutical compositions typically include ointments, creams, lotions, pastes, gels, sprays, aerosols, or oils. Carriers which may be used include Vaseline, lanolin, polyethylene glycols, alcohols, transdermal enhancers, and combinations thereof. An exemplary topical delivery system is a transdermal patch containing an active ingredient. For oral administration, pharmaceutical compositions include capsules, cachets, lozenges, tablets, or troches, as powder or granules. Oral administration formulations also include a solution or a suspension (e.g., aqueous liquid or a non-aqueous liquid; or as an oil-in-water liquid emulsion or a water-in-oil emulsion). For airway or nasal administration, pharmaceutical compositions can be formulated in a dry powder for delivery, such as a fine or a coarse powder having a particle size, for example, in the range of 20 to 500 microns which is administered in the manner by inhalation through the airways or nasal passage. Depending on delivery device efficiency, effective dry powder dosage levels typically fall in the range of about 10 to about 100 mg. Appropriate formulations, wherein the carrier is a liquid, for administration, as for example, a nasal spray or as nasal drops, include aqueous or oily solutions of the active ingredient.

For airway or nasal administration, aerosol and spray delivery systems and devices, also referred to as "aerosol generators" and "spray generators," such as metered dose inhalers (MDI), nebulizers (ultrasonic, electronic, and other nebulizers), nasal sprayers and dry powder inhalers can be used. MDIs typically include an actuator, a metering valve, and a container that holds a suspension or solution, propellant, and surfactant (e.g., oleic acid, sorbitan trioleate, lecithin). Activation of the actuator causes a predetermined amount to be dispensed from the container in the form of an aerosol, which is inhaled by the subject. MDIs typically use liquid propellant and typically, MDIs create droplets that are 15 to 30 microns in diameter, optimized to deliver doses of 1 microgram to 10 mg of a therapeutic. Nebulizers are devices that turn medication into a fine mist inhalable by a subject through a face mask that covers the mouth and nose. Nebulizers provide small droplets and high mass output for delivery to upper and lower respiratory airways. Typically, nebulizers create droplets down to about 1 micron in diameter.

Dry-powder inhalers (DPI) can be used to deliver the compounds of the invention, either alone or in combination with a pharmaceutically acceptable carrier. DPIs deliver active ingredient to airways and lungs while the subject inhales through the device. DPIs typically do not contain propellants or other ingredients, only medication, but may optionally include other components. DPIs are typically breath-activated but may involve air or gas pressure to assist delivery.

Pharmaceutical formulations and delivery systems appropriate for the compositions and methods of the invention are known in the art (see, e.g., Remington: The Science and Practice of Pharmacy (2003) 20.sup.th ed., Mack Publishing Co., Easton, Pa.; Remington's Pharmaceutical Sciences (1990) 18.sup.th ed., Mack Publishing Co., Easton, Pa.; The Merck Index (1996) 12.sup.th ed., Merck Publishing Group, Whitehouse, N.J.; Pharmaceutical Principles of Solid Dosage Forms (1993), Technomic Publishing Co., Inc., Lancaster, Pa.; Ansel and Stoklosa, Pharmaceutical Calculations (2001) 11.sup.th ed., Lippincott Williams & Wilkins, Baltimore, Md.; and Poznansky et al., Drug Delivery Systems (1980), R. L. Juliano, ed., Oxford, N.Y., pp. 253-315).

In the methods of the invention, a USB1 and/or PAPD5/7 inhibitor, such as RG7834, may be administered in accordance with the methods at any frequency as a single bolus or multiple dose e.g., one, two, three, four, five, or more times hourly, daily, weekly, monthly or annually or between about 1 to 10 days, weeks, months, or for as long as appropriate. Exemplary frequencies are typically from 1-7 times, 1-5 times, 1-3 times, 2-times or once, daily, weekly, or monthly. Timing of contact, administration ex vivo or in vivo delivery can be dictated by the pathogenesis, symptom, pathology, or adverse side effect to be treated. For example, an amount can be administered to the subject substantially contemporaneously with, or within about 1-60 minutes or hours of the onset of a symptom or adverse side effect of treatment.

Doses may vary depending upon whether the treatment is therapeutic or prophylactic, the onset, progression, severity, frequency, duration, probability of or susceptibility of the symptom, the type of pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the pathology or symptom, or any adverse side effects of the treatment or therapy. The skilled artisan will appreciate the factors that may influence the dosage, frequency and timing required to provide an amount sufficient or effective for providing a prophylactic or therapeutic effect or benefit.

Doses can be based upon current existing treatment protocols, empirically determined, determined using animal disease models or optionally in human clinical studies. A subject may be administered in single bolus or in divided/metered doses, which can be adjusted to be more or less according to the various consideration set forth herein and known in the art. Dose amount, frequency or duration may be increased or reduced, as indicated by the status of pathogenesis, associated symptom or pathology, or any adverse side effect(s). For example, once control or a particular endpoint is achieved, for example, reducing, decreasing, inhibiting, ameliorating, or preventing onset, severity, duration, progression, frequency, or probability of one or more symptoms associated with a telomere-associated disease or disorder. Another embodiment of this disclosure provides pharmaceutical kits containing a pharmaceutical composition of this disclosure containing a USB1 and/or PAPD5/7 inhibitor such as preferably RG7834, prescribing information for the composition, and a container.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

Each publication or patent cited herein is incorporated herein by reference in its entirety.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1: The Role of USB1 in Disease Propagation

Figure 5D:
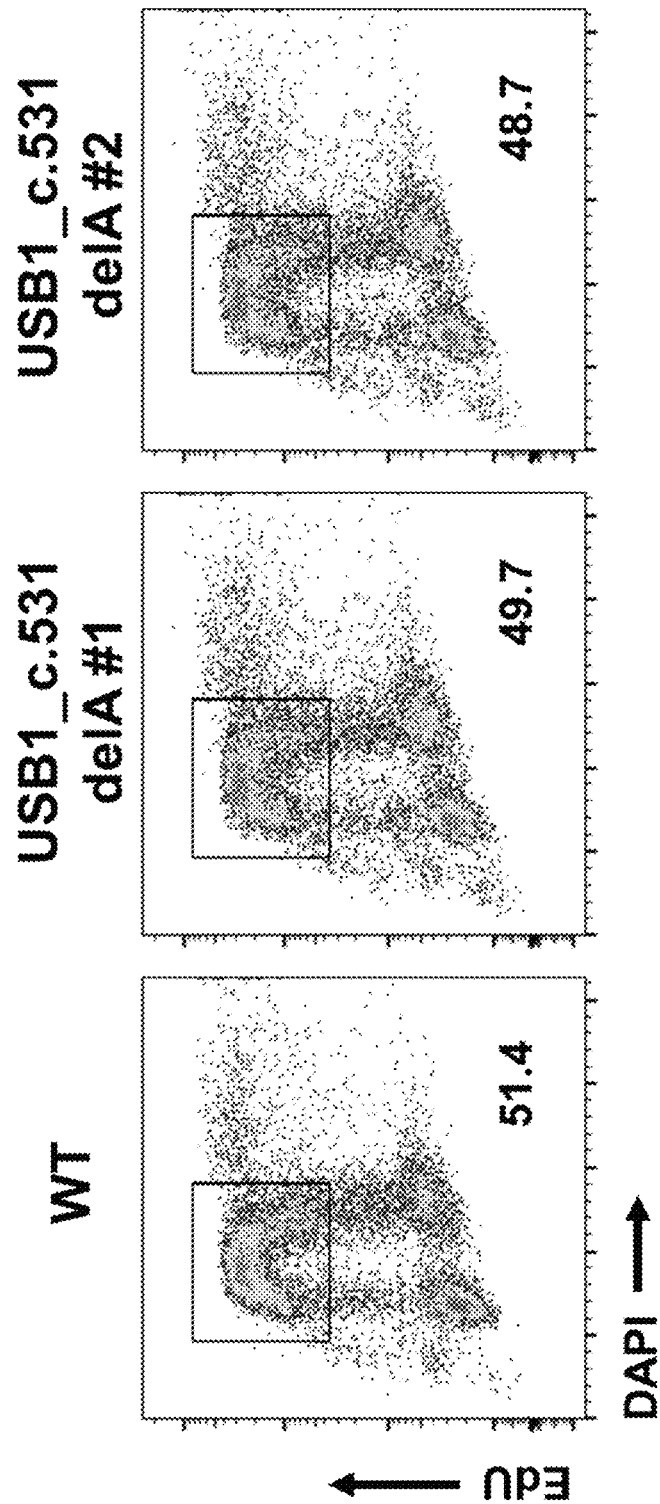

To investigate the role of USB1 in a physiological context, the present inventors utilized CRISPR/Cas9 to create human embryonic stem cells (hESCs) containing a frequently occurring c.531_del_A loss of-function mutation in the USB1 gene (hereafter referred to as USB1 mutant) (FIG. 5A-B). These USB1 mutant hESCs have normal karyotype (FIG. 5C), normal growth rate (FIG. 5D), are pluripotent (FIG. 5E) and have normal telomere length (FIG. 5F), indicating that a clinically-relevant USB1 mutation is not deleterious in undifferentiated hESCs.

Example 2: USB1 Required for Hematopoietic Differentiation

Figure 5E:
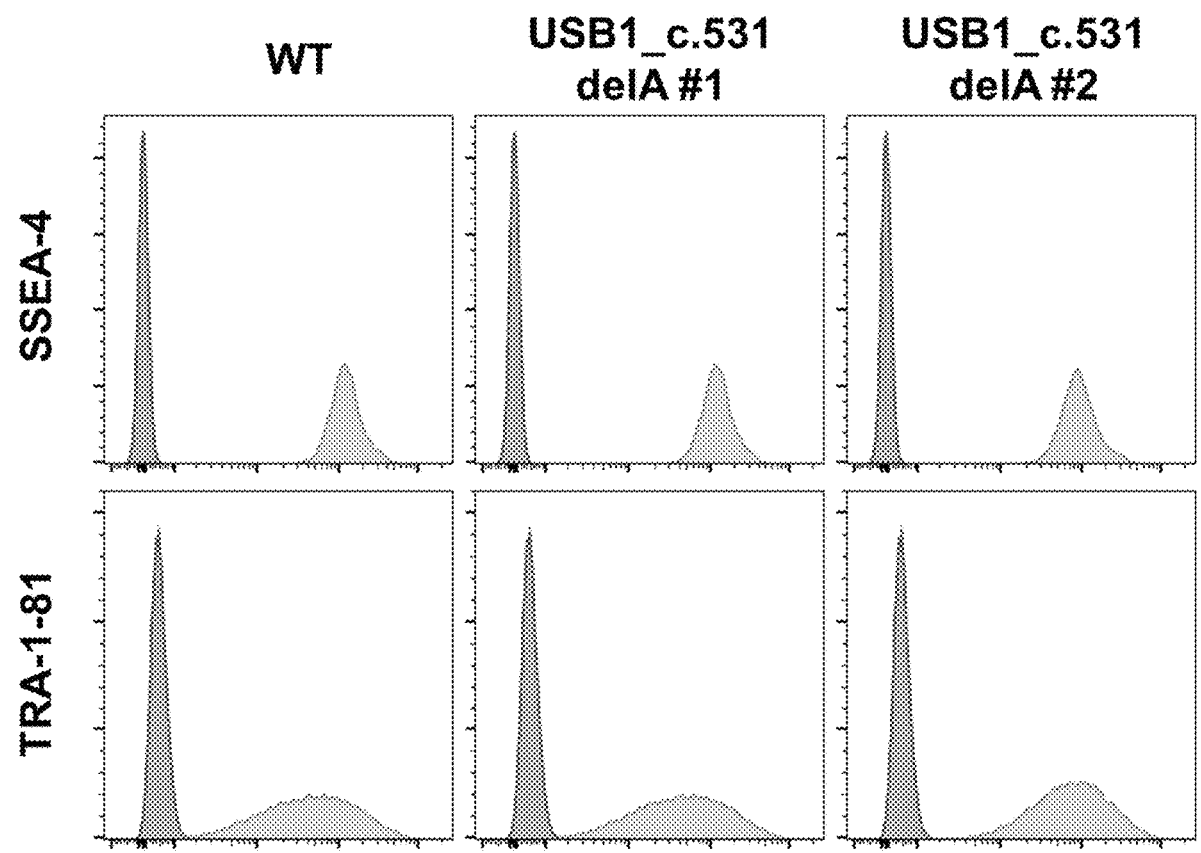
Figure 5F:
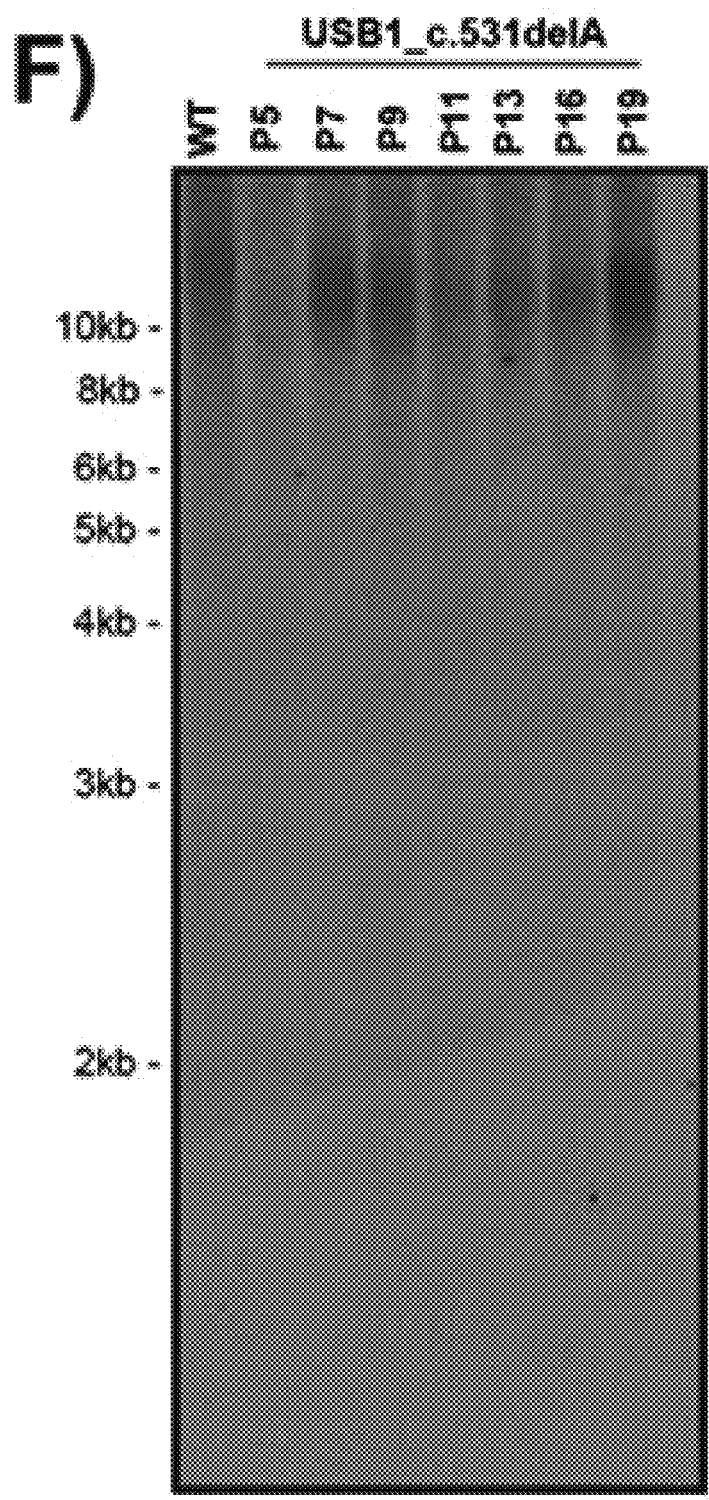
Figure 6A:
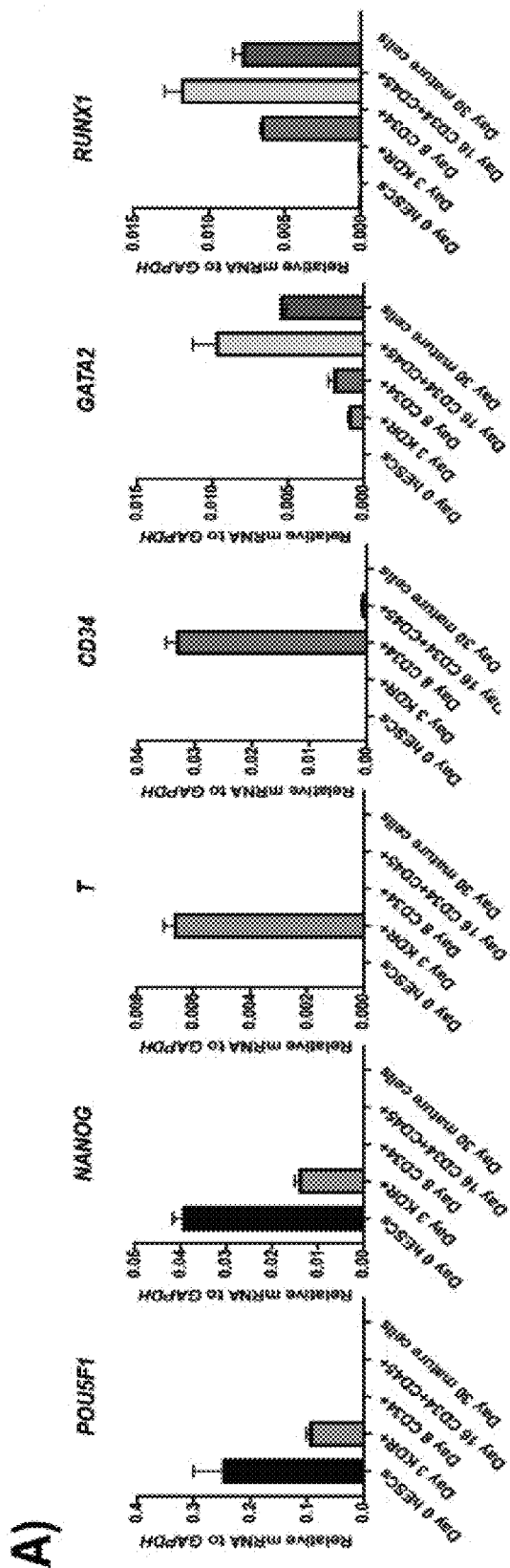
FIG. 6A-I. A) mRNA levels during definitive hematopoietic specification (average+/−S.D., n=3 biological replicates). Specific genes are indicated in each panel. B) and C) Flow cytometry analysis of CD235a and KDR from day 3 of primitive (B) or definitive (C) hematopoietic differentiation (average+/−S.D., n=4 biological replicates). D) and E) Flow cytometry analysis of CD34 and CD43 from day 8 of primitive (D) or definitive (E) hematopoietic differentiation (average+/−S.D., n=5 biological replicates). F) Representative flow cytometry analysis of CD45+ populations obtained from day 16 of hematopoietic differentiation (average+/−S.D., n=4 biological replicates) G) CFC potential of primitive hematopoietic progenitors in USB1 c.531delA (average+/−S.D., n=3 biological replicates) H) Blood neutrophils were quantified (left panel) in high SSC populations (right panel) using a clinical hematology analyzer (Hemavet). I) USB1 mRNA (left panel) or protein (right panel) levels were assessed in iUSB1-WT/c.531delA hESCs upon Dox treatment in a dose-dependent manner (average+/−S.D., n=3 biological replicates).
Figure 6B:
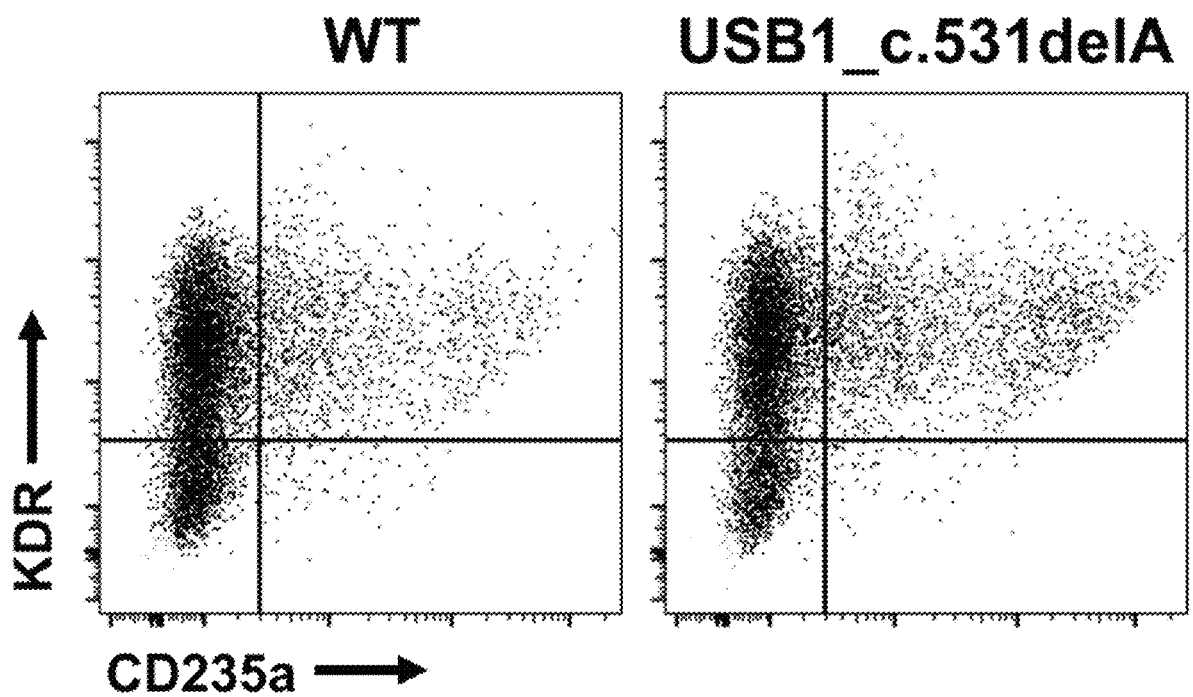
Figure 6B:
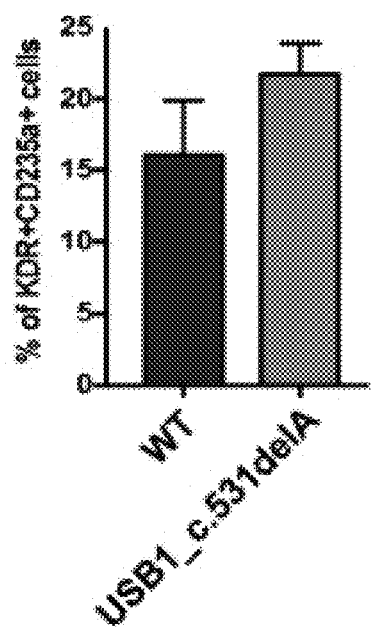
Figure 6C:
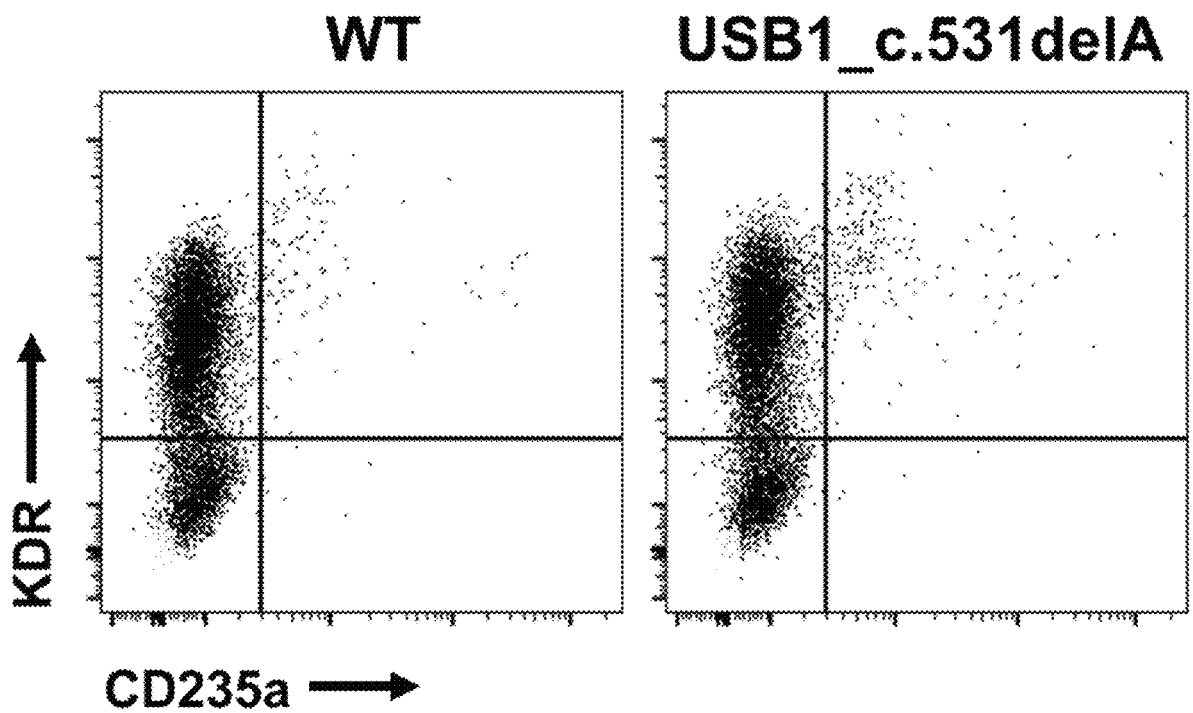
Figure 6C:
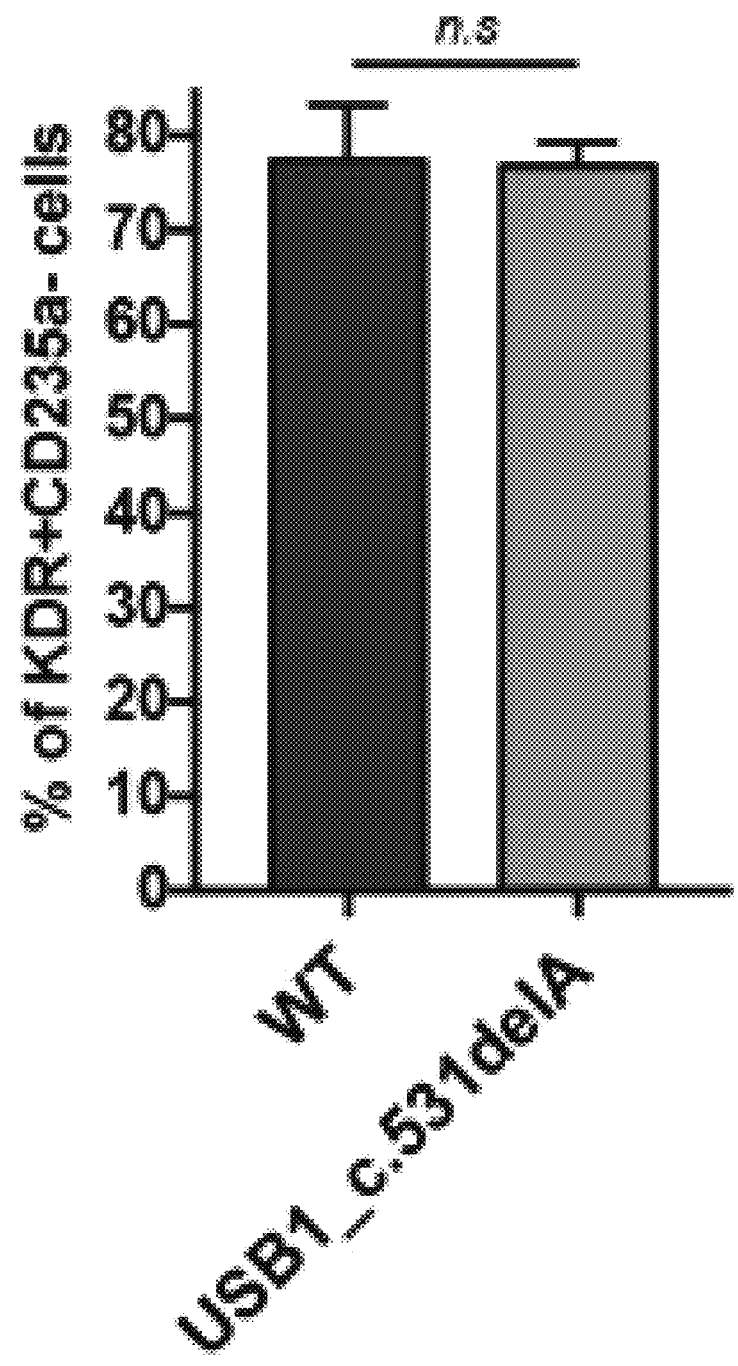
Figure 6D:
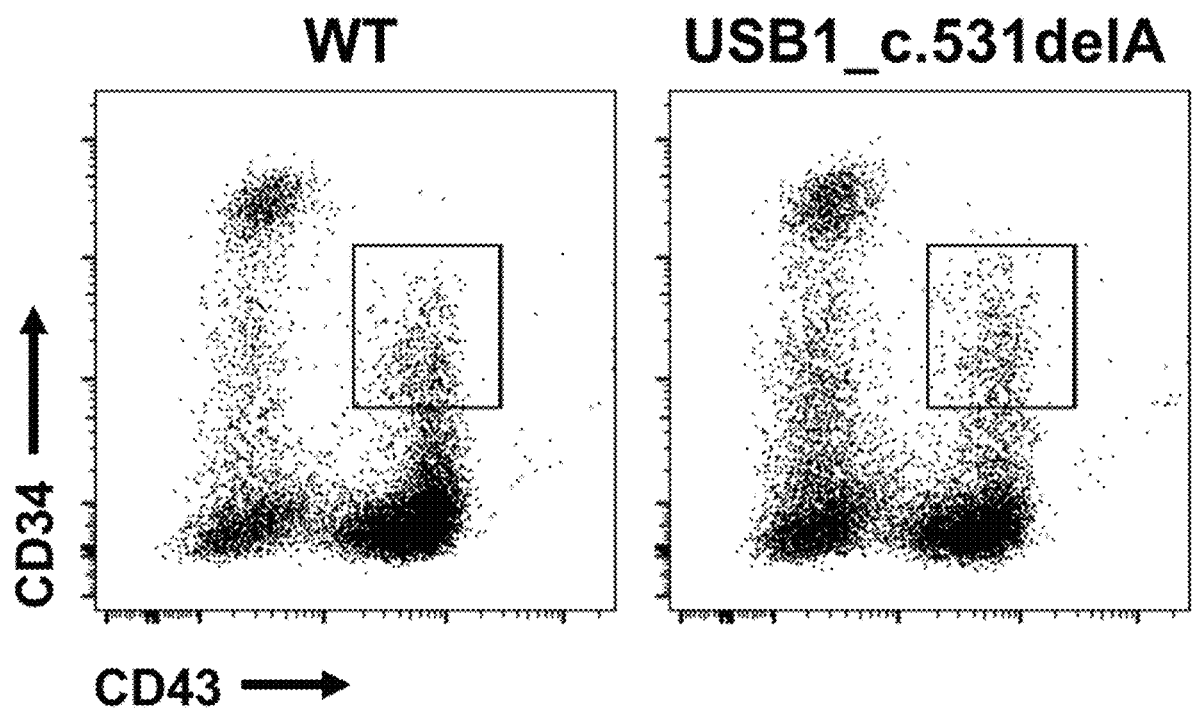
Figure 6D:
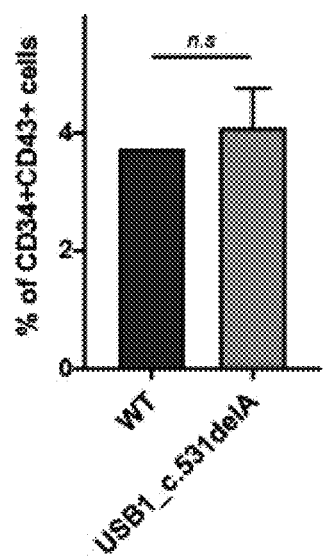
Figure 6E:
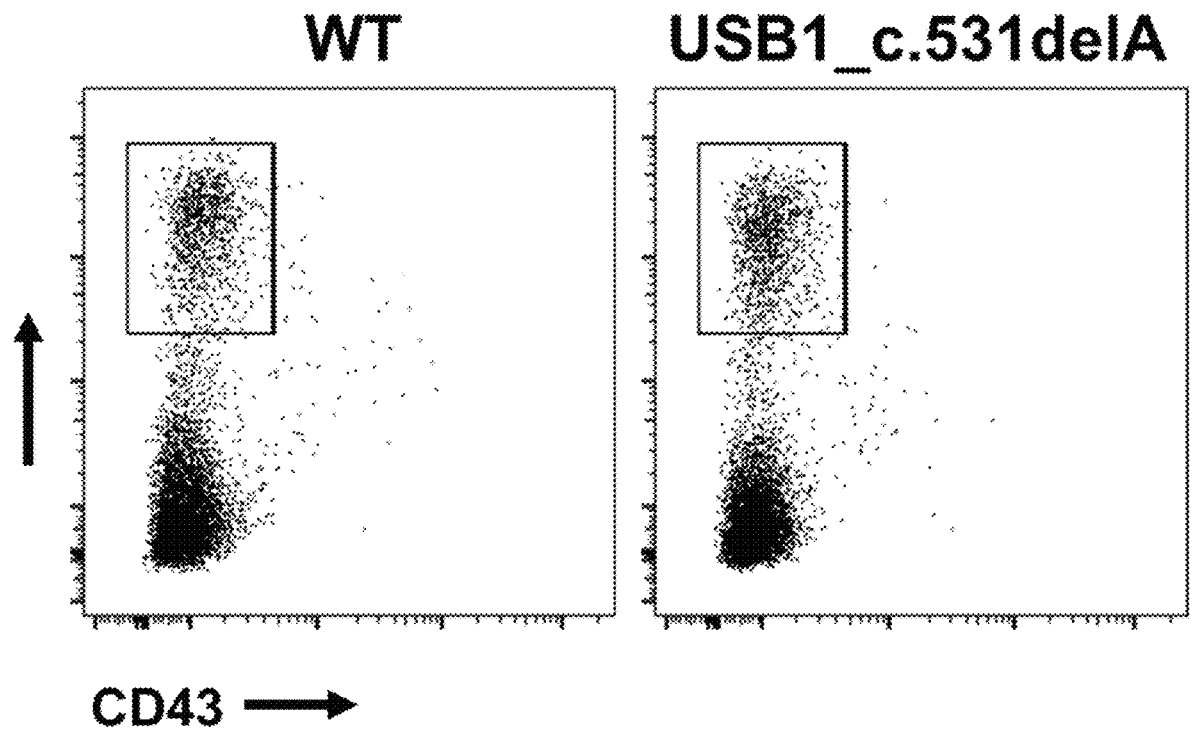
Figure 6E:
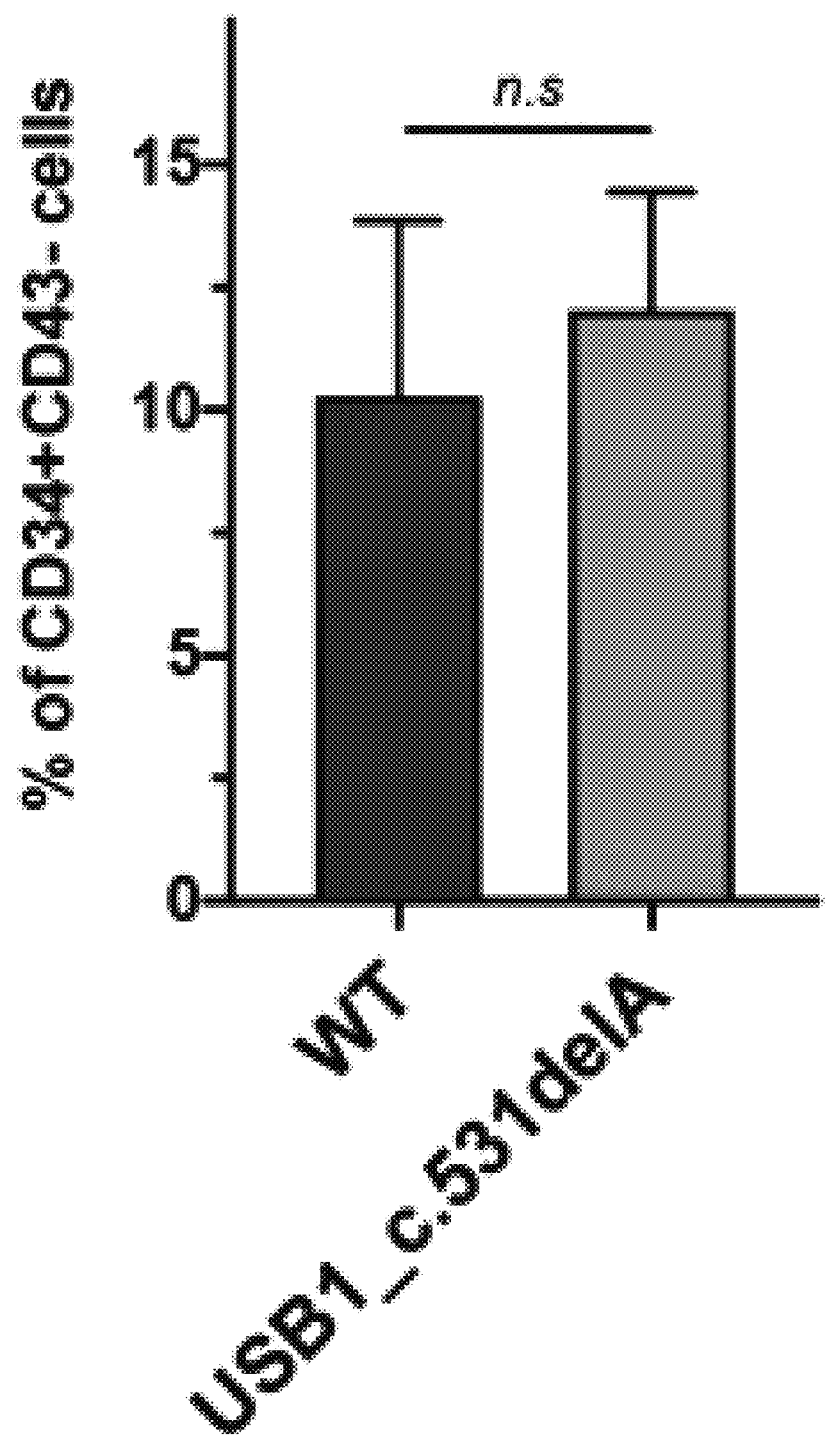
Figure 6F:
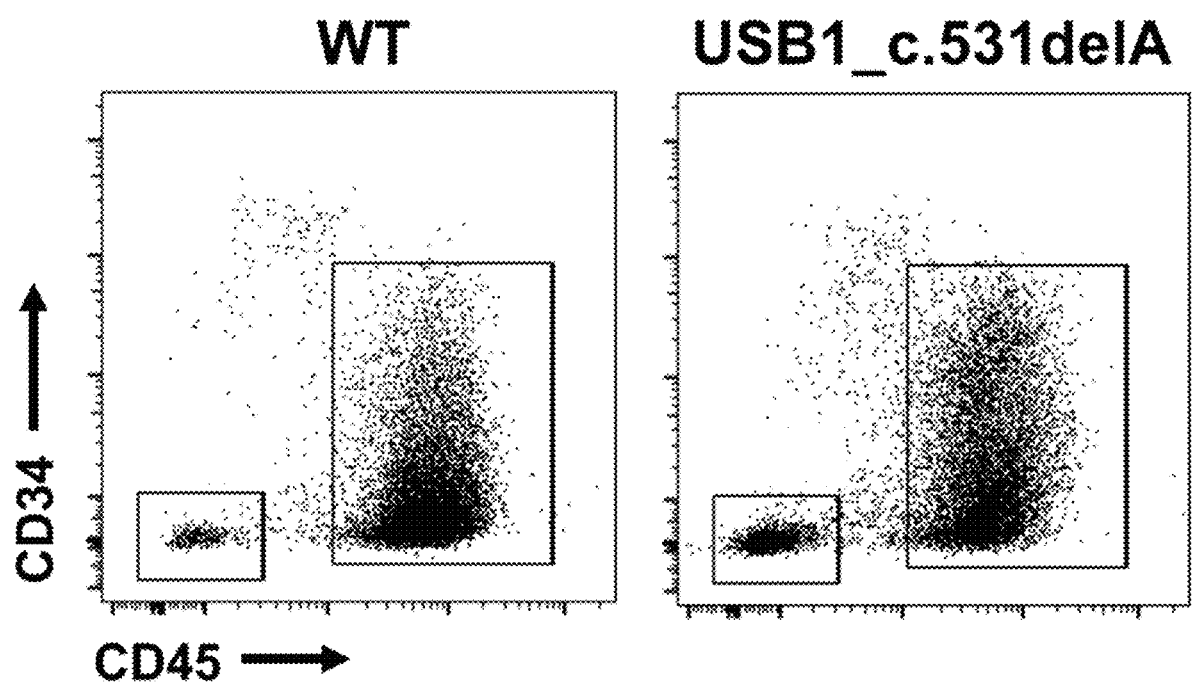
Figure 6G:
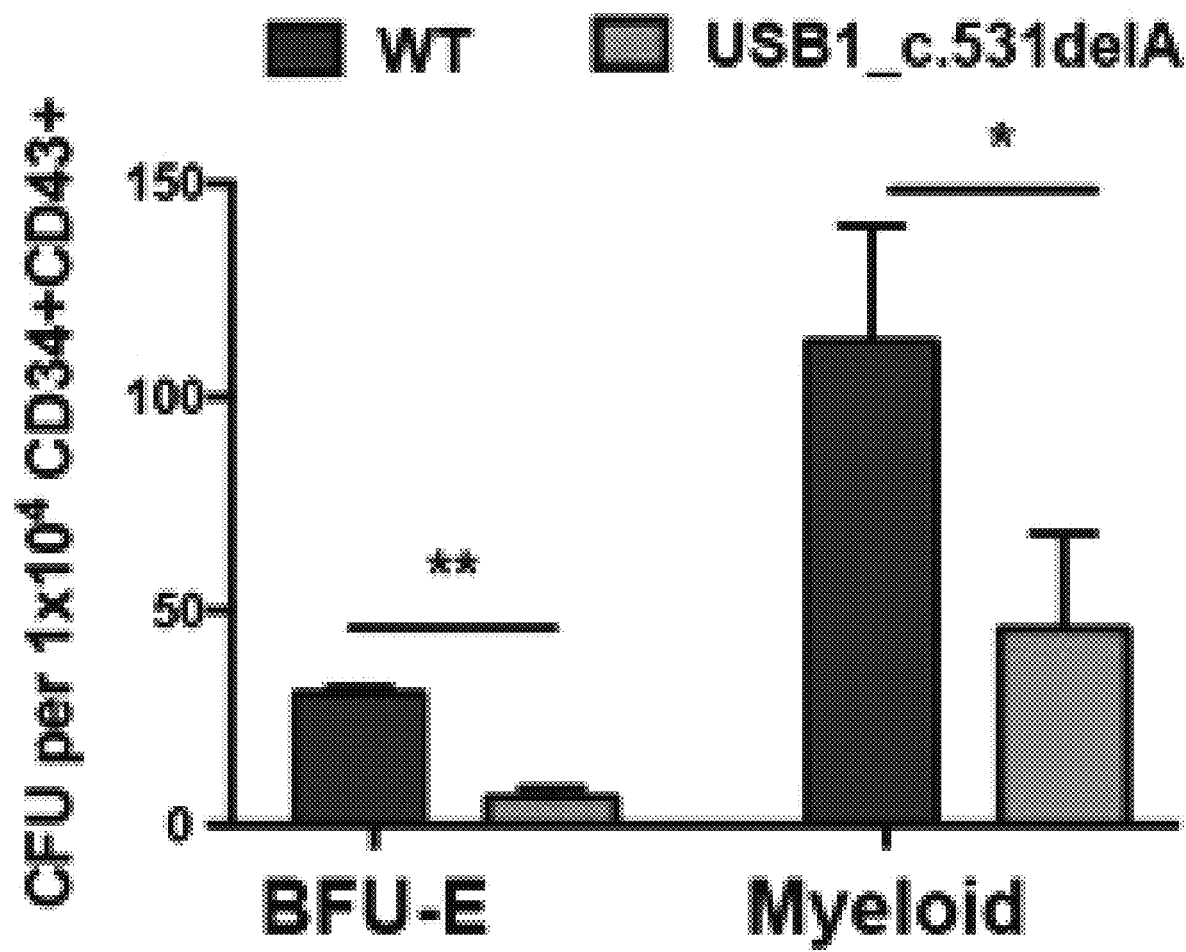

To elucidate the role of USB1 during hematopoiesis, we performed serum-free hematopoietic differentiations to derive hematopoietic progenitor cells from hESCs (FIG. 1A). Gene expression analysis confirmed silencing of pluripotency markers and efficient formation of hematopoietic lineages at the end (Day 30) of differentiation (FIG. 6A). USB1 mutant cells did not show any reduction in the formation of mesoderm (Day 3; FIGS. 6B-C), CD34+/CD43− hemogenic endothelium (HE) or CD34+/CD43+ primitive progenitors when compared to WT cells (Day 8; FIGS. 6D-5E). Strikingly, the formation of definitive hematopoietic progenitors (CD45+) was decreased in USB1 mutant cells compared to WT cells (FIGS. 1B and 6F), and definitive colony potential analysis showed compromised colony formation in USB1 mutant cells (FIG. 1C). Additionally, USB1 mutant cells also showed reduced primitive hematopoietic colony formation potential (FIG. 6G). Consistent with a role of USB1 in regulating hematopoiesis, USB1 mRNA levels increased ~3-fold in mature blood cells compared to undifferentiated hESCs (FIG. 1D). These observations indicate that loss-of function mutations in USB1 negatively influence hematopoiesis.

Figure 6H:
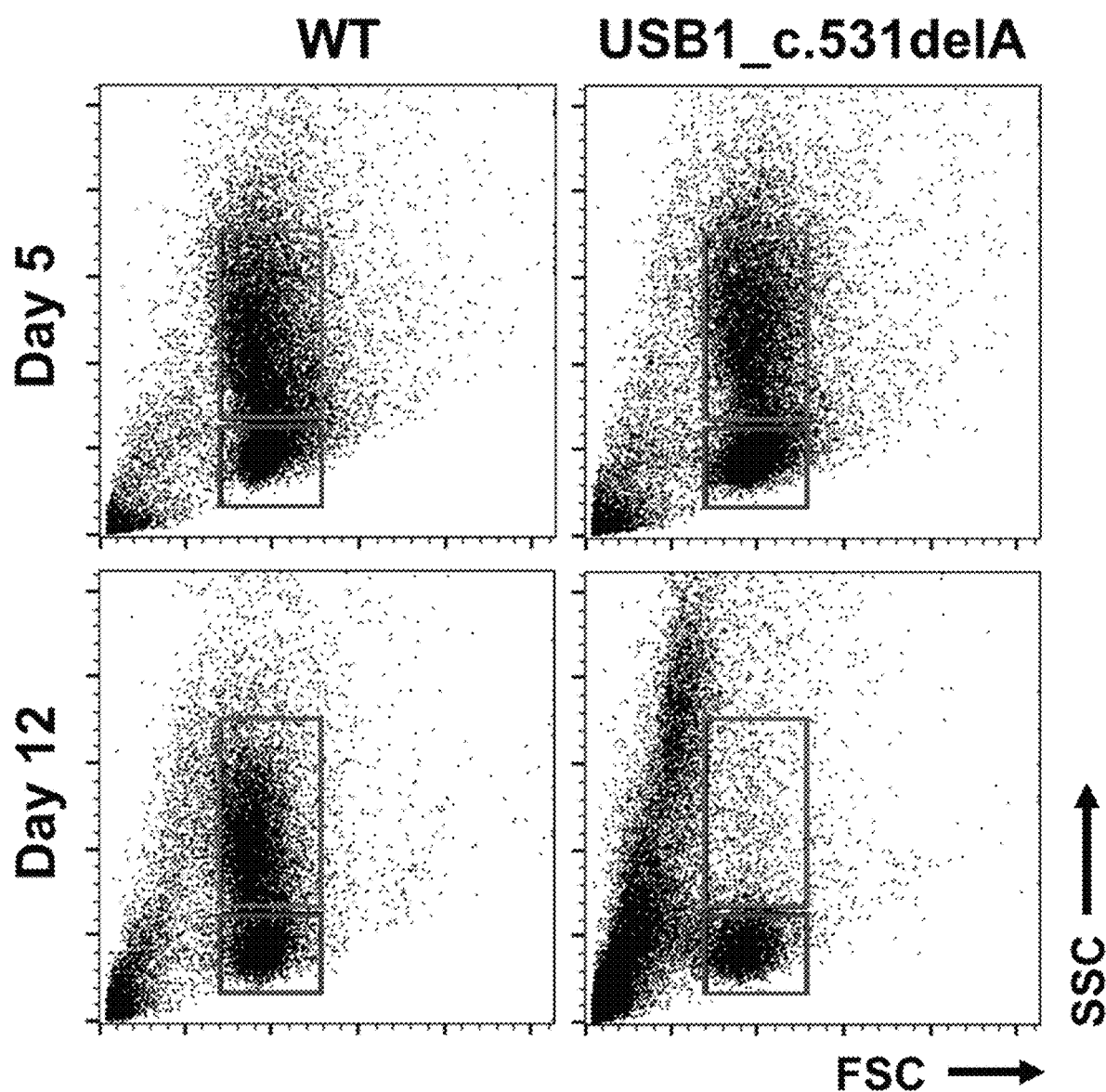
Figure 6H:
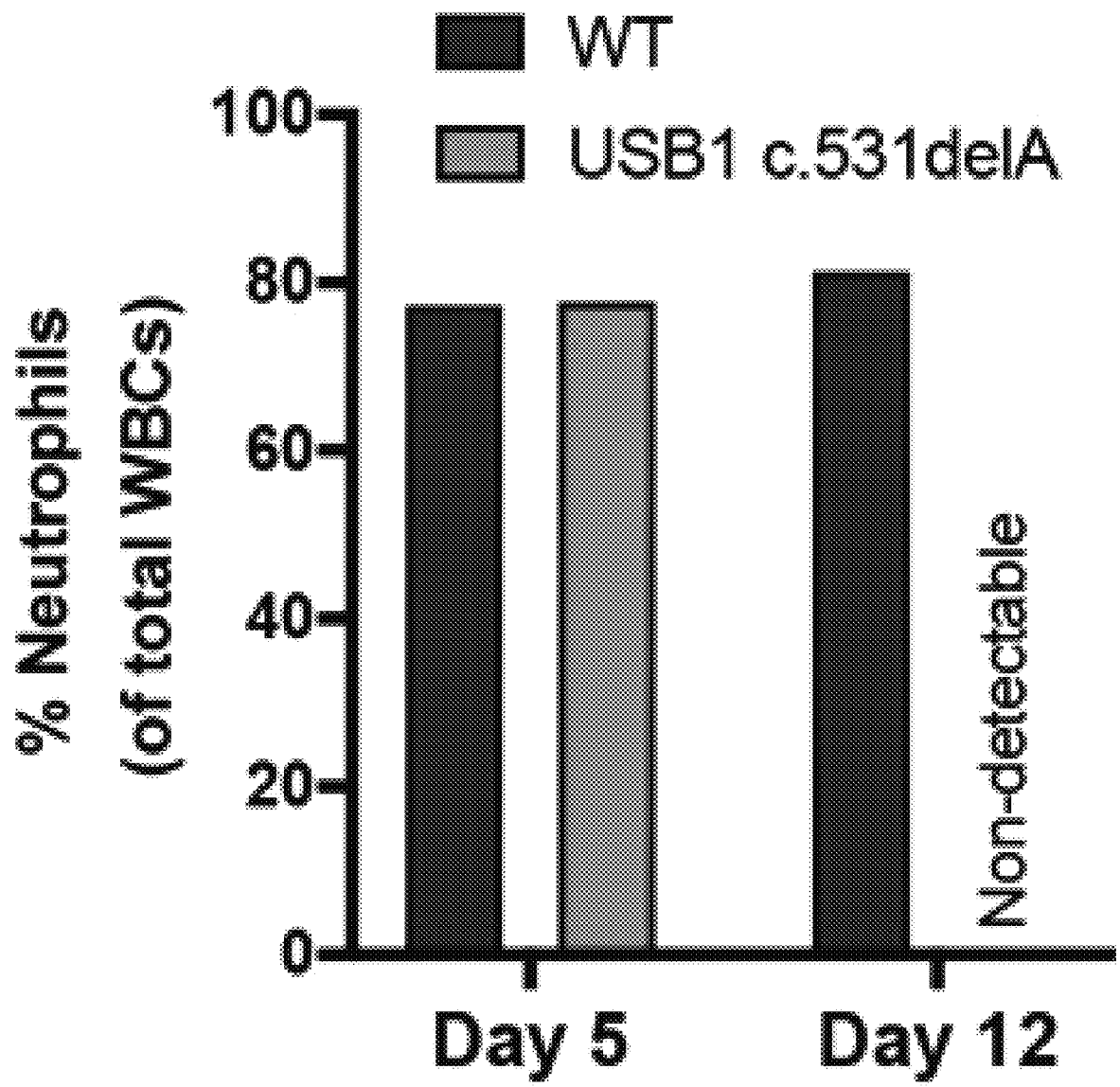
Figure 6I:
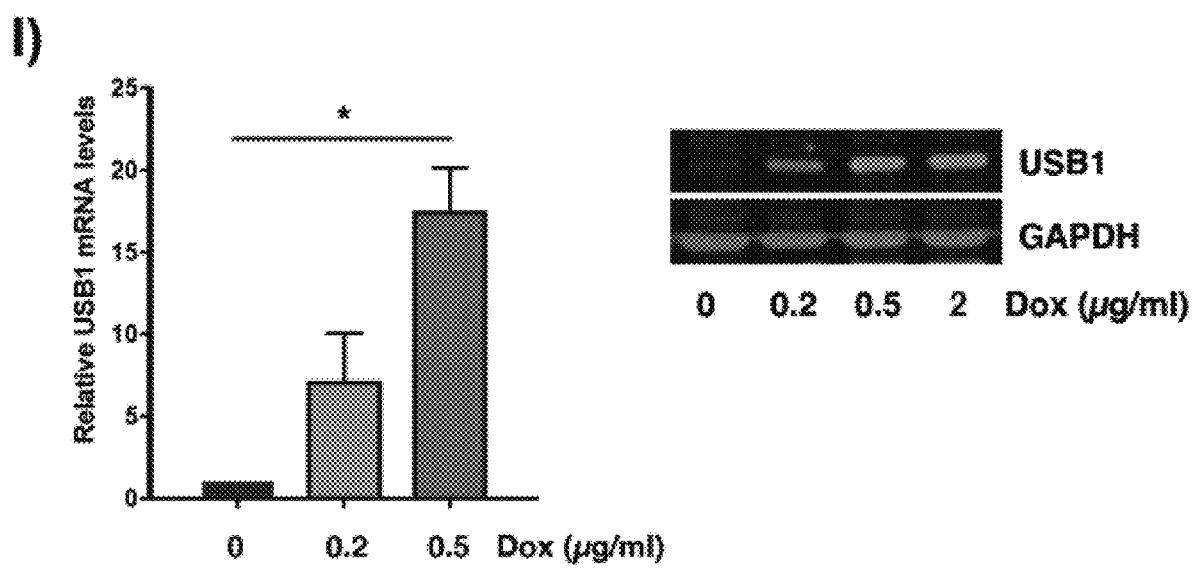

As PN is usually associated with severe non-cyclic neutropenia, we analyzed the potential of neutrophil formation in WT and USB1 mutant cells. We found that USB1 mutants have reduced formation of CD15+/CD66b+ lineages, indicating abnormal neutrophil development (FIGS. 1E and 6H). The conditional expression of the WT USB1 protein in USB1 mutants using a Dox-inducible system rescued the definitive hematopoietic potential of these cells (FIGS. 1F and 6I). These results recapitulate major clinical manifestations of the USB1 deficiency and establish USB1 as an important regulator of hematopoiesis in human cells.

Example 3: USB1 Alters RNAs to Affect Hematopoiesis

To determine the molecular mechanism by which USB1 regulates hematopoiesis, we initially examined if the USB1 mutation affected U6 snRNA. Northern blot analysis of WT and USB1 mutant cells at undifferentiated (D0) and hematopoietic progenitor (D16) stages showed no reduction in the overall levels of U6 and U6atac snRNAs in USB1 mutants (FIGS. 1G and 7A). We did observe that U6 and U6atac snRNA from USB1 mutant cells were slightly longer compared to WT cells (FIGS. 1G and 7A), indicating aberrant post-transcriptional processing of these snRNAs similar to what is observed in patient-derived cells.

Sequencing the 3' end of U6 snRNA from WT and USB1 mutant cells revealed two changes. First, while ~40% of all U6 reads terminated at the +1 U adjacent to the Lsm 2-8 boundary site in WT cells, in USB1 mutant cells, additional Us were present with the majority of ends terminating at the +3 U and +4 U (FIG. 1H). Similar results were observed for the U6atac snRNA (FIG. S3B). Second, we observed that the extended U6 and U6atac 3' ends were heavily oligoadenylated in USB1 mutant cells (FIGS. 1I and S3C). This suggests that the U6 3' ends are oligoadenylated during U6 snRNA maturation and require USB1 for deadenylation and trimming of the uridylated tail. However, USB1 mutant cells have similar levels of these snRNAs compared to WT cells and do not exhibit global pre-mRNA splicing changes (see below), suggesting that USB1 is altering other RNAs to affect hematopoiesis.

Example 4: USB1 Mutation Affects Key mRNAs Important for Cell Growth

Figure 8A:
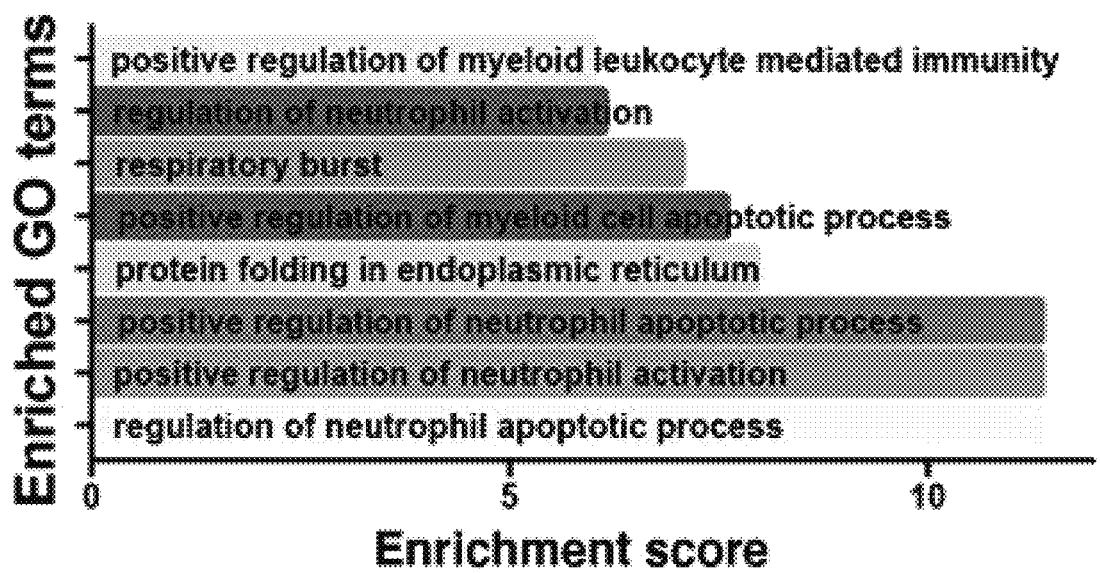
Figure 8B:
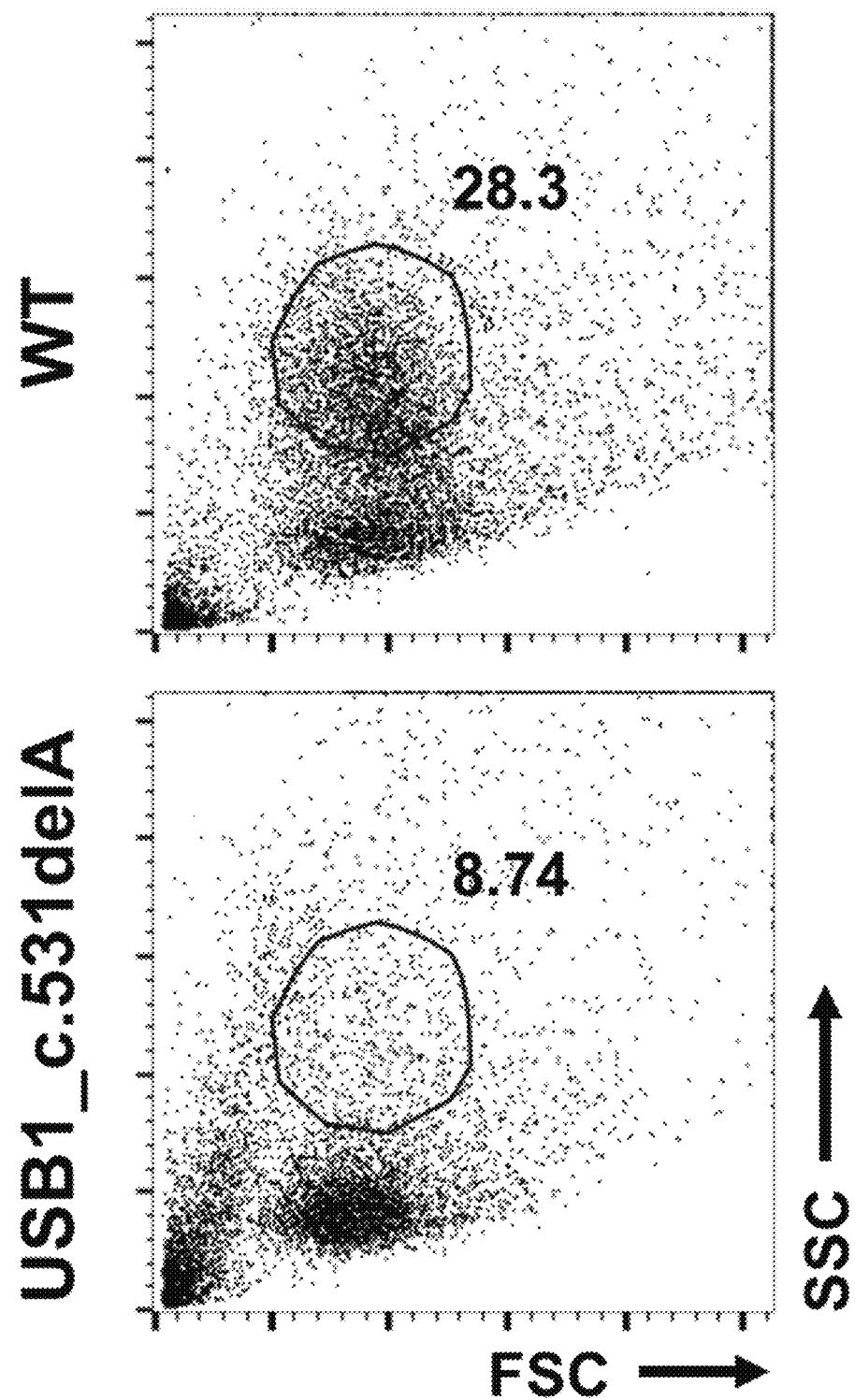
Figure 8B:
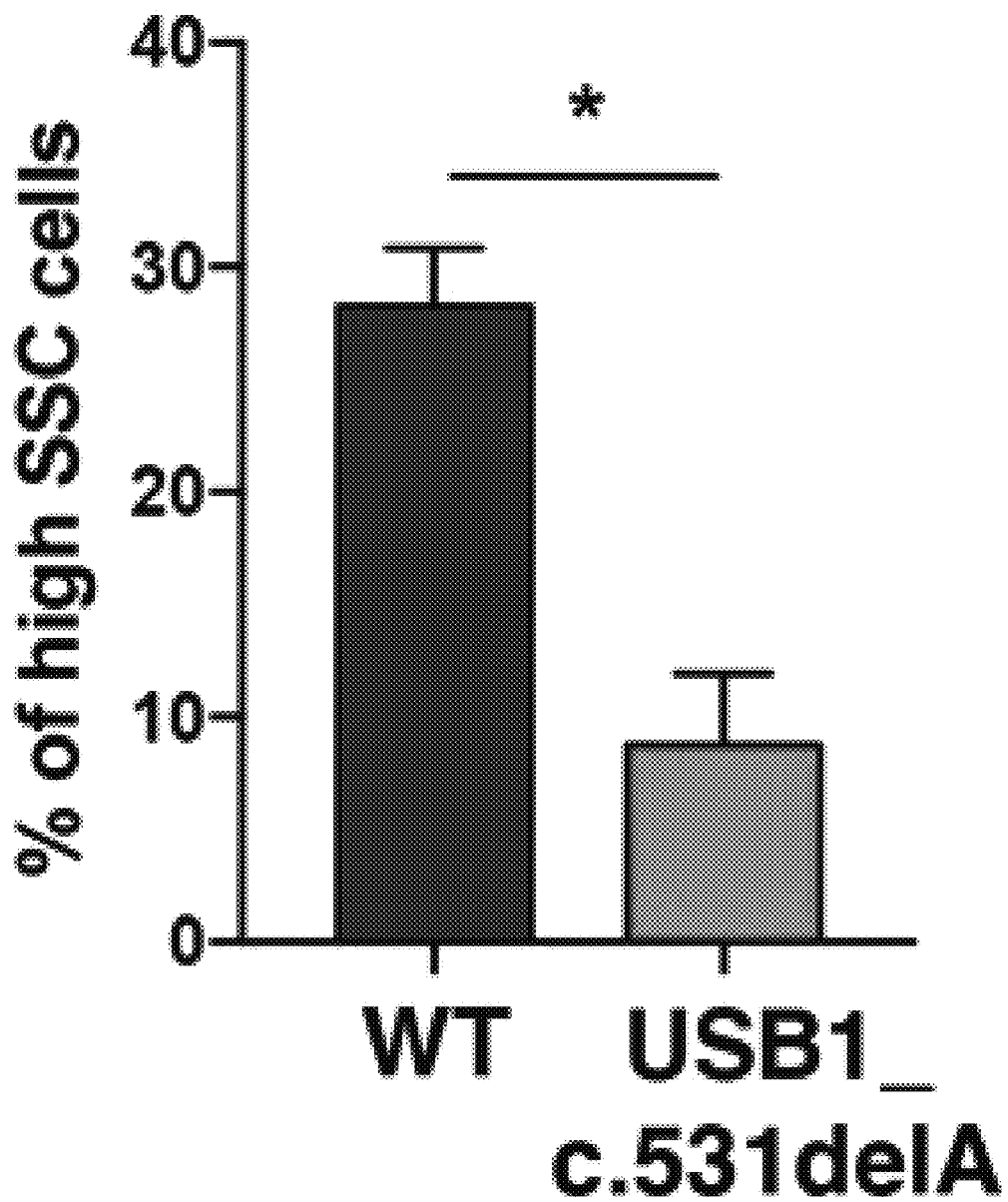

To identify other RNAs affected by USB1, we sequenced the transcriptome and miRome of WT and USB1 mutant cells in the undifferentiated, hematopoietic progenitor (CD34+/CD45+) and mature blood cell populations (FIG. 1A). We observed few significant changes in gene expression in USB1 mutants in undifferentiated hESCs (469 genes out of 15913 genes were affected with FDR<0.1; 164 genes downregulated more than 2-fold and 61 genes upregulated more than 2-fold) (FIG. 2A). As differentiation progressed, we observed more changes in CD34+/CD45+ cells, suggesting that the defect in hematopoiesis occurs during specific stages of differentiation (3310 genes out of 15559 genes were affected with FDR<0.1; 704 genes downregulated more than 2-fold and 577 genes upregulated more than 2-fold) (FIG. 2B). Differentially expressed genes in USB1 mutant cells enriched for gene ontology (GO) pathways involved in regulating cell death and neutrophil differentiation (FIG. 8A). Consistent with an effect of USB1 deficiency on hematopoietic progenitors but not on hESCs, we only observe a decrease in high granular SSC populations in USB1 mutant cell numbers upon neutrophil development, when compared to WT cells (FIG. 8B). Finally, we also observed more gene expression changes in the USB1 mutant cells when compared to WT cells in their mature blood population (2,666 out of 16,310 genes were affected with FDR<0.1; 510 genes downregulated more than 2-fold and 883 genes upregulated more than 2-fold) (FIG. S4C). Taken together, this suggests that mutations in USB1 have a greater effect on gene expression in differentiating hematopoietic progenitors and mature blood cells, which correlates with an increase in USB1 levels at these specific stages of differentiation (FIG. 1D).

An important result was that we did not detect global splicing changes in the transcriptome of USB1 mutants at any stage when compared to WT cells and very few differentially expressed genes were mis-spliced in USB1 mutant cells (FIGS. 2C and 8D). Previous analysis of PN patient lymphoblasts also did not reveal global splicing changes in cells (10). This is consistent with normal levels of U6 snRNA and U6atac snRNA in USB1 mutant cells and suggests that USB1 deficiency affects gene expression through a mechanism distinct from pre-mRNA splicing. Next, we investigated whether specific mRNA changes in USB1 mutant cells could explain the hematopoietic failure observed and identified that transcription factors associated with efficient neutrophil formation (i.e., CEBPA and CEBPE) and overall hematopoiesis (i.e., RUNX1, RUNX2) are downregulated in USB1 mutants (16-19) (FIG. 2D). Combined, these results indicate that despite not affecting U6 levels and pre-mRNA splicing, mutations in USB1 impair correct activation of key hematopoietic and neutrophil development pathways.

Example 5: USB1 Modulates miRNA Levels in Human Stem and Hematopoietic Progenitor Cells We next investigated if mutations in USB1 could affect miRNA levels in hESCs and their hematopoietic progeny. We observed that the USB1 mutation affected the levels of several miRNAs in undifferentiated hESCs (82 out of 374 miRNAs were affected with p<0.05; 49 miRNAs were downregulated and 33 miRNAs were upregulated) (FIG. 2E). We observed increased changes in miRNA levels in CD34+/CD45+ cells in USB1 mutants (131 out of 771 miRNAs were affected with p<0.05; 82 miRNAs were downregulated and 49 miRNAs were upregulated) (FIG. 2F). We verified the downregulation of specific miRNAs in USB1 mutant cells by qRT-PCR, and found that miR-125a-5p, miR-125b-5p, miR-199a-3p, miR-142-5p, miR-223-3p and miR-409-3p were decreased in USB1 mutant cells compared to WT cells (FIG. 2G). Expression of the WT USB1 protein in CD34+/CD45+ USB1 mutants using a Doxinducible system rescued the levels of miR-142-5p, miR-199a-3p and miR-223-3p in these cells (FIG. 2H). These observations demonstrate that USB1 modulates miRNA levels in human stem and hematopoietic progenitor cells.

Similar to the effect of USB1 mutation on specific mRNAs in CD34+/CD45+ cells, we observed a decrease in the levels of miRNAs involved in myeloid and granulocytic differentiation, such as miR-142-5p and miR-223-3p, in CD34+/CD45+ USB1 mutant cells (FIG. 2G) (20, 21). KEGG analysis of the differentially expressed miRNAs in USB1 mutant cells revealed that these miRNAs predominantly affect pathways involved in cancer progression, including acute myeloid leukemia (AML), which is frequently associated with PN (FIG. S4E) mutations in USB1 impair correct activation of key hematopoietic and neutrophil development pathways.

Example 6: USB1 Regulates Cellular Pathways Related to Hematopoietic Development We next investigated if mutations in USB1 could affect miRNA levels in hESCs and their hematopoietic progeny. We observed that the USB1 mutation affected the levels of several miRNAs in undifferentiated hESCs (82 out of 374 miRNAs were affected with p<0.05; 49 miRNAs were downregulated and 33 miRNAs were upregulated) (FIG. 2E). We observed increased changes in miRNA levels in CD34+/CD45+ cells in USB1 mutants (131 out of 771 miRNAs were affected with p<0.05; 82 miRNAs were downregulated and 49 miRNAs were upregulated) (FIG. 2F). We verified the downregulation of specific miRNAs in USB1 mutant cells by qRT-PCR, and found that miR-125a-5p, miR-125b-5p, miR-199a-3p, miR-142-5p, miR-223-3p and miR-409-3p were decreased in USB1 mutant cells compared to WT cells (FIG. 2G). Expression of the WT USB1 protein in CD34+/CD45+ USB1 mutants using a Doxinducible system rescued the levels of miR-142-5p, miR-199a-3p and miR-223-3p in these cells (FIG. 2H). These observations demonstrate that USB1 modulates miRNA levels in human stem and hematopoietic progenitor cells.

Similar to the effect of USB1 mutation on specific mRNAs in CD34+/CD45+ cells, we observed a decrease in the levels of miRNAs involved in myeloid and granulocytic differentiation, such as miR-142-5p and miR-223-3p, in CD34+/CD45+ USB1 mutant cells (FIG. 2G) (20, 21). KEGG analysis of the differentially expressed miRNAs in USB1 mutant cells revealed that these miRNAs predominantly affect pathways involved in cancer progression, including acute myeloid leukemia (AML), which is frequently associated with PN (FIG. 8E) (22). Together, this suggests that USB1 regulates important cellular pathways related to hematopoietic development.

Example 7: USB1 Functions as a Deadenylase for miRNAs, U6 snRNA and can Remove a Single U from the 3' End of RNAs We hypothesized that USB1 might regulate miRNAs by removing 3' oligo(A) tails that would otherwise trigger miRNA degradation for three reasons. First, 3' oligoadenylation of miRNAs by the non-canonical poly(A) polymerases PAPD5 & PAPD7 can promote their degradation by the cytoplasmic 3' to 5' exonucleases DIS3L and/or DIS3L2 (23). Second, removal of oligo(A) tails by the poly(A) specific nuclease PARN stabilizes miRNAs (23). Finally, USB1, while generally thought to act on U tails, can remove poly(A) tails in vitro (24). This hypothesis predicts that miRNAs regulated by USB1 would show increased levels of 3' adenylation in USB1 mutant cells, and that recombinant USB1 would deadenylate 3' adenylated miRNAs. To test this hypothesis, we sequenced the 3' ends of miRNAs that are differentially expressed in USB1 mutant cells at different stages of hematopoietic differentiation.

An important observation was that the USB1 mutation led to an increase in the levels of oligoadenylated reads at 3' ends of miR-125a-5p in undifferentiated hESCs and miR-223-3p in CD34+/CD45+ cells (FIGS. 3A and B). In WT cells, miR-125a-5p terminates at either the gnomically encoded 5'-GUG-3' or 5'-GUGA-3' in a 1:1 ratio (FIG. 3A). However, in USB1 mutant cells, we observed a decrease in the 5'-GUG-3' fraction and a proportional increase in the 5'-GUGA-3' and extended oligoadenylated fraction (FIG. 3A). Similarly, we observed that for miR-223-3p in CD34+/CD45+ cells, USB1 mutants contained more oligoadenylated ends compared to WT cells (FIG. 3B). Taken together, this data suggests that USB1 is a potential miRNA deadenylase that removes 3' A tails that could otherwise enhance the degradation of miRNAs by 3'-to-5' exonucleases.

Next, to test if USB1 could directly deadenylate an adenylated miRNA, we purified recombinant human USB1 (wild-type and a catalytically inactive mutant H208Q) and tested its activity on 5'-FAM labeled miR-125a-5p substrates with different 3' end additions (FIG. 3C). We observed that wild type, but not catalytically inactive USB1, efficiently removed the adenosine(s) from the 3' end of miR-125a in a time-dependent manner, as seen by the shortened products observed for native miR-125a (which has a single A at its 3' end), oA and oUA substrates (FIG. 3C-G). USB1 was also able to rapidly remove adenosines but not uridines from the 3' end of U6 snRNA oligo (FIG. 3H-J). This demonstrates USB1 can function as a deadenylase for miRNAs and U6 snRNA in vitro.

Our data suggests that USB1 can also remove single uridine residues from RNA substrates but cannot efficiently remove poly(U) tails. Specifically, USB1 slowly removed one uridine from the 3' end of oligouridylated miR-125a substrates, as observed by the appearance a small amount of product shorter by one nucleotide (FIGS. 3C and G), which we confirmed with shorter RNA substrates (FIG. 9A-C). USB1 also removed a single uridine residue from an oligouridylated 3' end of the U6 snRNA (FIGS. 3H and I). This demonstrates that USB1 can remove a single U from the 3' end of RNAs but is not sufficient to progressively remove an oligo(U) tail.

Example 8: Inhibition of PAPD5/7 Rescues the Differentiation Defects Seen in USB1 Mutant Cells Our data suggests that the hematopoietic deficit observed in PN patients is caused by a loss of expression of different miRNAs required for blood development due to the failure of USB1 to remove oligo(A) tails added by PAPD5/7. Accordingly, we observed that inhibiting PAPD5 with RG7834, an inhibitor of PAPD5/7 non-canonical poly(A) polymerases, rescued levels of miRNAs that were reduced in USB1 mutant cells (FIG. 4A). Moreover, treatment of USB1 mutants with RG7834 led to a decrease in oligoadenylated miR-125a-5p, which was compensated by an increase in the non-adenylated form, demonstrating that these enzymes are responsible for adding oligo(A) tails to the 3' end of miR- NAs that can be removed by USB1 (FIG. 4B). The genetic silencing of PAPD5 also rescued the levels of miRNAs affected by USB1 mutation in CD34+/CD45+ hematopoietic progenitors (FIG. 4C). These results indicate that inhibition of PAPD5/7 activity would rescue the differentiation defects seen in USB1 mutant cells by preventing the oligoadenylation of miRNAs. To test this hypothesis, we investigated if inhibition of PAPD5 by constitutive silencing using shRNAs (FIG. 10A) or treatment with RG7834 could rescue hematopoietic differentiation of USB1 mutants.

Strikingly, we observed that the compromised colony-formation potential in USB1 mutants is rescued by both the genetic (FIG. 4D) and chemical (FIG. 4E) inhibition of PAPD5. Chemical inhibition of PAPD5/7 by RG7834 treatment also led to an increase in hematopoietic CD34+/CD45+ progenitor cells (FIG. 10B). Importantly, RG7834 treatment also improved the neutrophil formation in USB1 mutant cells, a key feature of hematopoietic failure in PN (FIG. 4F). Combined, these results suggest that the failure to efficiently remove oligo(A) tails from miRNAs during hematopoiesis in settings of mutant USB1 leads to hematopoietic failure in PN, and that inhibition of the poly(A) polymerases PAPD5 and PAPD7 may be a potential therapeutic strategy for treating these patients.

Example 9: Materials and Methods

Cell culture: H1 hESCs (WA01) were acquired from WiCell Research Institute (Madison, WI), following all institutional guidelines determined by the Embryonic Stem Cell Research Oversight Committee (ESCRO) at Washington University in St. Louis. hESCs were maintained in mTeSR1 medium (StemCell Technologies, Vancouver, Canada) on plates coated with Matrigel (BD Biosciences, San Jose, CA) diluted at 1:80 in DMEM/F12 supplemented with 0.1% pen/strep. For feeder based conditions, hESC basal medium (DMEM/F12 supplemented with 1% non-essential amino acids, 0.1% beta-mercaptoethanol, and 0.1% pen/strep) with 20% KnockOut Serum Replacement and 10 ng/ml bFGF was used on growth-arrested mouse embryonic fibroblasts (MEFs). hESCs were cultured in a humidified incubator at 37° C. in 5% CO2 and 5% O2 levels.

Gene editing of hESCs: USB1_c.531delA hESCs were generated using CRISPR/Cas9 genome-editing technology. Briefly, CRISPR gRNAs were inserted into the MLM3636 plasmid (Addgene #43860) and transfected with Cas9 plasmid (Addgene #43945) and single-stranded DNA donor oligos using Lonza's 4D-Nucleofector with the P4 Primary Cell 4D-Nucleofector kit (Allendale, NJ). Cells were seeded at low density, picked manually, and then sequenced. Donor oligo sequences were used as follows;

```
                                      (SEQ ID NO. 4)
5'-ATTGGGCTTGAGGTCACTTC-NGG-3'
and
                                      (SEQ ID NO. 5)
5'-TTGGGCTTGAGGTCACTTCA-NGG-3'.
``` iUSB1-WT/c.531delA and USB1.c531delA_shPAPD5 hESCs were engineered by zinc finger nuclease (ZFN) by targeting the AAVS1 locus. Transfection was performed with X-TremeGene 9 transfection kit (#06 365 779 001; Roche) following the manufacturer's instructions. For shPAPD5, three shRNA hairpins obtained from the Broad Institute were inserted into MIR30 cassette of the AAVS1-GAG-GFP-mir30 plasmid containing AAVS1 homology regions. The shRNA sequences were used as follows;

```
                                      (SEQ ID NO. 6)
5'-GCCACATATAGAGATTGGATA-3'
                                      (SEQ ID NO. 7)
5'-CGATGTTGGAAGGAGTTCATA-3'
                                      (SEQ ID NO. 8)
5'-CCCAATACAAACTATGGTGTT-3'.
```

Hematopoietic differentiation: Definitive hematopoietic differentiation from hESCs was performed as previously described (14). Briefly, hESCs were cultured on Matrigel (BD Bioscience) for 1 day to deplete MEFs. On Day 0, cells were dissociated with 0.05% trypsin (Gibco) for 1 min and incubated with serumfree media [SFD: IMDM supplemented with 25% Hams F12, 0.05% BSA, 1× B27 supplement (Gibco), 0.5× N2 supplement (Gibco), 2 mM L-glutamine (Gibco), 50 µg/ml ascorbic acid (Gibco), 4×10−4 M monothioglycerol (Millipore Sigma), and 150 µg/ml transferrin] supplemented with 10 ng/ml BMP4 on 6 well plates coated with a 5% poly(2-hydroxyethyl methacrylate) solution (Millipore Sigma). On Day 1, one additional volume of SFD was added, containing 10 ng/ml BMP4 and 5 ng/ml bFGF. On Day 2, media was changed to fresh SFD supplemented with 10 ng/ml BMP4, 5 ng/ml bFGF, 3 µM CHIR99021, and 6 µM SB-431542. On Day 3, media was changed to StemPro-34 media [SP-34: StemPro-34 supplemented with 2 mM L-glutamine (Gibco), 1 mM ascorbic acid (Gibco), 4×10−4M monothioglycerol, 150 µg/ml transferrin] supplemented with 15 ng/ml VEGF and 5 ng/ml bFGF. On Day 6, one additional volume of SP-34 supplemented with 15 ng/ml VEGF, 5 ng/ml bFGF, 20 ng/ml IL-6, 50 ng/ml IGF1, 10 ng/ml IL-11, 200 ng/ml SCF, and 4 IU EPO was added. For primitive hematopoietic differentiation, on Day 2, the media was changed to fresh SFD supplemented with 10 ng/ml BMP4, 5 ng/ml bFGF, 1 ng/ml Activin A, and 3 µM IWP2. Every step was maintained in a 5% CO2 and 5% O2 incubator. All cytokines were purchased from R&D BioSystems (Minneapolis, MN), but EPO and IGF1 were obtained from Peprotech (Rocky Hill, NJ).

Colony forming culture assays: Colony assays were performed using MethoCult H4034 Optimum (StemCell Technologies, Vancouver, Canada). 10,000 CD34+CD43− or CD34+CD43− CD73−CD184− cells sorted at Day 8 were aggregated overnight in a well of a 96 well low-adhesion plate at 2×105 cells/ml density in 50 µl of SP-34 supplemented with 30 ng/ml TPO, 30 ng/ml IL-3, 100 ng/ml SCF, 10 ng/ml IL-6, 5 ng/ml IL-11, 25 ng/ml IGF1, 2 IU EPO, 5 ng/ml VEGF, 5 ng/ml bFGF, 10 ng/ml BMP4, 10 ng/ml FLT3L, and 20 ng/ml SHH. Aggregates were transferred to a well of a Matrigel-coated 24 well plate and 1 ml of the same supplemented SP-34 media was added 6 hr post-transfer. Cells were maintained in 5% CO2 and 5% O2 incubator for 8 days and then placed into 1 ml of MethoCult in which the colonies forming were measured after 12 days. All cytokines were purchased from R&D BioSystems, but EPO and IGF1 were obtained from Peprotech.

Flow cytometry and Cell sorting: Flow cytometry analysis was performed using the BD LSR Fortessa and FACS sorting by BD FACS Aria II at the Department of Pathology & Immunology Flow Cytometry Core at Washington University in St. Louis. The antibodies were used as follows; KDR (clone 89106), CD235a-APC (clone HIR2), CD34-APC (clone 8G12), CD34-PE-Cy7 (clone 4H11), CD43-PE or -FITC (clone 1G10), CD73-PE (clone AD2), CD184-APC (clone 12G5), CD45-PE (clone HI30), CD14-PE Cy7 (clone MφP9), CD15-BV421 (W6D3), CD66b-FITC (clone G10F5). All antibodies were purchased from BD Biosciences, but CD15 and CD66b were obtained from BioLegend. For cell cycle analysis, Click-iT EdU Alexa Fluor 488 kit (Life Technologies) was used following manufacturer's instructions.

RNA extraction and abundance measurement: Total RNA was isolated using Trizol (Invitrogen) using Phasemaker tubes in accordance with the manufacturer's instructions. Contaminating gDNA was removed using Turbo DNA-free kit (Invitrogen). RNA concentration was measured using Qubit assay (Thermo Fisher). For the measurement of mRNA levels in FIG. 2D, cDNA was synthesized from total RNA using RNA-to-cDNA EcoDry premix (Double primed) (Takara Biotech). qRT-PCR was performed using iQ SYBR Green Supermix (BioRad) on the CFX96 thermocycler (BioRad). Relative mRNA levels were calculated using the $2^{-\Delta\Delta Ct}$ method. For the measurement of miRNA levels in FIGS. 2G and 4A, cDNA was synthesized using Mir-X miRNA first strand synthesis kit (Takara Biotech). qRT-PCR was performed using TB Green Advantage qPCR premix (Takara Biotech) and measured on the CFX96 thermocycler (BioRad). The entire miRNA sequence was used as a reverse primer for qRT-PCR. For northern blot analysis of U6 and U6atac snRNA, 1 µg of total RNA was separated on an 8% polyacrylamide 7M Urea gel in 1×TBE. RNA was transferred to a Nytran Supercharge blotting membrane (Thermo Fisher). Blots were probed with g-32P radiolabeled probes and imaged on a Typhoon phosphoimager. Densitometry analysis was performed using Fiji. For other qRT-PCR experiments, RNA was converted into cDNA using Superscript III First Strand synthesis kit (Invitrogen) following manufacturer's instructions. Real-time PCR was performed using Evagreen master mix (Lambda Biotech, St. Louis, MO) on a StepOne Plus instrument (Thermo Fisher Scientific). For miRNA, TaqMan microRNA reverse transcription kit (Applied Biosystems) was used to detect miR142-5p (4427975-002248), miR-199a-3p (4427975-002304), miR-223 (4427975-002295), and RNU44 (4427975-001094). mRNA qRT-PCR primer sequences are listed in Table 1.

RNA-seq library preparation and analysis: For strand-specific library preparation, DNA-free total RNA was used as a starting material. Ribosomal RNA was depleted using RiboCop rRNA depletion kit HMR V2 (Lexogen) as per manufacturer's protocol. 10 ng of depleted RNA was used as input for library preparation using the NextFlex Rapid Directional RNA-Seq kit 2.0 (Perkin Elmer) as per manufacturer's protocol. Libraries were analyzed on Bioanalyzer (Agilent) to check for concentration and correct fragment insertion. Libraries were pooled together and sequenced on the NovaSeq 6000 (Illumina) using the 2×150 kit to obtain paired ends RNA-seq reads. Reads were demultiplexed and adapters and low-quality bases were trimmed using Trimmomatic (34). Trimmed reads were aligned to the human cDNA transcriptome (ENSEMBL GRCh38 v99) and were quantified using Salmon (35). Transcript quantifications were imported to DeSeq2 and differential expression analysis was performed under default parameters (36). Downstream analysis and visualization were performed in R. For analysis of splicing differences between WT and USB1 mutants at different stages of differentiation, trimmed RNA-seq reads were aligned to the human genome (ENSEMBL GRCh38 v99) using STAR (37). Aligned SAM files were coordinate-sorted and compressed to BAM files. Indexed BAM files were used as input and local splice variations (LSVs) were calculated in each sample using MAJIQ (38). Differentially spliced LSVs obtained from MAJIQ were converted to TSVs using Voila tool in the MAJIQ package.

miRNA-seq library preparation and analysis: 300 ng of DNA-free total RNA was used as input for library preparation using the Small RNAseq library prep kit (Lexogen). Amplified libraries were size-selected to enrich for smaller inserts using the companion magnetic bead module. Libraries were pooled together and sequenced on the NovaSeq 6000 (Illumina) using the 2×150 kit to obtain paired ends RNA-seq reads. Reads were demultiplexed and adapters were trimmed using Cutadapt (39). Trimmed reads were aligned to human miRNA database (miRbase V22) using Bowtie2 allowing no mismatches in the seed-sequence (40). Aligned miRNA counts were extracted from sorted BAM alignments and differential expression analysis was performed using DESeq2 (36). Downstream analysis and visualization were performed in R.

3' end library preparation and analysis: 3' end libraries were prepared as previously described (23, 41). Briefly, 30 ng of DNA-free rRNA-depleted RNA was treated with Antarctic Phosphatase (NEB), and two RNA appendices containing a unique barcode were ligated to equal amount of the input RNA using T4 RNA Ligase I (NEB). Reactions were cleaned up using RNA clean & concentrator kit (Zymo Research) and cDNA was prepared using an RNA appendix-specific primer and Superscript III RT (Invitrogen). cDNA was used as a template for 5' RACE using a miRNA-specific reverse primer containing a barcode, a universal primer and Phusion HF DNA polymerase (NEB). RACE products were separated on a 1% Agarose TAE gel, 100-180 bp DNA fragments were excised and DNA was eluted. Illumina-compatible libraries were prepared by amplifying RACE product using Illumina primers, and sequenced on a HiSeq lane (Illumina) using the 2×150 kit. Libraries were demultiplexed and unique reads aligning to the exact miRNA sequence were quantified. miRNA 3' ends were obtained from miRbase v22.

Recombinant USB1 purification: Human USB1 cDNA sequence was cloned in the NdeI-XhoI cleavage site of the PColdI *E. coli* expression vector (Takara Biotech). Catalytic mutant USB1 was prepared by site-directed mutagenesis of the WT USB1 plasmid by changing H208 to Q. The plasmid was transformed in Rosetta2 (DE3) cells and USB1 expression was induced using cold shock and 1 mM IPTG as per manufacturer's instruction (Takara Biotech). The culture was pelleted and lysed by sonication in lysis buffer as described previously (24). His-USB1 was purified using Ni-NTA resin (Qiagen) and eluted using 500 mM Imidazole. Eluted protein was concentrated using Amicon filter tubes by centrifugation with 10 kDa cutoff to a 500 ul volume. Concentrated protein was applied to an AKTA FPLC with Superdex 75 increase 30 column (separation range between 7 and 75 KDa) and USB1 was purified using size exclusion chromatography. Fractions were pooled and concentrated down to 1 ml volume in Amicon KDa filter and buffer was exchanged to storage buffer using dialysis. Purified protein was aliquoted and stored at −80 C.

RNA degradation assays with recombinant USB1: RNA oligos used for the assays containing a 5′-FAM label were purchased from IDT. The sequences are as follows:

```
miR125a-native:
                                        (SEQ ID NO. 9)
UCCCUGAGACCCUUUAACCUGUGA miR125a-oA:
                                       (SEQ ID NO. 10)
UCCCUGAGACCCUUUAACCUGUGAAAAAA miR125a-oU:
                                       (SEQ ID NO. 11)
UCCCUGAGACCCUUUAACCUGUGAUUUUU miR125a-oUA:
                                       (SEQ ID NO. 12)
UCCCUGAGACCCUUUAACCUGUGAUUAAA miR125a-oAU:
                                       (SEQ ID NO. 13)
UCCCUGAGACCCUUUAACCUGUGAAAUUU U6-oU:
                                       (SEQ ID NO. 14)
AAUUCGUGAAGCGUUCCAUAUUUUU U6-oA:
                                       (SEQ ID NO. 15)
AAUUCGUGAAGCGUUCCAUAUUUUUAAAAAAA U6-oUA:
                                       (SEQ ID NO. 16)
AAUUCGUGAAGCGUUCCAUAUUUUUAAUAAUAAUAA 16mer-native:
                                       (SEQ ID NO. 17)
CCUUUCCCCUUUCCGC 16mer-oA:
                                       (SEQ ID NO. 18)
CCUUUCCAAAAAAAA 16mer-oU:
                                       (SEQ ID NO. 19)
CCUUUCCUUUUUUUU 16mer-oUA:
                                       (SEQ ID NO. 20)
CCUUUCCUUUAAAAA 16mer-oAU:
                                       (SEQ ID NO. 21)
CCUUUCCAAAAUUUU
```

5 µM of USB1 was incubated with 1 µM of RNA substrate in 10 µl reaction volume at 37 C for the described duration in 1× reaction buffer (20 mM Hepes pH 7.4, 100 mM NaCl, 1 mM EDTA) as previously described (24). Reactions also contained RNAsin (Promega) to prevent contaminating RNAse activity and 1 mM TCEP pH 7.4. Reactions were stopped with 2× formaldehyde loading dye and reaction products were separated on a 15% acrylamide TBE-Urea gel (Invitrogen) in 1×TBE buffer. Fluorescent RNA was visualized on a Typhoon Phosphoimager and densitometry analysis was performed using Fiji.

Telomere length analysis: Telomere length was quantified by Telomere Repeat Fragment (TRF). Briefly, 10 µg of DNA was digested with RSA and HINF1 restriction enzymes (New England Biolabs, Ispwich, MA) overnight and 2.5 µg of product was resolved in a 0.75% agarose gel for 16 hr at 85V in TBE buffer. The gel was incubated with denaturing buffer (1.5M NaCl and 0.5M NaOH) for 45 min followed by neutralizing buffer (1.5M NaCl, 1M Tris-HCl at pH 7.4) for 1 hr. DNA was transferred to a nitrocellulose membrane by capillary action for 2 days in 10× saline-sodium citrate (3M NaCl, 0.3M sodium citrate dehydrate at pH 7.0). After cross-linking, the membrane was hybridized with a 32P-labelled probe (TTAAGGG)4 and exposed to Carestream BioMax MT film.

G-banded karyotyping: The karyotypes were determined by Cell Line Genetics (Madison, WI).

Statistical analysis: Graphical data are presented as mean±standard deviation (SD). Statistical tests were performed as described in the figure legend. Statistical significance for more than three groups was determined using one-way or two-way analysis of variance (ANOVA) following a Tukey multiple comparison post-test. Statistical significance between the two groups was analyzed using unpaired Student's t-tests. The statistical significance was assumed to be $*p<0.05$, $p<0.01$, and $*p<0.001$.

REFERENCES

1. A. J. Walne, L. Collopy, S. Cardoso, A. Ellison, V. Plagnol, C. Albayrak, D. Albayrak, S. S. Kilic, T. Pat roglu, H. Akar, K. Godfrey, T. Carter, M. Marafie, A. Vora, M. Sundin, T. Vulliamy, H. Tummala, I. Dokal, Marked overlap of four genetic syndromes with dyskeratosis congenita confounds clinical diagnosis. *Haematologica*. 101, 1180-1189 (2016).
2. A. J. Walne, T. Vulliamy, R. Beswick, M. Kirwan, I. Dokal, Mutations in C16orf57 and normal-length telomeres unify a subset of patients with dyskeratosis congenita, poikiloderma with neutropenia and Rothmund-Thomson syndrome. *Hum Mol Genet*. 19, 4453-4461 (2010).
3. L. Volpi, G. Roversi, E. A. Colombo, N. Leijsten, D. Concolino, A. Calabria, M. A. Mencarelli, M. Fimiani, F. Macciardi, R. Pfundt, E. F. P. M. Schoenmakers, L. Larizza, Targeted next-generation sequencing appoints c16orf57 as clericuzio-type poikiloderma with neutropenia gene. *American journal of human genetics*. 86, 72-6 (2009).
4. D. Concolino, G. Roversi, G. L. Muzzi, S. Sestito, E. A. Colombo, L. Volpi, L. Larizza, P. Strisciuglio, Clericuzio-type poikiloderma with neutropenia syndrome in three sibs with mutations in the C16orf57 gene: Delineation of the phenotype. *Am J Med Genet A*. 152A, 2588-2594 (2010).
5. A. Tanaka, F. Morice-Picard, D. Lacombe, N. Nagy, M. Hide, A. Taïeb, J. McGrath, Identification of a homozygous deletion mutation in C16orf57 in a family with Clericuzio-type poikiloderma with neutropenia. *American journal of medical genetics. Part A*. 152A, 1347-8 (2010).
6. S. Mroczek, J. Krwawicz, J. Kutner, M. Lazniewski, I. Kuciński, K. Ginalski, A. Dziembowski, C16orf57, a gene mutated in poikiloderma with neutropenia, encodes a putative phosphodiesterase responsible for the U6 snRNA 3′ end modification. *Genes & development*. 26, 1911-25 (2012).
7. V. Shchepachev, H. Wischnewski, E. Missiaglia, C. Soneson, C. M. Azzalin, Mpn1, mutated in poikiloderma with neutropenia protein 1, is a conserved 3′-to-5′ RNA exonuclease processing U6 small nuclear RNA. *Cell reports*. 2, 855-65 (2012).
8. V. Shchepachev, H. Wischnewski, C. Soneson, A. W. Arnold, C. M. Azzalin, Human Mpn1 promotes posttranscriptional processing and stability of U6atac. *FEBS Letters.* 589, 2417-2423 (2015).
9. E. A. Colombo, S. Carra, L. Fontana, E. Bresciani, F. Cotelli, L. Larizza, A zebrafish model of Poikiloderma with Neutropenia recapitulates the human syndrome hallmarks and traces back neutropenia to the myeloid progenitor. *Scientific reports.* 5, 15814 (2015).
10. C. Hilcenko, P. J. Simpson, A. J. Finch, F. R. Bowler, M. J. Churcher, L. Jin, L. C. Packman, A. Shlien, P. Campbell, M. Kirwan, I. Dokal, A. J. Warren, Aberrant 3' oligoadenylation of spliceosomal U6 small nuclear RNA in poikiloderma with neutropenia. *Blood.* 121, 1028-38 (2013).
11. W. C. Fok, E. L. de O. Niero, C. Dege, K. A. Brenner, C. M. Sturgeon, L. F. Z. Batista, p53 Mediates Failure of Human Definitive Hematopoiesis in Dyskeratosis Congenita. *Stem Cell Rep.* 9, 409-418 (2017).
12. W. C. Fok, S. Shukla, A. T. Vessoni, K. A. Brenner, R. Parker, C. M. Sturgeon, L. F. Z. Batista, Posttranscriptional modulation of TERC by PAPD5 inhibition rescues hematopoietic development in dyskeratosis congenita. *Blood.* 133, 1308-1312 (2019).
13. S. Shukla, H.-C. Jeong, C. M. Sturgeon, R. Parker, L. F. Z. Batista, Chemical inhibition of PAPD5/7 rescues telomerase function and hematopoiesis in dyskeratosis congenita. *Blood Adv.* 4, 2717-2722 (2020).
14. C. M. Sturgeon, A. Ditadi, G. Awong, M. Kennedy, G. Keller, Wnt signaling controls the specification of definitive and primitive hematopoiesis from human pluripotent stem cells. *Nat Biotechnol.* 32, 554-561 (2014).
15. A. Ditadi, C. M. Sturgeon, Directed differentiation of definitive hemogenic endothelium and hematopoietic progenitors from human pluripotent stem cells. *Methods.* 101, 65-72 (2016).
16. M. de Bruijn, E. Dzierzak, Runx transcription factors in the development and function of the definitive hematopoietic system. *Blood.* 129, 2061-2069 (2017).
17. R. Avellino, R. Delwel, Expression and regulation of C/EBPα in normal myelopoiesis and in malignant transformation. *Blood.* 129, 2083-2091 (2017).
18. R. Yamanaka, C. Barlow, J. Lekstrom-Himes, L. H. Castilla, P. P. Liu, M. Eckhaus, T. Decker, A. Wynshaw-Boris, K. G. Xanthopoulos, Impaired granulopoiesis, myelodysplasia, and early lethality in CCAAT/enhancer binding protein ε-deficient mice. *Proc National Acad Sci.* 94, 13187-13192 (1997).
19. R. Morosetti, D. J. Park, A. M. Chumakov, I. Grillier, M. Shiohara, A. F. Gombart, T. Nakamaki, K. Weinberg, H. P. Koeffler, A Novel, Myeloid Transcription Factor, C/EBPε, Is Upregulated During Granulocytic, But Not Monocytic, Differentiation. *Blood.* 90, 2591-2600 (1997).
20. C.-Z. Chen, L. Li, H. F. Lodish, D. P. Bartel, MicroRNAs Modulate Hematopoietic Lineage Differentiation. *Science.* 303, 83-86 (2004).
21. F. Fazi, A. Rosa, A. Fatica, V. Gelmetti, M. L. D. Marchis, C. Nervi, I. Bozzoni, A Minicircuitry Comprised of MicroRNA-223 and Transcription Factors NFI-A and C/EBPα Regulates Human Granulopoiesis. *Cell.* 123, 819-831 (2005).
22. V. Licursi, F. Conte, G. Fiscon, P. Paci, MIENTURNET: an interactive web tool for microRNA-target enrichment and network-based analysis. *Bmc Bioinformatics.* 20, 545 (2019).
23. S. Shukla, G. A. Bjerke, D. Muhlrad, R. Yi, R. Parker, The RNase PARN Controls the Levels of Specific miRNAs that Contribute to p53 Regulation. *Mol Cell.* 73, 1204-1216.e4 (2019).
24. Y. Nomura, D. Roston, E. J. Montemayor, Q. Cui, S. E. Butcher, Structural and mechanisticbasis for preferential deadenylation of U6 snRNA by Usb1. *Nucleic Acids Res.* 46, gky812-(2018).
25. H. Mueller, A. Lopez, P. Tropberger, S. Wildum, J. Schmaler, L. Pedersen, X. Han, Y. Wang, S. Ottosen, S. Yang, J. A. T. Young, H. Javanbakht, PAPD5/7 Are Host Factors That AreRequired for Hepatitis B Virus RNA Stabilization. *Hepatology.* 69, 1398-1411 (2019).
26. H.-M. Chang, R. Triboulet, J. E. Thornton, R. I. Gregory, A role for the Perlman syndrome exonuclease Dis3l2 in the Lin28-let-7 pathway. *Nature.* 497, 244-248 (2013).
27. I. Heo, C. Joo, J. Cho, M. Ha, J. Han, V. N. Kim, Lin28 Mediates the Terminal Uridylationof let-7 Precursor MicroRNA. *Mol Cell.* 32, 276-284 (2008).
28. D. Ustianenko, J. Pasulka, Z. Feketova, L. Bednarik, D. Zigackova, A. Fortova, M. Zavolan, S. Vanacova, TUT-DIS3L2 is a mammalian surveillance pathway for aberrant structured non coding RNAs. *Embo J.* 35, 2179-2191 (2016).
29. R. M. Lardelli, J. Lykke-Andersen, Competition between maturation and degradation driveshuman snRNA 3' end quality control. *Gene Dev.* 34, 989-1001 (2020).
30. S. Shukla, J. C. Schmidt, K. C. Goldfarb, T. R. Cech, R. Parker, Inhibition of telomerase RNA decay rescues telomerase deficiency caused by dyskerin or PARN defects. *Nature structural & molecular biology* (2016), doi: 10.1038/nsmb.3184.
31. C.-K. K. Tseng, H.-F. F. Wang, A. M. Burns, M. R. Schroeder, M. Gaspari, P. Baumann, Human Telomerase RNA Processing and Quality Control. *Cell reports.* 13, 2232-43 (2015).
32. J. Sheu-Gruttadauria, P. Pawlica, S. M. Klum, S. Wang, T. A. Yario, N. T. S. Oakdale, J. A. Steitz, I. J. MacRae, Structural Basis for Target-Directed MicroRNA Degradation. *Mol Cell.* 75, 1243-1255.e7 (2019).
33. J. P. Hagan, E. Piskounova, R. I. Gregory, Lin28 recruits the TUTase Zcchc11 to inhibit let-7 maturation in mouse embryonic stem cells. *Nat Struct Mol Biol.* 16, 1021-1025 (2009).
34. A. M. Bolger, M. Lohse, B. Usadel, Trimmomatic: a flexible trimmer for Illumina sequence data. *Bioinformatics.* 30, 2114-2120 (2014).
35. R. Patro, G. Duggal, M. I. Love, R. A. Irizarry, C. Kingsford, Salmon provides fast and bias-aware quantification of transcript expression. *Nat Methods.* 14, 417-419 (2017).
36. M. I. Love, W. Huber, S. Anders, Moderated estimation of fold change and dispersion for RNA-seq data with DESeq2. *Genome Biol.* 15, 550 (2014).
37. A. Dobin, C. A. Davis, F. Schlesinger, J. Drenkow, C. Zaleski, S. Jha, P. Batut, M. Chaisson, T. R. Gingeras, STAR: ultrafast universal RNA-seq aligner. *Bioinformatics.* 29, 15-21 (2013).
38. J. Vaquero-Garcia, A. Barrera, M. R. Gazzara, J. Gonzalez-Vallinas, N. F. Lahens, J. B. Hogenesch, K. W. Lynch, Y. Barash, A new view of transcriptome complexity and regulation through the lens of local splicing variations. *Elife.* 5, e11752 (2016).
39. M. Martin, Cutadapt removes adapter sequences from high-throughput sequencing reads. *Embnet J.* 17, 10-12 (2011).
40. B. Langmead, S. L. Salzberg, Fast gapped-read alignment with Bowtie 2. *Nat Methods.* 9, 357-359 (2012).
41. K. C. Goldfarb, T. R. Cech, 3' terminal diversity of MRP RNA and other human noncoding RNAs revealed by deep sequencing. *BMC Molecular Biology.* 14, 23 (2013).

SEQUENCE LISTING

SEQ ID NO. 1
Amino Acid
USB1
*Homo sapiens*
MSAAPLVGYSSSGSEDESEDGMRTRPGDGSHRRGQSPLPRQRFPVPDSVLNMFPGTEEGPEDDS
TKHGGRVRTFPHERGNWATHVYVPYEAKEEFLDLLDVLLPHAQTYVPRLVRMKVFHLSLSQSVV
LRHHWILPFVQALKARMTSFHRFFFTANQVKIYTNQEKTRTFIGLEVTSGHAQFLDLVSEVDRV
MEEFNLTTFYQDPSFHLSLAWCVGDARLQLEGQCLQELQAIVDGFEDAEVLLRVHTEQVRCKSG
NKFFSMPLK SEQ ID NO. 2
Amino Acid
PAPD5 protein
*Homo Sapiens*
MYRSGERLLGSHALPAEQRDFLPLETTNNNNNHHQPGAWARRAGSSASSPPSASSSPHPSAAVPAADPAD
SASGSSNKRKRDNKASGGRAAGGGRADGGGVVYSGTPWKRRNYNQGVVGLHEEISDFYEYMSPRPEEEKM
RMEVVNRIESVIKELWPSADVQIFGSFKTGLYLPTSDIDLVVFGKWENLPLWTLEEALRKHKVADEDSVK
VLDKATVPIIKLTDSFTEVKVDISFNVQNGVRAADLIKDFTKKYPVLPYLVLVLKQFLLQRDLNEVFTGG
IGSYSLFLMAVSFLQLHPREDACIPNTNYGVLLIEFFELYGRHFNYLKTGIRIKDGGSYVAKDEVQKNML
DGYRPSMLYIEDPLQPGNDVGRSSYGAMQVKQAFDYAYVVLSHAVSPIAKYYPNNETESILGRIIRVTDE
VATYRDWISKQWGLKNRPEPSCNGPVSSSSATQSSSSDVDSDATPCKTPKQLLCRPSTGNRVGSQDVSLE
SSQAVGKMQSTQTTNTSNSTNKSQHGSARLFRSSSKGFQGTTQTSHGSLMTNKQHQGKSNNQYYHGKKRK
HKRDAPLSDLCR SEQ ID NO. 3
Amino Acid
PAPD7 protein
*Homo Sapiens*
MQIWETSQGVGRGGSGFASYFCLNSPALDTAAAAGAAGRGSGGLGPALPAASPPPPGPTAPAALPPALLT
ALGPAAEGARRLHKSPSLSSSSSSSSSNAESGTESPGCSSSSSSSASLGRPGGGRGGAFFNFADGAPSAP
GTANGHPGPRGPAPAGSPSQHQFHPGRRKRENKASTYGLNYLLSGSRAAALSGGGGPGAQARPGTPWKS
RAYSPGIQGLHEEIIDFYNFMSPCPEEAAMRREVVKRIETVVKDLWPTADVQIFGSFSTGLYLPTSDIDL
VVFGKWERPPLQLLEQALRKHNVAEPCSIKVLDKATVPIIKLTDQETEVKVDISFNMETGVRAAEFIKNY
MKKYSLLPYLILVLKQFLLQRDLNEVFTGGISSYSLILMAISFLQLHPRIDARRADENLGMLLVEFFELY
GRNFNYLKTGIRIKEGGAYIAKEEIMKAMTSGYRPSMLCIEDPLLGPNDVGRSSYGAMQVKQVFDYAYIV
LSHAVSPLARSYPNRDAESTLGRIIKVTQEVIDYRRWIKEKWGSKAHPSPGMDSRIKIKERIATCNGEQT
QNREPESPYGQRLTLSLSSPQLLSSGSSASSVSSLSGSDVDSDTPPCTTPSVYQFSLQAPAPLMAGLPTA
LPMPSGKPQPTTSRTLIMTTNNQTRFTIPPPTLGVAPVPCRQAGVEGTASLKAVHHMSSPAIPSASPNPL
SSPHLYHKQHNGMKLSMKGSHGHTQGGGYSSVGSGGVRPPVGNRGHHQYNRTGWRRKKHTHTRDSLPVSL
SR

What is claimed is:

1. A method of downregulating miRNA expression in a cell comprising the step of downregulating the expression of usb17 in the cell via introduction of a CRISPR-mediated gene therapy that knocks out usb17 in the cell, and wherein the downregulated miRNA include at least one of the following: miR-142-5p, miR-199a-3p, and miR-223-3p.

2. The method of claim 1, wherein the cell comprises a human cell.

* * * * *

SEQUENCE LISTING

<160> NUMBER OF SEQ ID NOS: 21

<210> SEQ ID NO 1
<211> LENGTH: 265
<212> TYPE: PRT
<213> ORGANISM: Homo sapiens

<400> SEQUENCE: 1

Met Ser Ala Ala Pro Leu Val Gly Tyr Ser Ser Ser Gly Ser Glu Asp
1               5                   10                  15

Glu Ser Glu Asp Gly Met Arg Thr Arg Pro Gly Asp Gly Ser His Arg
            20                  25                  30

Arg Gly Gln Ser Pro Leu Pro Arg Gln Arg Phe Pro Val Pro Asp Ser
        35                  40                  45

Val Leu Asn Met Phe Pro Gly Thr Glu Glu Gly Pro Glu Asp Asp Ser
    50                  55                  60

Thr Lys His Gly Gly Arg Val Arg Thr Phe Pro His Glu Arg Gly Asn
65                  70                  75                  80

Trp Ala Thr His Val Tyr Val Pro Tyr Glu Ala Lys Glu Glu Phe Leu
                85                  90                  95

Asp Leu Leu Asp Val Leu Leu Pro His Ala Gln Thr Tyr Val Pro Arg
            100                 105                 110

Leu Val Arg Met Lys Val Phe His Leu Ser Leu Ser Gln Ser Val Val

```
                115                 120                 125
Leu Arg His His Trp Ile Leu Pro Phe Val Gln Ala Leu Lys Ala Arg
        130                 135                 140

Met Thr Ser Phe His Arg Phe Phe Thr Ala Asn Gln Val Lys Ile
145                 150                 155                 160

Tyr Thr Asn Gln Glu Lys Thr Arg Thr Phe Ile Gly Leu Glu Val Thr
                        165                 170                 175

Ser Gly His Ala Gln Phe Leu Asp Leu Val Ser Glu Val Asp Arg Val
                180                 185                 190

Met Glu Glu Phe Asn Leu Thr Thr Phe Tyr Gln Asp Pro Ser Phe His
                195                 200                 205

Leu Ser Leu Ala Trp Cys Val Gly Asp Ala Arg Leu Gln Leu Glu Gly
        210                 215                 220

Gln Cys Leu Gln Glu Leu Gln Ala Ile Val Asp Gly Phe Glu Asp Ala
225                 230                 235                 240

Glu Val Leu Leu Arg Val His Thr Glu Gln Val Arg Cys Lys Ser Gly
                        245                 250                 255

Asn Lys Phe Phe Ser Met Pro Leu Lys
                260                 265

<210> SEQ ID NO 2
<211> LENGTH: 572
<212> TYPE: PRT
<213> ORGANISM: Homo Sapiens

<400> SEQUENCE: 2

Met Tyr Arg Ser Gly Glu Arg Leu Leu Gly Ser His Ala Leu Pro Ala
1               5                   10                  15

Glu Gln Arg Asp Phe Leu Pro Leu Glu Thr Thr Asn Asn Asn Asn Asn
                20                  25                  30

His His Gln Pro Gly Ala Trp Ala Arg Arg Ala Gly Ser Ser Ala Ser
            35                  40                  45

Ser Pro Pro Ser Ala Ser Ser Pro His Pro Ser Ala Ala Val Pro
        50                  55                  60

Ala Ala Asp Pro Ala Asp Ser Ala Ser Gly Ser Ser Asn Lys Arg Lys
65                  70                  75                  80

Arg Asp Asn Lys Ala Ser Gly Gly Arg Ala Ala Gly Gly Gly Arg Ala
                        85                  90                  95

Asp Gly Gly Gly Val Val Tyr Ser Gly Thr Pro Trp Lys Arg Arg Asn
                100                 105                 110

Tyr Asn Gln Gly Val Val Gly Leu His Glu Glu Ile Ser Asp Phe Tyr
            115                 120                 125

Glu Tyr Met Ser Pro Arg Pro Glu Glu Glu Lys Met Arg Met Glu Val
        130                 135                 140

Val Asn Arg Ile Glu Ser Val Ile Lys Glu Leu Trp Pro Ser Ala Asp
145                 150                 155                 160

Val Gln Ile Phe Gly Ser Phe Lys Thr Gly Leu Tyr Leu Pro Thr Ser
                        165                 170                 175

Asp Ile Asp Leu Val Val Phe Gly Lys Trp Glu Asn Leu Pro Leu Trp
                180                 185                 190

Thr Leu Glu Glu Ala Leu Arg Lys His Lys Val Ala Asp Glu Asp Ser
            195                 200                 205

Val Lys Val Leu Asp Lys Ala Thr Val Pro Ile Ile Lys Leu Thr Asp
        210                 215                 220
```

```
Ser Phe Thr Glu Val Lys Val Asp Ile Ser Phe Asn Val Gln Asn Gly
225                 230                 235                 240

Val Arg Ala Ala Asp Leu Ile Lys Asp Phe Thr Lys Lys Tyr Pro Val
            245                 250                 255

Leu Pro Tyr Leu Val Leu Val Leu Lys Gln Phe Leu Leu Gln Arg Asp
        260                 265                 270

Leu Asn Glu Val Phe Thr Gly Ile Gly Ser Tyr Ser Leu Phe Leu
    275                 280                 285

Met Ala Val Ser Phe Leu Gln Leu His Pro Arg Glu Asp Ala Cys Ile
290                 295                 300

Pro Asn Thr Asn Tyr Gly Val Leu Leu Ile Glu Phe Phe Glu Leu Tyr
305                 310                 315                 320

Gly Arg His Phe Asn Tyr Leu Lys Thr Gly Ile Arg Ile Lys Asp Gly
            325                 330                 335

Gly Ser Tyr Val Ala Lys Asp Glu Val Gln Lys Asn Met Leu Asp Gly
            340                 345                 350

Tyr Arg Pro Ser Met Leu Tyr Ile Glu Asp Pro Leu Gln Pro Gly Asn
        355                 360                 365

Asp Val Gly Arg Ser Ser Tyr Gly Ala Met Gln Val Lys Gln Ala Phe
    370                 375                 380

Asp Tyr Ala Tyr Val Val Leu Ser His Ala Val Ser Pro Ile Ala Lys
385                 390                 395                 400

Tyr Tyr Pro Asn Asn Glu Thr Glu Ser Ile Leu Gly Arg Ile Ile Arg
            405                 410                 415

Val Thr Asp Glu Val Ala Thr Tyr Arg Asp Trp Ile Ser Lys Gln Trp
            420                 425                 430

Gly Leu Lys Asn Arg Pro Glu Pro Ser Cys Asn Gly Pro Val Ser Ser
        435                 440                 445

Ser Ser Ala Thr Gln Ser Ser Ser Asp Val Asp Ser Asp Ala Thr
    450                 455                 460

Pro Cys Lys Thr Pro Lys Gln Leu Leu Cys Arg Pro Ser Thr Gly Asn
465                 470                 475                 480

Arg Val Gly Ser Gln Asp Val Ser Leu Glu Ser Ser Gln Ala Val Gly
            485                 490                 495

Lys Met Gln Ser Thr Gln Thr Asn Thr Ser Asn Ser Thr Asn Lys
        500                 505                 510

Ser Gln His Gly Ser Ala Arg Leu Phe Arg Ser Ser Lys Gly Phe
    515                 520                 525

Gln Gly Thr Thr Gln Thr Ser His Gly Ser Leu Met Thr Asn Lys Gln
530                 535                 540

His Gln Gly Lys Ser Asn Asn Gln Tyr Tyr His Gly Lys Lys Arg Lys
545                 550                 555                 560

His Lys Arg Asp Ala Pro Leu Ser Asp Leu Cys Arg
            565                 570

<210> SEQ ID NO 3
<211> LENGTH: 772
<212> TYPE: PRT
<213> ORGANISM: Homo Sapiens

<400> SEQUENCE: 3

Met Gln Ile Trp Glu Thr Ser Gln Gly Val Gly Arg Gly Gly Ser Gly
1               5                   10                  15

Phe Ala Ser Tyr Phe Cys Leu Asn Ser Pro Ala Leu Asp Thr Ala Ala
            20                  25                  30
```

```
Ala Ala Gly Ala Ala Gly Arg Gly Ser Gly Leu Gly Pro Ala Leu
         35                  40                  45

Pro Ala Ala Ser Pro Pro Pro Gly Pro Thr Ala Pro Ala Ala Leu
 50                  55                  60

Pro Pro Ala Leu Leu Thr Ala Leu Gly Pro Ala Ala Glu Gly Ala Arg
 65                  70                  75                  80

Arg Leu His Lys Ser Pro Ser Leu Ser Ser Ser Ser Ser Ser Ser
             85                  90                  95

Ser Asn Ala Glu Ser Gly Thr Glu Ser Pro Gly Cys Ser Ser Ser Ser
            100                 105                 110

Ser Ser Ser Ala Ser Leu Gly Arg Pro Gly Gly Arg Gly Gly Ala
         115                 120                 125

Phe Phe Asn Phe Ala Asp Gly Ala Pro Ser Ala Pro Gly Thr Ala Asn
        130                 135                 140

Gly His Pro Gly Pro Arg Gly Pro Ala Pro Ala Gly Ser Pro Ser Gln
145                 150                 155                 160

His Gln Phe His Pro Gly Arg Arg Lys Arg Glu Asn Lys Ala Ser Thr
                165                 170                 175

Tyr Gly Leu Asn Tyr Leu Leu Ser Gly Ser Arg Ala Ala Ala Leu Ser
            180                 185                 190

Gly Gly Gly Gly Pro Gly Ala Gln Ala Pro Arg Pro Gly Thr Pro Trp
        195                 200                 205

Lys Ser Arg Ala Tyr Ser Pro Gly Ile Gln Gly Leu His Glu Glu Ile
210                 215                 220

Ile Asp Phe Tyr Asn Phe Met Ser Pro Cys Pro Glu Glu Ala Ala Met
225                 230                 235                 240

Arg Arg Glu Val Val Lys Arg Ile Glu Thr Val Val Lys Asp Leu Trp
                245                 250                 255

Pro Thr Ala Asp Val Gln Ile Phe Gly Ser Phe Ser Thr Gly Leu Tyr
                260                 265                 270

Leu Pro Thr Ser Asp Ile Asp Leu Val Val Phe Gly Lys Trp Glu Arg
            275                 280                 285

Pro Pro Leu Gln Leu Leu Glu Gln Ala Leu Arg Lys His Asn Val Ala
        290                 295                 300

Glu Pro Cys Ser Ile Lys Val Leu Asp Lys Ala Thr Val Pro Ile Ile
305                 310                 315                 320

Lys Leu Thr Asp Gln Glu Thr Glu Val Lys Val Asp Ile Ser Phe Asn
                325                 330                 335

Met Glu Thr Gly Val Arg Ala Ala Glu Phe Ile Lys Asn Tyr Met Lys
            340                 345                 350

Lys Tyr Ser Leu Leu Pro Tyr Leu Ile Leu Val Leu Lys Gln Phe Leu
        355                 360                 365

Leu Gln Arg Asp Leu Asn Glu Val Phe Thr Gly Gly Ile Ser Ser Tyr
370                 375                 380

Ser Leu Ile Leu Met Ala Ile Ser Phe Leu Gln Leu His Pro Arg Ile
385                 390                 395                 400

Asp Ala Arg Arg Ala Asp Glu Asn Leu Gly Met Leu Leu Val Glu Phe
                405                 410                 415

Phe Glu Leu Tyr Gly Arg Asn Phe Asn Tyr Leu Lys Thr Gly Ile Arg
            420                 425                 430

Ile Lys Glu Gly Gly Ala Tyr Ile Ala Lys Glu Glu Ile Met Lys Ala
        435                 440                 445
```

```
Met Thr Ser Gly Tyr Arg Pro Ser Met Leu Cys Ile Glu Asp Pro Leu
            450                 455                 460

Leu Pro Gly Asn Asp Val Gly Arg Ser Ser Tyr Gly Ala Met Gln Val
465                 470                 475                 480

Lys Gln Val Phe Asp Tyr Ala Tyr Ile Val Leu Ser His Ala Val Ser
                485                 490                 495

Pro Leu Ala Arg Ser Tyr Pro Asn Arg Asp Ala Glu Ser Thr Leu Gly
                500                 505                 510

Arg Ile Ile Lys Val Thr Gln Glu Val Ile Asp Tyr Arg Arg Trp Ile
            515                 520                 525

Lys Glu Lys Trp Gly Ser Lys Ala His Pro Ser Pro Gly Met Asp Ser
530                 535                 540

Arg Ile Lys Ile Lys Glu Arg Ile Ala Thr Cys Asn Gly Glu Gln Thr
545                 550                 555                 560

Gln Asn Arg Glu Pro Glu Ser Pro Tyr Gly Gln Arg Leu Thr Leu Ser
                565                 570                 575

Leu Ser Ser Pro Gln Leu Leu Ser Ser Gly Ser Ser Ala Ser Ser Val
            580                 585                 590

Ser Ser Leu Ser Gly Ser Asp Val Asp Ser Asp Thr Pro Pro Cys Thr
            595                 600                 605

Thr Pro Ser Val Tyr Gln Phe Ser Leu Gln Ala Pro Ala Pro Leu Met
610                 615                 620

Ala Gly Leu Pro Thr Ala Leu Pro Met Pro Ser Gly Lys Pro Gln Pro
625                 630                 635                 640

Thr Thr Ser Arg Thr Leu Ile Met Thr Thr Asn Asn Gln Thr Arg Phe
                645                 650                 655

Thr Ile Pro Pro Pro Thr Leu Gly Val Ala Pro Val Pro Cys Arg Gln
            660                 665                 670

Ala Gly Val Glu Gly Thr Ala Ser Leu Lys Ala Val His His Met Ser
            675                 680                 685

Ser Pro Ala Ile Pro Ser Ala Ser Pro Asn Pro Leu Ser Ser Pro His
            690                 695                 700

Leu Tyr His Lys Gln His Asn Gly Met Lys Leu Ser Met Lys Gly Ser
705                 710                 715                 720

His Gly His Thr Gln Gly Gly Tyr Ser Ser Val Gly Ser Gly Gly
                725                 730                 735

Val Arg Pro Pro Val Gly Asn Arg Gly His His Gln Tyr Asn Arg Thr
            740                 745                 750

Gly Trp Arg Arg Lys Lys His Thr His Thr Arg Asp Ser Leu Pro Val
            755                 760                 765

Ser Leu Ser Arg
    770

<210> SEQ ID NO 4
<211> LENGTH: 23
<212> TYPE: PRT
<213> ORGANISM: Artificial
<220> FEATURE:
<223> OTHER INFORMATION: Donor oligo 1

<400> SEQUENCE: 4

Ala Thr Thr Gly Gly Gly Cys Thr Thr Gly Ala Gly Gly Thr Cys Ala
1               5                   10                  15

Cys Thr Thr Cys Asn Gly Gly
            20
```

```
<210> SEQ ID NO 5
<211> LENGTH: 23
<212> TYPE: DNA
<213> ORGANISM: Artificial
<220> FEATURE:
<223> OTHER INFORMATION: Donor Oligo - 2
<220> FEATURE:
<221> NAME/KEY: misc_feature
<222> LOCATION: (21)..(21)
<223> OTHER INFORMATION: n is a, c, g, or t

<400> SEQUENCE: 5
ttgggcttga ggtcacttca ngg                                          23

<210> SEQ ID NO 6
<211> LENGTH: 21
<212> TYPE: DNA
<213> ORGANISM: Artificial
<220> FEATURE:
<223> OTHER INFORMATION: shRNA-1

<400> SEQUENCE: 6
gccacatata gagattggat a                                            21

<210> SEQ ID NO 7
<211> LENGTH: 21
<212> TYPE: DNA
<213> ORGANISM: Artificial
<220> FEATURE:
<223> OTHER INFORMATION: shRNA-2

<400> SEQUENCE: 7
cgatgttgga aggagttcat a                                            21

<210> SEQ ID NO 8
<211> LENGTH: 21
<212> TYPE: DNA
<213> ORGANISM: Artificial
<220> FEATURE:
<223> OTHER INFORMATION: shRNA-3

<400> SEQUENCE: 8
cccaatacaa actatggtgt t                                            21

<210> SEQ ID NO 9
<211> LENGTH: 24
<212> TYPE: RNA
<213> ORGANISM: Artificial
<220> FEATURE:
<223> OTHER INFORMATION: miR125a-native

<400> SEQUENCE: 9
ucccugagac ccuuuaaccu guga                                         24

<210> SEQ ID NO 10
<211> LENGTH: 29
<212> TYPE: RNA
<213> ORGANISM: Artificial
<220> FEATURE:
<223> OTHER INFORMATION: miR125a-oA

<400> SEQUENCE: 10
ucccugagac ccuuuaaccu gugaaaaaa                                    29

<210> SEQ ID NO 11
<211> LENGTH: 29
```

```
<212> TYPE: RNA
<213> ORGANISM: Artificial
<220> FEATURE:
<223> OTHER INFORMATION: miR125a-oU

<400> SEQUENCE: 11
ucccugagac ccuuuaaccu gugauuuuu                                    29

<210> SEQ ID NO 12
<211> LENGTH: 29
<212> TYPE: RNA
<213> ORGANISM: Artificial
<220> FEATURE:
<223> OTHER INFORMATION: miR125a-oUA

<400> SEQUENCE: 12
ucccugagac ccuuuaaccu gugauuaaa                                    29

<210> SEQ ID NO 13
<211> LENGTH: 29
<212> TYPE: RNA
<213> ORGANISM: Artificial
<220> FEATURE:
<223> OTHER INFORMATION: miR125a-oAU

<400> SEQUENCE: 13
ucccugagac ccuuuaaccu gugaaauuu                                    29

<210> SEQ ID NO 14
<211> LENGTH: 25
<212> TYPE: RNA
<213> ORGANISM: Artificial
<220> FEATURE:
<223> OTHER INFORMATION: U6-oU

<400> SEQUENCE: 14
aauucgugaa gcguuccaua uuuuu                                        25

<210> SEQ ID NO 15
<211> LENGTH: 32
<212> TYPE: RNA
<213> ORGANISM: Artificial
<220> FEATURE:
<223> OTHER INFORMATION: U6-oA

<400> SEQUENCE: 15
aauucgugaa gcguuccaua uuuuuaaaaa aa                                32

<210> SEQ ID NO 16
<211> LENGTH: 39
<212> TYPE: RNA
<213> ORGANISM: Artificial
<220> FEATURE:
<223> OTHER INFORMATION: U6-oUA

<400> SEQUENCE: 16
aauucgugaa gcguuccaua uuuuuaauaa uaauaauaa                         39

<210> SEQ ID NO 17
<211> LENGTH: 16
<212> TYPE: RNA
<213> ORGANISM: Artificial
<220> FEATURE:
<223> OTHER INFORMATION: 16mer-native

<400> SEQUENCE: 17
```
ccuuuccccu uuccgc                                                    16

<210> SEQ ID NO 18
<211> LENGTH: 16
<212> TYPE: RNA
<213> ORGANISM: Artificial
<220> FEATURE:
<223> OTHER INFORMATION: 16mer-oA

<400> SEQUENCE: 18
ccuuuccaaa aaaaaa                                                    16

<210> SEQ ID NO 19
<211> LENGTH: 16
<212> TYPE: RNA
<213> ORGANISM: Artificial
<220> FEATURE:
<223> OTHER INFORMATION: 16mer-oU

<400> SEQUENCE: 19
ccuuuccuuu uuuuuu                                                    16

<210> SEQ ID NO 20
<211> LENGTH: 16
<212> TYPE: RNA
<213> ORGANISM: Artificial
<220> FEATURE:
<223> OTHER INFORMATION: 16mer-oUA

<400> SEQUENCE: 20
ccuuuccuuu uaaaaa                                                    16

<210> SEQ ID NO 21
<211> LENGTH: 16
<212> TYPE: RNA
<213> ORGANISM: Artificial
<220> FEATURE:
<223> OTHER INFORMATION: 16mer-oAU

<400> SEQUENCE: 21
ccuuuccaaa auuuuu                                                    16